(12) United States Patent
Tilly et al.

(10) Patent No.: US 9,962,411 B2
(45) Date of Patent: May 8, 2018

(54) ISOLATED POPULATIONS OF FEMALE GERMLINE STEM CELLS AND CELL PREPARATIONS AND COMPOSITIONS THEREOF

(71) Applicant: The General Hospital Corporation, Boston, MA (US)

(72) Inventors: Jonathan Lee Tilly, Windham, NH (US); Joshua Johnson, New Haven, CT (US)

(73) Assignee: The General Hospital Corporation, Boston, MA (US)

( * ) Notice: Subject to any disclaimer, the term of this patent is extended or adjusted under 35 U.S.C. 154(b) by 269 days.

(21) Appl. No.: 14/315,220

(22) Filed: Jun. 25, 2014

(65) Prior Publication Data

US 2014/0308253 A1    Oct. 16, 2014

Related U.S. Application Data

(60) Continuation of application No. 14/160,193, filed on Jan. 21, 2014, now abandoned, which is a division of application No. 13/090,904, filed on Apr. 20, 2011, now Pat. No. 8,652,840, which is a division of application No. 11/131,114, filed on May 17, 2005, now Pat. No. 7,955,846.

(60) Provisional application No. 60/572,222, filed on May 17, 2004, provisional application No. 60/574,187, filed on May 24, 2004, provisional application No. 60/586,641, filed on Jul. 9, 2004.

(51) Int. Cl.
| | |
|---|---|
| *A61K 35/54* | (2015.01) |
| *A01K 67/027* | (2006.01) |
| *C12N 5/0735* | (2010.01) |
| *C12N 15/877* | (2010.01) |
| *C12N 5/074* | (2010.01) |

(52) U.S. Cl.
CPC .......... *A61K 35/54* (2013.01); *A01K 67/0271* (2013.01); *A01K 67/0275* (2013.01); *C12N 5/0607* (2013.01); *C12N 5/0611* (2013.01); *C12N 15/8775* (2013.01); *A01K 2217/05* (2013.01); *A01K 2227/105* (2013.01); *A01K 2267/0393* (2013.01)

(58) Field of Classification Search
CPC ............................ A61K 35/54; A01K 67/0271
See application file for complete search history.

(56) References Cited

U.S. PATENT DOCUMENTS

| | | | |
|---|---|---|---|
| 6,875,854 B1 | 4/2005 | Castillon | |
| 7,955,846 B2 | 6/2011 | Tilly et al. | |
| 8,062,222 B2 | 11/2011 | Dirtinger et al. | |
| 8,338,178 B2 | 12/2012 | Hyde et al. | |
| 8,445,277 B2 | 5/2013 | Hyde et al. | |
| 8,489,337 B2 | 7/2013 | Hyde et al. | |
| 8,527,208 B2 | 9/2013 | Hyde et al. | |
| 8,846,028 B2 | 9/2014 | Hyde et al. | |
| 8,903,660 B2 | 12/2014 | Hyde et al. | |
| 8,999,714 B2 | 4/2015 | Hyde et al. | |
| 2005/0130302 A1 | 6/2005 | Nakauchi et al. | |
| 2006/0010508 A1 | 1/2006 | Tilly et al. | |
| 2006/0010509 A1 | 1/2006 | Johnson et al. | |
| 2006/0015961 A1 | 1/2006 | Tilly et al. | |
| 2008/0050347 A1 | 2/2008 | Ichim | |
| 2009/0111764 A1 | 4/2009 | Hillis et al. | |
| 2012/0315651 A1 | 12/2012 | Tilly et al. | |
| 2013/0059384 A1 | 3/2013 | Tilly et al. | |
| 2013/0060079 A1 | 3/2013 | Tilly et al. | |

FOREIGN PATENT DOCUMENTS

| | | |
|---|---|---|
| EP | 1233978 A1 | 8/2002 |
| WO | WO-2001/30980 | 5/2001 |
| WO | WO-2001036445 A1 | 5/2001 |
| WO | WO-2004009758 A1 | 1/2004 |
| WO | WO-2005007687 A1 | 1/2005 |
| WO | WO2005/113752 | 12/2005 |
| WO | WO2005/121321 | 12/2005 |
| WO | WO/2006/001938 | 1/2006 |
| WO | WO-2012/142500 | 10/2012 |

OTHER PUBLICATIONS

Grieve et al (Maturitas, 82: 278-281, 2015).*
Yazdekhasti et al (Journal of Ovarian Research, 9(68), 1-12, 2016).*
Tracey Baas et al., "Repowering the Ovary" Science Business Exchange, vol. 5, No. 10.
Office Action issued in Chinese application No. 201280018195.1, filed Apr. 13, 2012.
Kong Ling-Hong et al, "Mitochondria transfer from self-granular cells to improve embryos' quality", Chin J. Obstet Gynecol, 39(2): 105-107 (2004).
Perez G I et al, "Further Studies on the role of Mitochondria in Controlling Oocyte Apoptosis", Biology of Reproduction, New York, NY [U.A.] : Academ. Press, US. (Jan. 1, 2000), vol. 62, Suppl. 01, (2000).
ISR/Written Opinion issued in PCT/US2005/017233, dated Feb. 26, 2007, The General Hospital Corp.
ISR/Written Opinion/IPRP issued in PCT/US2005/017221, dated Jul. 27, 2006, The General Hospital Corp.
ISR/Written Opinion/IPRP issued in PCT/US2005/017234, dated Aug. 10, 2006, The General Hospital Corp.
Supplementary Search Report issued in EP-05779982.7, dated Sep. 17, 2008, The General Hospital Corp.
Supplementary Search Report issued in EP-05783644.7, dated Sep. 23, 2008, The General Hospital Corp.
Supplementary Search Report issued in EP-05782697.6, dated Oct. 15, 2008, The General Hospital Corp.

(Continued)

*Primary Examiner* — Anoop K Singh
(74) *Attorney, Agent, or Firm* — Saul Ewing Arnstein & Lehr LLP; Peter C. Lauro, Esq.

(57) ABSTRACT

The present invention relates to female germline stem cells and their progenitors, methods of isolation thereof, and methods of use thereof.

14 Claims, 22 Drawing Sheets

(56) References Cited

OTHER PUBLICATIONS

International Preliminary Report on Patentability issued for PCT/US05/17233, dated Jul. 25, 2008, The General Hospital Corp.
International Preliminary Report on Patentability issued for PCT/US05/17234, dated Jul. 25, 2008, The General Hospital Corp.
ISR issued PCT/US2012/033643 (WO-2012/142500), dated Oct. 10, 2012, Tilly et al.
Written Opinion issued in PCT/US2012/033643, dated Oct. 10, 2012, Tilly et al.
ISR issued in PCT/US2012/033672, dated Oct. 16, 2012, Tilly et al.
Powell, K., Going Against the Grain, PloS Biol 2007; 5:e338 (doi:10.1371/journal.pbio.0050338).
Bazer FW., Strong science challenges conventional wisdom: new perspectives on ovarian biology. Reprod Biol Endocrinol 2004; 2:28.
Gougeon A., Neo-oogenesis in the postnatal ovary: fantasy or reality? Gynecol Obstet Fertil 2005; 33:819-823.
Kayisli UA et al., Stem cells and fertility: what does the future hold? Curr Opin Obstet Gynecol 2006; 18:338-343.
Faddy M. et al., Numbers of ovarian follicles and testing germ line renewal in the postnatal ovary. Facts and fallacies. Cell Cycle 2007; 6:1951-1952.
Oktem O. et al., Stem cells: a perspective on oocytes. Ann NY Acad Sci USA 2008; 1127:20-26.
Zuckerman S., Beyond the Ivory Tower. The Frontiers of Public and Private Science. New York: Taplinger; 1971:22-34.
Waldeyer W. Eierstock und Ei. Engelmann, Leipzig; 1870.
Zhang D et al., Expression of stem and germ cell markers within nonfollicle structures in adult mouse ovary. Reprod Sci 2008; 15:139-146.
Vermande-Van Eck G. , Neo-ovogenesis in the adult monkey. Anat Rec 1956; 125:207-224.
Flaws JA, et al., Chronically elevated luteinizing hormone depletes primordial follicles in the mouse ovary. Biol Reprod 1997; 57:1233-1237.
Dissen GA, et al., Romero C., Hirshfield AN, Ojeda Sr. Nerve growth factor is required for early follicular development in the mammalian ovary. Endocrinology 2001; 142:2078-2086.
Nilsson EE, et al., Bone morphogenetic protein-4 acts as an ovarian follicle survival factor and promotes primordial follicle development. Biol Reprod 2003; 69:1265-1272.
Tomic D et al., Ovarian follicle development requires Smad3, Mol Endocrinol 2004; 18:2224-2240.
Rajkovia A et al., NOBOX deficiency disrupts early folliculogenesis and oocyte-specific gene expression. Science 2004; 305:1157-1159.
Castrillon DH et al., Suppression of ovarian follicle activation in mice by the transcription factor Foxo3a. Science 2004; 301:215-218.
Lohff JC et al., Effect of duration of dosing on onset of ovarian failure in a chemical-induced mouse model of perimenopause. Menopause 2006; 13:482-488.
Reddy P et al., Oocyte-specific deletion of Pten causes premature activation of the primordial follicle pool. Science 2008; 319:611-613.
Gosden RG. Ovarian support of pregnancy in ageing inbred mice. J Reprod Fertil 1975; 42:423-430.
Gosden RG. Effects of age and parity on the breeding potential of mice with one or two ovaries. J. Reprod Fertil 1979; 57:477-487.
Nelson JF et al., Effects of dietary restriction on estrous cyclicity and follicular reserves in aging C57BL/6Jmice. Biol Reprod 1985; 32:515-522.
Eichenlaub-Ritter U et al., The CBA mouse as a model for age-related aneuploidy in man: studies of oocyte maturation, spindle formation and chromosome alignment during meiosis. Chromosoma (Berl) 1988; 96:220-226.
Allen E. Ovogenesis during sexual maturity. Am J Anat 1923; 31:439-482.
Bucci LR et al., Effects of busulfan on murine spermatogenesis: cytotoxicity, sterility, sperm abnormalities and dominant lethal mutations. Mutat Res 1987; 176:259-268.
Brinster RL et al., Germline transmission of donor haplotype following spermatogonial transplantation. Proc Natl Acad Sci USA 1994; 91:11303-11307.
Ogawa T et al., Transplantation of testis germinal cells into mouse seminiferous tubules. Int J. Dev Biol 1997; 41 :111-122.
Pelloux MC et al., Effects of busulphan on ovarian folliculogenesis, steroidogenesis and anti-Mullerian activity of rat neonates. Acta Endocrinol 1988; 118:218-226.
Perez GI et al., Apoptosis-associated signaling pathways are required for chemotherapy-mediated female germ cell destruction. Nat Med 1997; 3:1228-1232.
Perez GI et al., Fragmentation and death (a.k.a. apoptosis) of ovulated oocytes. Mol Hum Reprod 1999; 5:414-420.
Morita Y et al., Oocyte apoptosis is suppressed by disruption of the acid sphingomyelinase gene or by sphingosine-1-phosphate therapy. Nat Med 2000; 6:1109-1114.
Baltus AE et al., In germ cells of mouse embryonic ovaries, the decision to enter meiosis precedes premeiotic DNA replication. Nat Genet 2006; 38:1430-1434.
Zhou Q et al., Expression of stimulated by retinoic acid gene 8 (Stra8) and maturation of murine gonocytes and spermatogonia induced by retinoic acid in vitro. Biol Reprod 2008; 78:537-545.
Wang N et al., Inhibition of histone deacetylase activity amplifies retinoic acid-mediated induction of Stra8 expression and oogenesis in ovaries of adult female mice. Proceedings of the 41st Annual Meeting of the Society for the Study of Reproduction, Kailua-Kona, Big Island, HI; p. 132 (Abstract 291).
Bowles J et al., Retinoic acid signaling determines germ cell fate in mice. Science 2006; 312:596-600.
Koubova J et al., Retinoic acid regulates sex-specific tijmning of meiotic initiation in mice. Proc Natl Acad Sci USA 2006; 103:2474-2479.
Lee H-J et al., Loss of CABLES1, a cyclin-dependent kinase-interacting protein that inhibits cell cycle progression, results in germline expansion at the expense of oocyte quality in adult female mice. Cell Cycle 2007; 6:2678-2684.
Bristol-Gould SK et al., Postnatal regulation of germ cells by activin: the establishment of the initial follicle pool. Dev Biol 2006; 298:132-148.
Lin H. The stem-cell niche theory: lessons from flies. Nat Rev Genet 2002; 3:931-940.
Ogawa T et al., The niche for spermatogonial stem cells in the mammalian testis. Int. J. Hematol 2005; 82: 381-388.
Bukovsky A et al., Origin of germ cells and formation of new primary follicles in adult human ovaries. Reprod Biol Endocrinol 2004; 2:28.
Bukovsky A et al., Oogenesis in cultures derived from adult human ovaries. Reprod Biol Endocrinol 2005; 3:17.
Bukovsky A et al., Mammalian neo-oogenesis and expression of meiosis-specific protein SCP3 in adult human and monkey ovaries. Cell Cycle 2008; 7:683-686.
Bristol-Gould SK et al., Fate of the initial follicle pool: empirical and mathematical evidence supporting its sufficiency for adult fertility. Dev Biol 2006; 298:149-154.
Peters H. The development of the mouse ovary from birth to maturity. Acta Endocrinol 1969; 62:98-116.
Elvin JA et al., Molecular characterization of the follicle defects in the growth differentiation factor 9-deficient ovary. Mol Endocrinol 1999; 13: 1018-1034.
Myers M et al., Methods for quantifyying follicular numbers within the mouse ovary. Reproduction 2004; 127:569-580.
Huntriss J et al., cDNA cloning and expression of the human NOBOX gene in oocytes and ovarian follicles. Mol Hum Reprod 2006; 12:283-289.
John GN et al., Specificity of the requirement for Foxo3 in primordial follicle activation. Reproduction 2007; 133:855-863.
Ohta H et al., Commitment of fetal male germ cells to spermatogonial stem cells during mouse embryonic development. Biol Reprod 2004; 70:1286-1291.

(56) References Cited

OTHER PUBLICATIONS

Hubner K et al., Derivation of oocytes from mouse embryonic stem cells. Science 2003; 300:1251-1256.
Novak I et al., Mouse embryonic stem cells form follicle-like ovarian structures but do not progress through meiosis. Stem Cells 2006; 8:1931-1936.
Kerkis A et al., In vitro differentiation of male mouse embryonic stem cells into both presumptive sperm cells and oocytes. Cloning Stem Cells 2007; 9:535-548.
Nagano MC. In vitro gamete derivation from pluripotent stem cells: progress and perspective. Biol Reprod 2007; 76:546-551.
Dyce PW et al., In vitro germline potential of stem cells derived from fetal porcine skin. Nat Cell Biol 2006; 8:384-390.
Dyce PW et al., From skin cells to ovarian follicles? Cell Cycle 2006; 5:1371-1375.
Danner S et al., Derivation of oocyte-like cells from a clonal pancreatic stem cell line. Mol Hum Reprod 2007; 13:11-20.
Toyooka Y et al., Embryonic stem cells can form germ cells in vitro. Proc Natl Acad Sci USA 2003; 100:11457-11462.
Geijsen N et al., Derivation of embryonic germ cells and male gametes from embryonic stem cells. Nature 2004; 427:148-154.
Lue Y et al., Fate of bone marrow stem cells transplanted into the the testis: implications for men with testicular failure. Am J Pathol 2007; 170;899-908.
Drusenheimer N et al., Putative human male germ cells from bone marrow stem cells. Soc Reprod Fertil Suppl 2007; 63:69-76.
Yeom YI et al., Germline regulatory element of Oct-4 specific for the totipotent cycle of embryonal cells. Development 122:881-894.
Yoshimizu T et al., Germline-specific expression of the Oct-4/green fluorescent protein (GFP) transgene in mice. Dev Growth Differ 1999; 41:675-684.
Szabo PE et al., Allele-specific expression of imprinted genes in mouse migratory primordial germ cells. Mech Dev 2002; 115:157-160.
Begum S et al., The oocyte population is not renewed in transplanted or irradiated adult ovaries. Hum Reprod 2008; (doi:10.1093/humrep/den249).
Fu X et al., Bone marrow mesenchymal stem cell transplanation improves ovarian function and structure in rats with chemotherapy-induced damage. Cytotherapy 2008; 10:353-363.
Tilly JL et al., Stem cell contribution to ovarian development, function and disease. Endocrinology 2008; (doi:10.1210/en.2008-0458).
Shankle WR et al., Evidence for a postnatal doubling of neuron number in the developing human cerebral cortex between 15 months and 6 years. J Theor Biol 1998; 191:115-140.
Shankle WR et al., Approximate doubling of numbers of neurons in postnatal human cerebral cortex and in 35 specific cytoarchitectural areas from birth to 72 months. Pediatr Dev Pathol 1999; 2:244-259.
Gould E et al., Neurogenesis in the neocortex of adult primates. Science 1999; 286:548-552.
Korr H et al., Facts and fictions regarding post-natal neurogenesis in the developing human cerebral cortex. J Theor Biol 1999; 200:291-297.
Nowakowski RS et al., New Neurons: extraordinary evidence or extraordinary conclusion? Science 2000; 288:771a.
Rakic P. Neurogenesis in the adult primate neocortex: an evaluation of the evidence. Nat Rev Neurosci 2002; 3:65-71.
Blakeslee S. A decade of discovery yields a shock about the brain. New York Times 2000 (Jan.); F1, F4.
Gross CG. Neurogenesis in the adult brain: death of a dogma. Nat Rev Neurosci 2000; 1:67-73.
Gould E et al., Adult-generated hippocampal and neocortical neurons in macaques have a transient existence. Proc Natl Acad Sci USA 2001; 98: 10910-10917.
Gould E et al., Neurogenesis in adult mammals: some progress and problems. J Neurosci 2002; 22:619-623.
Leuner B et al., Diminished neurogenesis in the marmoset brain precedes old age. Proc Natl Acad Sci USA 2007; 104:17169-17173.

Revishchin AV et al., Neural stem cells in the mammalian brain. Int Rev Cytol 2008; 265-55-109.
Maurer MH et al., Screening the brain: molecular fingerprints of neural stem cells. Curr Stem Cell Res Ther 2006; 1:65-77.
Taupin P. Therapeutic potential of adult neural stem cells. Rec Patents CNS Drug Discov 2006; 1:299-303.
Beaumont HM et al., A quantitative and cytological study of oogonia and oocytes in the fetal and neonatal rat. Proc R Soc Lond B 1961; 155:557-579.
Baker TG et al., The fine structure of oogonia and oocytes in human ovaries. J Cell Sci 1967; 2:213-224.
Gosden RG. Follicular status at menopause. Hum Reprod 1987; 2:617-621.
Selesniemi K et al., Moderate caloric restriction initiated in rodents during adulthood sustains function of the female reproductive axis into advanced chronological age. Aging Cell 2008; (doi:10.1111/j.1474-9726.2008.00409.x).
Perez GI et al., Absence of the pro-apoptotic Bax protein extends fertility and alleviates age-related health complications in female mice. Proc Natl Acad Sci USE 2007; 104: 5229-5234.
Kirilly D et al., The *Drosophila* ovary: an active stem cell community. Cell Res 2007; 17:15-25.
Pearl R et al., Studies on the physiology of reproduction in the domestic fowl. J Exp Zool 1921; 34:101-118.
Underwood JL et al., Gonad regeneration in grass carp following bilateral gonadectomy. Progressive Fish-Culturist 1986; 48:54-56.
Draper BW et al., nanos1 is required to maintain oocyte production in adult zebrafish. Dev Biol 2007; 305:589-598.
Salooja N et al., Successful pregnancies in women following single autotransplant for acute myeloid leukemia with a chemotherapy ablation protocol. Bone Marrow Transplant 1994; 13:431-435.
Socie G et al., Late Effects Working Party of the European Study Group for Blood and Marrow Transplantation. Nonmalignant late effects after allogeneic stem cell transplantation. Blood 2003; 101:3373-3385.
Oktay K et al., Regeneration of oocytes after chemotherapy: connecting the evidence from mouse to human. J. Clin Oncol 2007; 25:3185-3187.
Tropel P et al., Isolation and Characterization of Mesenchymal Stem Cells from Adult Mouse Bone Marow. Experimental Cell Research, May 1, 2004. 295(2); 395-406.
Logothetou-Rella "Description of primordial germ cells, oogonia, oocytes and embryo-like growth in squash preparations of tissues from hematological malignancies" Histol Histopathol. 11(4): 965-984 (1996).
Nayernia et al. "Derivation of male germ cells from bone marrow stem cells" Lab Invest. 86(7): 654-663 (2006).
Johnson et al. "Oocyte Generation in Adult Mammalian Ovaries by Putative Germ Cells in Bone Marrow and Peripheral Blood" Cell 122: 303-315 (2005).
Kucia et al. "A population of very small embryonic-like (VSEL) CZCR4+SSEA-1+ Oct-4+ Stem cells identified in adult bone marrow" Luekemia 20: 857-869 (2006).
Pochampally et al. "Serum deprivation of human marrow stromal cells (hMSCs) selects for a subpopulation of early progenitor cells with enhanced expression of OCT-4 and other embryonic genes" Blood 103(5): 1647-1652 (2004).
Hayashi et al. "Mouse preimplantation Embryos Developed from Oocytes Injected with Round Spermatids or Spermatozoa Have Similar but Distinct Patterns of Early Messenger RNA Expression" Biology of Reproduction 69: 1170-1176 (2003).
Hovatta et al. "A culture system using human foreskin fibroblasts as feeder cells allows production of human embryonic stem cells" Human Reproduction 18(7): 1404-1409 (2003).
Bukovsky et al. "Potential new strategies for the treatment of ovarian infertility and degenerative diseases with autologous ovarian stem cells" Expert Opin. Biol. Ther. 6(4): 341-365 (2006).
Eggan et al. "Ovulated oocytes in adult mice derive from non-circulating germ cells." Nature 441; 1109-1114 (2006).
Anderson, Biol Reprod. 1988; 38(1) 1-15.
Decotto et al., Dev cell. 2005; 9(4): 501-10.
Gage, F., Nature 392: 18-24, 1998.

(56) References Cited

OTHER PUBLICATIONS

Goswami et al., 2005. Premature Ovarian Failure. Hum Reprod Update 11: 391-410.
Hildebrandt et al., 2000. Detection of Germ-cell Tumor Cells in Peripheral Blood Progenitor Cell Harvests: Impact on Clinical Outcome. Clin Cancer Res 6: 4641-4646.
Samstein et al., Journal of American Society of Nephrology 12: 182-193, 2001.
Virant-Klun et al., Stem Cells and Development, Jul. 2008 pp. 1-43.
Yamashita et al., Journal of Cell Science 118, 665-672, 2005.
Powell "Skeptics demand duplication of controversial fertility claim" Nat Med 11:911 (2005).
Powell "Born or made? Debate on mouse eggs reignites" Nature 441: 795 (2006).
Ainsworth "Bone cells linked to creation of fresh eggs in mammals" Nature 436: 609 (2005).
Greenfeld et al. "Renewed debate over postnatal oogenesis in the mammalian ovary" Bioessays 26:829-32 (2004).
Gosden "Germline stem cells in the postnatal ovary: is the ovary more like a testis?" Hum Reprod Update 10(3) 193-195 (2004).
Albertini "Micromanagement of the ovarian follicle reserve—do stem cells play into the ledger?" Reproduction 127: 513-514 (2004).
Vogel "Controversial study finds unexpected source of oocytes" Science 309: 678-679 (2005).
Hoyer Can the clock be turned back on ovarian aging? Sci Aging Knowledge Environ 10:pe11 (2004).
Telfer "Germline stem cells in the postnatal mammalian ovary: a phenomenon of prosimian primates and mice?" Reprod Biol Endocrinol 2:24 (2004).
Telfer et al. "On regenerating the ovary and generating controversy" Cell 122: 821-22 (2005).
Kerr et al. "Quantification of healthy follicles in the noenatal and adult mouse ovary: evidence for maintenance of primordial follicle supply" Reproduction 132: 95-109 (2006).
Skaznik et al. "Serious doubts over Eggs forever?" Differentiation 74: 1-7 (2006).
Salooja et al. "Late Effects of working party of the European Group for blood and marrow transplantataion. Pregnancy outcomes after peripheral blood or bone marrow transplantation: a retrospective study." Lancet 358: 271-276 (2001).
Samuelsson et al. "Successful pregnancy in a 28 year old patient autographed for acute lymphoblastic leukemia following myeloablative treatment including total body irradiation." Bone Marrow Transplant 12: 659-660 (1993).
Sanders et al. "Pregnancies following high-dose cyclophosphamide with or without high-dose busulfan or total-body irradiation and bone marrow transplantation." Blood 87: 3045-3052 (1996).
Johnson et al. "Germline stem cells and follicular renewal in the postnatal mammalian ovary." Nature 48(11):145-150 (2004).
Hershlag et al. "Return of fertility after autologous stem cell transplantation." Fertility and Sterility 77(2) 419-421 (2002).
Zhou, K, et al. "Production of Offspring from a Germline Stem Cell Line Derived from Neonatal Ovaries" Nature Cell Biology Online Publication, published online Apr. 12, 2009; DOI 10.1038/ncb1869, pp. 1-20.
Tropel et al., Isolation and Characterization of Mesenchymal Stem Cells from Adult Mouse Bone Marrow. Experimental Cell Research, May 1, 2004. 295(2); 395-406.
Wittstock et al., Analytical Biochemistry, 292, 166-169, 2001.
Castrillon et al., (PNAS, 97-17: 9585-9590, 2000).
Clark, et al., (Stem Cells, 22: 169-179, 2004).
Johnson et al. "Germline stem cells and follicular renewal in the postnatal mammalian ovary" Nature 428: 145-150 (2004).
Byskov et al. "Eggs forever?" Differentiation 73: 438-446 (2005).
Johnson et al. "Setting the Record Straight on Data Supporting Postnatal Oogenesis in Female Mammals" Cell Cycle 4:11, 1 4771-1 477 (2005).
Logothetou-Rella Description of primordial germ cells, oogonia, oocytes and embryo-like growth in squash preparations of issues from hematological malignancies: Histology and Histopathology 11: 965-984(1996).
Logothetou-Rella "Meiosis in hematological malignancies. In situ cytogenetic morphology" Histology and Histopathology 11: 943-963 (1996).
Thomson et al., Science, 282: 1145-1147, 1998.
Clark et al., Human Molecular Genetics, 13(7): 727-739, 2004.
Reubinoff et al., Nature Biotechnology, 18: 399-404, 2000.
Lin et al., Stem Cells, 21: 152-161, 2003.
Gosden, Human Reproduction Update, 10(3): 193-195, 2004.
Bukovsky, et al., Reproductive Biology and Endocrinology, 2:20, 2004.
Spradling, Nature, 428: 133-134, 2004.
Balakier et al., "Morphological and Cytogenetic Analysis of Human Giant Oocytes and Giant Embryos" Human Reproduction 17(8): 2394-2401 (2002).
Sotile "Bone Marrow as a Source of Stem Cells and Germ Cells? Perspectives for Transplantation" Cell Tissue Res. 328:1-5 (2007).
Hua, Jinlian et al., Derivation of male germ cell-like lineage from human fetal bone marrow stem cells, Reproductive BioMedicine Online; www.rbmonline.com/Article/3742 on web May 8, 2009, vol. 19, No. 1. 2009-99-105.
Lovell-Badge, Robin, Banking on spermatogonial stem cells: Frozen assets and foreign investments, Nature Medicine, vol. 2, No. 6, Jun. 1996.
Meachem et al., Spermatogonia: stem cells with a great perspective, Reproduction (2001), 121, 825-834.
Nistal et al., Decrease in the Number Of Human Ap and Ad Spermatogonia and in the Ap/Ad Ratio with Advancing Age, J Androl 1987; 8:64-68.
Paniagua et al., Quantification of cell types throughout the cycle of the human seminiferous epithelium and their DNA content, Anatomy and Embryology (1987) 176: 225-230.
Schulze, Cornelia, Response of the human testis to long-term estrogen treatment: Morphology of Sertoli cells, Leydig cells and spermatogonial stem cells, Cell and Tissue Research (1998) 251:31-43.
Anderson "An overview of follicular development in the ovary: From embryo to the fertilized ovum in vitro." Md. Med. J. 41: 614-620 (1992).
Johnson et al., "Germline stem cells and follicular renewal in the postnatal mammalian ovary." Nature 428: 145-150 (2004).
Korbling et al. "Peripheral blood stem cell versus bone barrow allotransplantation: does the source of hematopoietic stemm cells matter?" Blood 98: 2900-2908 (2001).
Ho et al., "Hematopoietic stem cells: can old cells learn new tricks?" J Leukoc Biol 73: 547- 555 (2003).
Sanchez-Ramos "Neural Cells Derived From Adult Bone Marrow and Umbilical Cord Blood." J Neurosci Res 69: 880-893 (2002).
Lee "Isolation of multipotent mesenchymal stem cells from umbilical cord blood."Blood 103:1669-75 (2004).
Rogers et al. "Lifeline in an Ethical Quagmire: Umbilical Cord Blood as an Alternative to Embryonic Stem Cells." Sexuality, Reproduction & Menopause 2: 64-70 (2004).
Green et al. "Do cells outside the testes participate in repopulating the germinal epithelium after irradiation?" Int. J. Radiat. Biol. vol. 17 (1): 87-92 (1970).
Morita et al. "Oocyte Apoptosis: Like Sand through an Hourglass" Dev. Biol. 213: 1-17 (1999).
Tilly, J.L., "Commuting the Death Sentence: How Oocytes Strive to Survive." Nat. Rev. Mol. Cell Biol. 2: 838-848 (2001).
Faddy et al., "The kinetics of pre-antral follicle development in ovaries of CBA/Ca mice during the first 14 weeks of life." Cell Tissue Kinet. 20: 551-560 (1987).
Faddy, M.J., "Follicle dynamics during ovarian ageing." Mol. Cell. Endocrinol. 163: 43-48 (2000).
Faddy et al., "An Analytical Model for Ovarian Follicle Dynamics." J. Exp. Zool. 197: 173-186 (1976).
Richardson et al. "Follicular Depletion During the Menopausal Transition: Evidence for Accelerated Loss and Ultimate Exhaustion." J. Clin. Endocrinol. Metab. 65: 1231-1237 (1987).

(56) References Cited

OTHER PUBLICATIONS

Borum "Oogenesis in the Mouse, A Study of the Meiotic Prophase." *Exp. Cell Res.* 24: 495-507 (1961).
Mclaren "Meiosis and Differentiation of Mouse Germ Cells." *Symp. Soc. Exp. Biol.* 38: 7-23 (1984).
Peters "Migration of gonocytes into the mammalian gonad and their differentiation." *Phil. Trans. R. Soc. Lond. B*, 259: 91-101 (1970).
Waxman "Chemotherapy and the adult gonad: a review." *J. R. Soc. Med.* 76: 144-8 (1983).
Familiari et al., "Ultrastructure of human ovarian primordial follicles after combination chemotherapy for Hodgkin's disease." *Hum. Reprod.* 8: 2080-7 (1993).
Ried et al. " Radiation-Induced Changes in Long-Term Survivors of Childhood Cancer After Treatment with Radiation Therapy." *Semin. Roentgenol.* 29: 6-14 (1994).
Reichman et al. "Breast Cancer in Young Women: Effect of Chemotherapy on Ovarian Function, Fertility, and Birth Defects." *J. Natl. Cancer Inst. Monogr.* 16: 125-9 (1994).
Tilly "Recent Arguments Against Germ Cell Renewal in the Adult Human Ovary." *Cell Cycle*, 6:8, 879-883, (2007).
Veitia et al, "Recovery of Female Fertility After Chemotherapy, Irradiation, and Bone Marrow Allograft: Further Evidence Against Massive Oocyte Regeneration by Bone Marrow-Derived Germline Stem Cells." *Stem Cells*, DOI: 10.1634/stemcells.2006-0770 (2007).
Lee et al. "Bone Marrow Transplantation Generates Immature Oocytes and Rescues Long-Term Fertility in a Preclinical Mouse Model of Chemotherapy-Induced Premature Ovarian Failure."*J Clin Oncol.*; 25: 3198-3204 (2007).
Liu et al., "Germline stem cells and neo-oogenesis in the adult human ovary." *Dev. Biol.* (DOI:10.1016./j.ydbio.2007.03.006 (2007).
Gougeon et al. "Regulation of Ovarian Follicular Development in Primates: Facts and Hypotheses." *Endocr Rev.* 17: 121-55 (1996).
Zuckerman "The Number Of Oocytes in the mature Ovary." *Recent Prog. Horm. Res.* 6: 63-108 (1951).
Perez et al. *Nature Genetics* 21:200-203 (1999).
Fujiwara, et al., Isolation of a DEAD—family protein gene that encodes a murine homolog of *Drosophila vasa* and its specific expression in germ cell lineage, Proc. Natl. Acad. Sci. USA, vol. 91, pp. 12258-12262, Dec. 1994.
Pacchiarotti, et al., Differentiation Potential of Germ Line Stem Cells Derived from the Postnatal Mouse Ovary, International Society of Differentiation (2010), doi: 10.1016/j.diff.2010.01.001.
Ghadami et al., Intravenously Injected Bone Marrow Cells Restore Ovarian Folliculogenesis and Steroid Hormones Production in Female FSHE (-1-) Mice. Reproductive Sciences, 15(1) (Supplement)—Abstract No. 597, Jan. 2008.
Virant-Klun, et al., Putative Stem Cells with an Embryonic Character Isolated from the Ovarian Surface Epithelium of Women with no Naturally Present Follicles and Oocytes. Differentiation, pp. 1-14, DOI: 10.111/j. 1432-0436.2008.00268.x Feb. 2008.
Webster's Ninth New Collegiate Dictionary, Merriam-Webster Inc., 2000, Springfield, MA (web excerpt—definition of "correspond").
Noce et al., Vasa homolog genes in mammalian germ cell development. Cell Struct Funct 26:131-136, 2001.
K. Zou, et al., "Production of Offspring from a Germline Stem Cell Line Derived from Neonatal Ovaries" Nature Cell Biology Advance Online Publication DOI:1038/ncb 1869: 1-20 (Apr. 12, 2009).
Zuckerman, Recent Prog Horm Res 1951; 6:63-108.

Johnson et al., Nature 2004; 428:145-150.
Spradling, *Nature* 2004 428:133-134.
Zou et al., Nat Cell Biol 2009: 11:631-636.
Johnson et al., Cell 2005; 122:303-315.
Wang et al., Cell Cycle 2010; 9:339-349.
Niikura et al., Aging 2010; 2:999-1003.
Tilly et al., Biol Reprod 2009; 80:2-12.
Tilly et al., Mol Hum Reprod 2009; 15:393-398.
Niikura et al., Aging 2009; 1:971-978.
Massasa et al., Aging 2010; 2:1-2.
Ventura *Vital Health Stat* 47:1-27, 1989.
Matthews NCHS Data Brief 21:1-8, 2009.
Yang et al., ScienceDirect, Experimental Gerontology 41 (2006) 718-726.
Henderson et al., *Nature* 218:22-28, 1968.
Hassold et al., *Hum Genet* 70:11-17, 1985.
Battaglia et al., *Hum Reprod* 11:2217-2222, 1996.
Hunt et al., *Trends Genet* 24:86-93, 2008.
Tarín et al., *Mol Reprod Dev* 61 :385-397, 2002.
Tarín et al., *Theriogenology* 57:1539-1550, 2002.
Bentov et al., Fertil Steril 2010; 93(1):272-5. Epub Sep. 2009.
Bartmann et al., J Assist Reprod Genet 2004; 21:79-83.
Wilding et al., Zygote 2005; 13:317-23.
Zhang et al., *Cell Res* 16:841-850, 2006.
Van Blerkom et al., *Hum Reprod* 10:415-424, 1995.
Cohen et al., Mol Hum Reprod 1998; 4:269-80.
Barritt et al., Hum Reprod 2001; 16:513-6.
Muggleton-Harris et al., Nature 1982; 229:460-2.
Harvey et al., Curr Top Dev Biol 2007; 77:229-49.
Sutovsky et al., *Biol Reprod* 63:5820590, 2000.
Acton et al., Biol Reprod 2007; 77: 569-76.
Sponsers / Researchers—Human Cells Used in Therapy Involving the Transfer of Genetic Material by Means Other Than the Union of Gamete Nuclei (publically available from the FDA at http://www.fda.gov/BiologicsBloodVaccines/SafetyAvailability/ucm105852.htm).
Ramalho-Santos et al., *Hum Reprod Update*. 2009 (5):55 3-72.
Pachiarotti et al., *Differentiation* 2010 79:159-170.
Tarin et al., *Biol Reprod* 2001 65:141-150.
Pan et al., *Dev Biol* 2008 316:397-407.
Duncan et al., *Biol Reprod* 2009 81:768-776.
Sinclair Mech Ageing Dev 2005 26:987.
Selesniemi et al. *Aging Cell* 7:622-629, 2008.
Yang et al., Cell 2008.
Hafner et al. *Aging* 2010 2:1-10Yang et al., *Exp Gerontol* 2006 41: 718-726.
Tarín et al., *Hum Reprod* 1995 10:1563-1565.
Folstad et al., Biotechnol. Prog. 2002 18(1):1-5.
Short et al., PNAS USA, Apr. 12, 2005 102(15): 5618-5623.
Lu et al., Anal. Chem., Oct. 1, 2004 76(19): 5705-5712.
White et al.: "Oocyte formation by mitotically active germ cells purified from ovaries of reproductive-age women", Nat. Med. 2012; 18(3): 413-21.
Raetz et al.: "Somatic cell cloning in polyester stacks", Proc. Natl. Acad. Sci. U.S.A. 1982; 17(10): 3223-7.
Esko: "Replica Plating of Animal Cells", Methods Cell Biology, 1989, 32:387-422.
Liu et al.: Global amplification polymerase chain reaction reveals novel transitional stages during osteoprogenitor differentiation, J. Cell Sci., 2003, 116(Pt. 9): 1787-96.
Maher (Nature News, Making new eggs in old mice, pp. 1-4, 2012).

* cited by examiner

INTACT UNDER BURSA

BURSA REMOVED

LIGHT

GFP

LIGHT

GFP

Day 4

Day 42

Day 42

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Dmc1/ Dmc1-d3 Forward Primer

<400> SEQUENCE: 1
gaaggaggat caagttgtgc                                              20

<210> SEQ ID NO 2
<211> LENGTH: 20
<212> TYPE: DNA
<213> ORGANISM: Artificial Sequence
<220> FEATURE:
<223> OTHER INFORMATION: Dmc1/ Dmc1-d3 Reverse Primer

<400> SEQUENCE: 2
gcttcatttt caggcatctc                                              20

<210> SEQ ID NO 3
<211> LENGTH: 21
<212> TYPE: DNA
<213> ORGANISM: Artificial Sequence
<220> FEATURE:
<223> OTHER INFORMATION: L7 Forward Primer

<400> SEQUENCE: 3
ggagctcatc tatgagaagg c                                            21

<210> SEQ ID NO 4
<211> LENGTH: 21
<212> TYPE: DNA
<213> ORGANISM: Artificial Sequence
<220> FEATURE:
<223> OTHER INFORMATION: L7 Reverse Primer

<400> SEQUENCE: 4
aagacgaagg agctgcagaa c                                            21

<210> SEQ ID NO 5
<211> LENGTH: 21
<212> TYPE: DNA
<213> ORGANISM: Artificial Sequence
<220> FEATURE:
<223> OTHER INFORMATION: Scp3 Forward Primer

<400> SEQUENCE: 5
gagccgctga gcaaacatct a                                            21
```

```
<210> SEQ ID NO 6
<211> LENGTH: 21
<212> TYPE: DNA
<213> ORGANISM: Artificial Sequence
<220> FEATURE:
<223> OTHER INFORMATION: Scp3 Reverse Primer

<400> SEQUENCE: 6
atatccagtt cccactgctg c                                              21

<210> SEQ ID NO 7
<211> LENGTH: 20
<212> TYPE: DNA
<213> ORGANISM: Artificial Sequence
<220> FEATURE:
<223> OTHER INFORMATION: Spo11a,b Forward Primer

<400> SEQUENCE: 7
ccgaggcctc gttcttcgac                                                20

<210> SEQ ID NO 8
<211> LENGTH: 20
<212> TYPE: DNA
<213> ORGANISM: Artificial Sequence
<220> FEATURE:
<223> OTHER INFORMATION: Spo11a,b Reverse Primer

<400> SEQUENCE: 8
tgtccaccgc agcctggttc                                                20

<210> SEQ ID NO 9
<211> LENGTH: 18
<212> TYPE: DNA
<213> ORGANISM: Artificial Sequence
<220> FEATURE:
<223> OTHER INFORMATION: Mili Forward Primer

<400> SEQUENCE: 9
tggtactcga gggtggtg                                                  18

<210> SEQ ID NO 10
<211> LENGTH: 18
<212> TYPE: DNA
<213> ORGANISM: Artificial Sequence
<220> FEATURE:
<223> OTHER INFORMATION: Mili Reverse Primer

<400> SEQUENCE: 10
cagggctcag atttgcag                                                  18

<210> SEQ ID NO 11
<211> LENGTH: 21
<212> TYPE: DNA
<213> ORGANISM: Artificial Sequence
<220> FEATURE:
<223> OTHER INFORMATION: Nucleostemin Forward Primer

<400> SEQUENCE: 11
cacaagaagc ctaggaagga c                                              21

<210> SEQ ID NO 12
<211> LENGTH: 21
<212> TYPE: DNA
<213> ORGANISM: Artificial Sequence
<220> FEATURE:
<223> OTHER INFORMATION: Nucleostemin Reverse Primer
```

-continued

<400> SEQUENCE: 12
ctccaagaag cttccaaagg g                                          21

<210> SEQ ID NO 13
<211> LENGTH: 21
<212> TYPE: DNA
<213> ORGANISM: Artificial Sequence
<220> FEATURE:
<223> OTHER INFORMATION: Pum1 Forward Primer

<400> SEQUENCE: 13
gcagtgcttt ggcaggactc t                                          21

<210> SEQ ID NO 14
<211> LENGTH: 21
<212> TYPE: DNA
<213> ORGANISM: Artificial Sequence
<220> FEATURE:
<223> OTHER INFORMATION: Pum1 Reverse Primer

<400> SEQUENCE: 14
ggcactgtct cgccattgat c                                          21

<210> SEQ ID NO 15
<211> LENGTH: 21
<212> TYPE: DNA
<213> ORGANISM: Artificial Sequence
<220> FEATURE:
<223> OTHER INFORMATION: Pum2 Forward Primer

<400> SEQUENCE: 15
ggagagagac tgcatgggga a                                          21

<210> SEQ ID NO 16
<211> LENGTH: 21
<212> TYPE: DNA
<213> ORGANISM: Artificial Sequence
<220> FEATURE:
<223> OTHER INFORMATION: Pum2 Reverse Primer

<400> SEQUENCE: 16
gcgacttcca ggagtgcgat t                                          21

<210> SEQ ID NO 17
<211> LENGTH: 21
<212> TYPE: DNA
<213> ORGANISM: Artificial Sequence
<220> FEATURE:
<223> OTHER INFORMATION: Dazl Forward Primer

<400> SEQUENCE: 17
gtgtgtcgaa gggctatgga t                                          21

<210> SEQ ID NO 18
<211> LENGTH: 21
<212> TYPE: DNA
<213> ORGANISM: Artificial Sequence
<220> FEATURE:
<223> OTHER INFORMATION: Dazl Reverse Primer

<400> SEQUENCE: 18
acaggcagct gatatccagt g                                          21

<210> SEQ ID NO 19
<211> LENGTH: 24

```
<212> TYPE: DNA
<213> ORGANISM: Artificial Sequence
<220> FEATURE:
<223> OTHER INFORMATION: Fragilis Forward Primer

<400> SEQUENCE: 19
gttatcacca ttgttagtgt catc                                         24

<210> SEQ ID NO 20
<211> LENGTH: 21
<212> TYPE: DNA
<213> ORGANISM: Artificial Sequence
<220> FEATURE:
<223> OTHER INFORMATION: Fragilis Reverse Primer

<400> SEQUENCE: 20
aatgagtgtt acacctgcgt g                                            21

<210> SEQ ID NO 21
<211> LENGTH: 20
<212> TYPE: DNA
<213> ORGANISM: Artificial Sequence
<220> FEATURE:
<223> OTHER INFORMATION: Gdf9 Forward Primer

<400> SEQUENCE: 21
tgcctccttc cctcatcttg                                              20

<210> SEQ ID NO 22
<211> LENGTH: 20
<212> TYPE: DNA
<213> ORGANISM: Artificial Sequence
<220> FEATURE:
<223> OTHER INFORMATION: Gdf9 Reverse Primer

<400> SEQUENCE: 22
cacttccccc gctcacacag                                              20

<210> SEQ ID NO 23
<211> LENGTH: 20
<212> TYPE: DNA
<213> ORGANISM: Artificial Sequence
<220> FEATURE:
<223> OTHER INFORMATION: Hdac6 Forward Primer

<400> SEQUENCE: 23
acgctgacta cattgctgct                                              20

<210> SEQ ID NO 24
<211> LENGTH: 20
<212> TYPE: DNA
<213> ORGANISM: Artificial Sequence
<220> FEATURE:
<223> OTHER INFORMATION: Hdac6 Reverse Primer

<400> SEQUENCE: 24
tctcaactga tctctccagg                                              20

<210> SEQ ID NO 25
<211> LENGTH: 20
<212> TYPE: DNA
<213> ORGANISM: Artificial Sequence
<220> FEATURE:
<223> OTHER INFORMATION: Mvh Forward Primer

<400> SEQUENCE: 25
```

```
ggaaaccagc agcaagtgat                                          20

<210> SEQ ID NO 26
<211> LENGTH: 19
<212> TYPE: DNA
<213> ORGANISM: Artificial Sequence
<220> FEATURE:
<223> OTHER INFORMATION: Mvh Reverse Primer

<400> SEQUENCE: 26
tggagtcctc atcctctgg                                           19

<210> SEQ ID NO 27
<211> LENGTH: 21
<212> TYPE: DNA
<213> ORGANISM: Artificial Sequence
<220> FEATURE:
<223> OTHER INFORMATION: Oct4 Forward Primer

<400> SEQUENCE: 27
cccaagttgg cgtggagact t                                        21

<210> SEQ ID NO 28
<211> LENGTH: 21
<212> TYPE: DNA
<213> ORGANISM: Artificial Sequence
<220> FEATURE:
<223> OTHER INFORMATION: Oct4 Reverse Primer

<400> SEQUENCE: 28
cttctggcgc cggttacaga a                                        21

<210> SEQ ID NO 29
<211> LENGTH: 21
<212> TYPE: DNA
<213> ORGANISM: Artificial Sequence
<220> FEATURE:
<223> OTHER INFORMATION: Stella Forward Primer

<400> SEQUENCE: 29
cccaatgaag gaccctgaaa c                                        21

<210> SEQ ID NO 30
<211> LENGTH: 21
<212> TYPE: DNA
<213> ORGANISM: Artificial Sequence
<220> FEATURE:
<223> OTHER INFORMATION: Stella Reverse Primer

<400> SEQUENCE: 30
aatggctcac tgtcccgttc a                                        21

<210> SEQ ID NO 31
<211> LENGTH: 21
<212> TYPE: DNA
<213> ORGANISM: Artificial Sequence
<220> FEATURE:
<223> OTHER INFORMATION: Zp3 Forward Sequence

<400> SEQUENCE: 31
ccgagctgtg caattcccag a                                        21

<210> SEQ ID NO 32
<211> LENGTH: 21
<212> TYPE: DNA
<213> ORGANISM: Artificial Sequence
```

```
<220> FEATURE:
<223> OTHER INFORMATION: Zp3 Reverse Primer

<400> SEQUENCE: 32
aaccctctga gccaagggtg a                                              21
```

ISOLATED POPULATIONS OF FEMALE GERMLINE STEM CELLS AND CELL PREPARATIONS AND COMPOSITIONS THEREOF

CROSS-REFERENCE AND CLAIM OF PRIORITY

This application is a continuation of U.S. application Ser. No. 14/160,193, filed on Jan. 21, 2014, now abandoned, which is a division of U.S. application Ser. No. 13/090,904, filed on Apr. 20, 2011, now issued as U.S. Pat. No. 8,652,840, which is a division of U.S. application Ser. No. 11/131,114, filed on May 17, 2005, now issued as U.S. Pat. No. 7,955,846, which claims the benefit under 35 U.S.C. § 119(e) of U.S. provisional Application Ser. No. 60/572,222, filed on May 17, 2004, U.S. provisional Application Ser. No. 60/574,187, filed on May 24, 2004, and U.S. provisional Application Ser. No. 60/586,641, filed on Jul. 9, 2004, the contents of each of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF GOVERNMENT INTEREST

The United States government has certain rights in this invention by virtue of grant numbers R01-AG12279 and R01-AG24999 from the National Institute on Aging and R01-ES08430 from the National Institute of Environmental Health Science of the National Institutes of Health.

BACKGROUND OF THE INVENTION

Until recently, it was believed that female gonads of most mammalian species, including humans, house a finite number of meiotically-arrested germ cells (oocytes) enclosed within primordial follicles that serve as the stockpile of eggs released at ovulation during each menstrual cycle (Gougeon, A. et al, (1996) Endocr Rev. 17: 121-55; Morita, Y. & Tilly, J. L., (1999) Dev. Biol. 213: 1-17). Oocyte numbers decline throughout postnatal life, though mechanisms involving apoptosis (Tilly, J. L., (2001) Nat. Rev. Mol. Cell. Biol. 2: 838-848), which were widely believed to eventually leave the ovaries barren of germ cells (Faddy, M. J. et al., (1976) J. Exp. Zool. 197: 173-186; Faddy, M. J. et al., (1987) Cell Tissue Kinet. 20: 551-560; Faddy, M. J., (2000) Mol. Cell. Endocrinol. 163: 43-48). In humans, exhaustion of the oocyte reserve typically occurs during the fifth decade of life, driving menopause. (Richardson, S. J. et al. (1987) J. Clin. Endocrinol. Metab. 65: 1231-1237).

According to this basic doctrine of reproductive biology, it was further believed that once depleted, the ovarian germ cell pool could not be replenished. (Zuckerman, S. (1951) Recent Prog. Horm. Res. 6: 63-108; Borum, K., (1961) Exp. Cell Res. 24: 495-507; Peters, H., (1970) Phil. Trans. R. Soc. Lond. B, 259: 91-101; McLaren, A., (1984) Symp. Soc. Exp. Biol. 38: 7-23; Anderson, L. D. and Hirshfield, A. N. (1992) Md. Med. J. 41: 614-620). Thus, any treatment that accelerates the loss of oocytes threatens to decrease the fertility and will cause menopause at an earlier age than expected. For example, exposure of women to a wide spectrum of agents that damage the ovary, such as chemotherapeutic agents and radiotherapy, generally leads to premature menopause and irreversible sterility. At present, the limited therapeutic options of preserving fertility and normal ovarian function under various adverse conditions are invasive, such as for example cryopreservation of ovarian tissue fragments or single oocytes, and often require hormonal therapy, which can be medically inappropriate for many women with hormonally responsive tumors (Waxman, J. (1983) J. R. Soc. Med. 76: 144-8; Familiari, G. et al., (1993) Hum. Reprod. 8: 2080-7; Ried, H. L. & Jaffe, N., (1994) Semin. Roentgenol. 29: 6-14; Reichman, B. S. & Green, K. B. (1994) J. Natl. Cancer Inst. Monogr. 16: 125-9). In addition, there are currently no therapeutic options for postponing normal ovarian failure at menopause. Therefore, there is great need in the art for further discovery and development of new or less invasive therapeutic interventions for restoring failed ovarian function and infertility in women.

SUMMARY OF THE INVENTION

It has now been shown that mammalian females do not lose the capacity for germ-cell renewal during postnatal life. Mammalian ovaries possess mitotically competent female germline stem cells and female germline stem cell progenitors that, based on rates of oocyte degeneration and clearance, sustain oocyte and follicle production in the postnatal mammalian ovary.

Characterization of female germline stem cells and their progenitor cells are described herein. Accordingly, methods of the invention relate to, among other things, the use of female germline stem cells, and their progenitor cells, to expand the follicle reserve as a means of enhancing or restoring fertility in females, and for ameliorating symptoms and consequences of menopause.

In one aspect, the present invention provides compositions comprising female germline stem cells.

In one embodiment, the present invention provides compositions comprising female germline stem cells, wherein the cells are mitotically competent and express Vasa, Oct-4, Dazl, Stella and optionally, a stage-specific embryonic antigen ("SSEA"). Preferably, the SSEA is SSEA-1. Consistent with their mitotically competent phenotype, female germline stem cells of the invention do not express growth/differentiation factor-9 ("GDF-9"), zona pellucida proteins (e.g., zona pellucida protein-3, "ZP3"), histone deacetylase-6 ("HDAC6") and synaptonemal complex protein-3 ("SCP3"). Upon transplantation into a host, female germline stem cells of the invention can produce oocytes after a duration of at least 1 week, more preferably 1 to about 2 weeks, about 2 to about 3 weeks, about 3 to about 4 weeks or more than about 5 weeks post transplantation.

In another aspect, the present invention provides compositions comprising progenitor cells derived from female germline stem cells. The female germline stem cell progenitors ("progenitor cells") of the invention are present in the ovary and share common characteristics of female germline stem cells. Accordingly, in one embodiment, the present invention provides compositions comprising female germline stem cell progenitors, wherein the cells express an SSEA, Vasa, Oct-4, Dazl, and Stella, and wherein the cells do not express GDF-9, zona pellucida proteins (e.g., ZP3), HDAC6 and SCP3. Preferably, the SSEA is SSEA-1. Upon transplantation into a host, female germline stem cell progenitors of the invention can produce oocytes after a duration of less than 1 week, preferably about 24 to about 48 hours post transplantation.

In one embodiment, the present invention provides an isolated cell, wherein the cell is mitotically competent and expresses Vasa, Oct-4, Dazl, Stella and optionally, an SSEA. In a specific embodiment, the isolated cell is a female germline stem cell and in another specific embodiment, the isolated cell is a female germline stem cell progenitor that expresses SSEA. Preferably, the female germline stem cells, or their progenitor cells, are non-embryonic, mammalian, and even more preferably, human.

In another embodiment, the present invention provides purified populations of female germline stem cells and/or their progenitor cells. In specific embodiments, the purified population of cells is about 50 to about 55%, about 55 to about 60%, about 65 to about 70%, about 70 to about 75%, about 75 to about 80%, about 80 to about 85%, about 85 to about 90%, about 90 to about 95% or about 95 to about 100% of the cells in the composition.

In yet another embodiment, the present invention provides pharmaceutical compositions comprising female germline stem cells, and/or their progenitor cells, and a pharmaceutically acceptable carrier. The pharmaceutical compositions can comprise purified populations of female germline stem cells and/or their progenitor cells.

In another aspect, the present invention provides a method for the isolation of compositions comprising female germline stem cells and/or female germline stem cell progenitors, said method comprising the steps of:
 a) homogenizing ovarian tissue;
 b) contacting the tissue with an agent that binds to an SSEA; and
 c) isolating female germline stem cells and/or female germline stem cell progenitors.

Preferably, the stage-specific embryonic antigen is SSEA-1.

In one embodiment, the present invention provides a method for the isolation of female germline stem cells and/or female germline stem cell progenitors, said method comprising the steps of:
 a) sectioning ovarian tissue;
 b) labeling the perimeter of the female germline stem cells and/or female germline stem cell progenitors within the tissue with an identifying marker;
 c) applying laser pulses to the perimeter of the female germline stem cells and/or female germline stem cell progenitors; and
 d) adhering the female germline stem cells and/or female germline stem cell progenitors to a capture substrate.

Ovarian tissue can be fresh, frozen or fixed prior to sectioning. Cells can be labeled with an identifying marker using histological, immunohistochemical, or other compatible techniques to enhance the contrast between desired and undesired cell types.

In yet another aspect, the invention provides methods for manipulating female germline stem cells, or female germline stem cell progenitors, in vivo, ex vivo or in vitro as described herein below.

In one embodiment, the invention provides a method for expanding female germline stem cells, or their progenitor cells, in vivo, ex vivo or in vitro, comprising contacting female germline stem cells, or their progenitor cells, with an agent that increases the amount of female germline stem cells, or their progenitor cells, by promoting proliferation or survival thereof, thereby expanding the female germline stem cells, or their progenitor cells. In a preferred embodiment, the agent includes, but is not limited to, a hormone or growth factor (e.g., insulin-like growth factor ("IGF"), transforming growth factor ("TGF"), bone morphogenic protein ("BMP"), Wnt protein, or fibroblast growth factor ("FGF")), a cell-signaling molecule (e.g., sphingosine-1-phosphate ("S1P"), or retinoic acid ("RA")), or a pharmacological or pharmaceutical compound (e.g., an inhibitor of glycogen synthase kinase-3 ("GSK-3"), an inhibitor of apoptosis such as a Bax inhibitor or a caspase inhibitor, an inhibitor of nitric oxide production, or an inhibitor of HDAC activity).

In another embodiment, the invention provides a method for identifying an agent that promotes proliferation or survival of a female germline stem cell, or its progenitor cell, comprising contacting female germline stem cells, or their progenitor cells, with a test agent; and detecting an increase in the number of female germline stem cells, or their progenitor cells, thereby identifying an agent that promotes proliferation or survival of a female germline stem cell, or its progenitor.

In yet another embodiment, the invention provides a method for using the female germline stem cells, or their progenitor cells, to characterize pharmacogenetic cellular responses to biologic or pharmacologic agents, comprising isolating female germline stem cells, or their progenitor cells, from a population of subjects, expanding said cells in culture to establish a plurality of cell cultures, optionally differentiating said cells into a desired lineage, contacting the cell cultures with one or more biologic or pharmacologic agents, identifying one or more cellular responses to the one or more biologic or pharmacologic agents, and comparing the cellular responses of the cell cultures from different subjects.

In yet another embodiment, the invention provides a method for producing a lineage committed cell, comprising contacting a female germline stem cell, or its progenitor cell, with an agent that differentiates the female germline stem cell, or its progenitor cell into a lineage committed cell. In a preferred embodiment, the agent includes, but is not limited to, Vascular Endothelial Growth Factor, Sonic Hedgehog, Insulin-like Growth Factor II, Osteogenin, Cytotoxic T Cell Differentiation Factor, b-catenin, Bone Morphogenic Protein 2, Interleukin 2, Transforming Growth Factor b, Nerve Growth Factor, Interleukin 1, Fibroblast Growth Factor 2, Retinoic Acid and Wnt3.

In yet another embodiment, the invention provides a method for reducing the amount of female germline stem cells, or their progenitor cells, in vivo, ex vivo or in vitro, comprising contacting female germline stem cells, or their progenitor cells, with an agent that reduces cell proliferation, thereby reducing the amount of female germline stem cells, or their progenitor cells. In a preferred embodiment, the agent includes, but is not limited to, a hormone or growth factor (e.g., TGF-β), a peptide antagonist of mitogenic hormones or growth factors (e.g., the BMP antagonists, Protein Related to DAN and Cerberus ("PRDC") and Gremlin), or a pharmacological or pharmaceutical compound (e.g., a cell cycle inhibitor, or an inhibitor of growth factor signaling).

In yet another embodiment, the invention provides a method for reducing the amount of female germline stem cells, or their progenitor cells, in vivo, ex vivo or in vitro, comprising contacting female germline stem cells, or their progenitor cells, with an agent that inhibits cell survival or promotes cell death, thereby reducing the amount of female germline stem cells, or their progenitor cells. In a preferred embodiment, the agent the that inhibits cell survival includes, but is not limited to, a hormone, growth factor or cytokine (e.g., a pro-apoptotic tumor necrosis factor ("TNF") super family member such as TNF-α, Fas-ligand ("FasL") and TRAIL), an antagonist of pro-survival Bcl-2 family member function, a signaling molecule (e.g., a ceramide), or a pharmacological or pharmaceutical compound (e.g., an inhibitor of growth factor signaling). In a preferred embodiment, the agent the that promotes cell death includes, but is not limited to, a pro-apoptotic tumor necrosis factor superfamily member (e.g., TNF-α, FasL and TRAIL), agonist of pro-apoptotic Bcl-2 family member function and ceramide.

In yet another embodiment, the invention provides a method for identifying an agent that reduces proliferation or survival, or promotes cell death, of a female germline stem cell, or its progenitor cell, comprising contacting female germline stem cells, or their progenitor cells, with a test agent; and detecting a decrease in the number of female germline stem cells, or their progenitor cells, thereby identifying an agent that reduces proliferation or survival, or promotes cell death, of a female germline stem cell, or its progenitor cell.

In yet another embodiment, the invention provides a method for oocyte production, comprising culturing a female germline stem cell, or its progenitor cell, in the presence of an agent that differentiates a female germline stem cell, or its progenitor cell, into an oocyte, thereby producing an oocyte. In a preferred embodiment, the agent includes, but is not limited to, a hormone or growth factor (e.g., a TGF, BMP or Wnt family protein, kit-ligand ("SCF") or leukemia inhibitory factor ("LIF")), a signaling molecule (e.g., meiosis-activating sterol, "FF-MAS"), or a pharmacologic or pharmaceutical agent (e.g., a modulator of Id protein function or Snail/Slug transcription factor function).

In yet another embodiment, the invention provides a method for in vitro fertilization of a female subject, said method comprising the steps of:
a) producing an oocyte by culturing a female germline stem cell, or its progenitor cell, in the presence of an agent that differentiates said cell(s) into an oocyte;
b) fertilizing the oocyte in vitro to form a zygote; and
c) implanting the zygote into the uterus of a female subject.

In yet another embodiment, the invention provides a method for in vitro fertilization of a female subject, said method comprising the steps of:
a) producing an oocyte by contacting a female germline stem cell, or its progenitor cell, with an agent that differentiates said cell(s) into an oocyte;
b) fertilizing the oocyte in vitro to form a zygote; and
c) implanting the zygote into the uterus of a female subject.

In yet another embodiment, the invention provides a method for identifying an agent that induces differentiation of a female germline stem cell, or its progenitor cell, into an oocyte comprising contacting female germline stem cells, or their progenitor cells, with a test agent; and detecting an increase in the number of oocytes, thereby identifying an agent that induces differentiation of a female germline stem cell, or its progenitor.

In yet another embodiment, the present invention provides a method for oocyte production, comprising providing a female germline stem cell, or its progenitor cell, to a tissue, preferably the ovary, wherein the cell engrafts into the tissue and differentiates into an oocyte, thereby producing an oocyte.

In yet another embodiment, the present invention provides a method for inducing folliculogenesis, comprising providing a female germline stem cell, or its progenitor cell, to a tissue, preferably the ovary, wherein the cell engrafts into the tissue and differentiates into an oocyte within a follicle, thereby inducing folliculogenesis.

In yet another embodiment, the present invention provides a method for oocyte production, comprising contacting ovarian tissue with an agent that increases the amount of female germline stem cells, or their progenitor cells, by promoting proliferation or survival thereof, thereby producing oocytes. In a preferred embodiment, the agent includes, but is not limited to, a hormone or growth factor (e.g., a IGF, TGF, BMP, Wnt protein or FGF), a cell-signaling molecule (e.g., S1P or RA), or a pharmacological or pharmaceutical compound (e.g., an inhibitor of GSK-3, an inhibitor of apoptosis such as a Bax inhibitor or caspase inhibitor, an inhibitor of nitric oxide production, or an inhibitor of HDAC activity).

In yet another embodiment, the invention provides a method for identifying an agent that promotes proliferation or survival of a female germline stem cell, or its progenitor cell, comprising contacting ovarian tissue with a test agent; and detecting an increase in the number of female germline stem cells, or their progenitor cells, thereby identifying an agent that promotes proliferation or survival of a female germline stem cell, or its progenitor cell.

In yet another embodiment, the present invention provides a method for oocyte production, comprising contacting ovarian tissue with an agent that differentiates female germline stem cells, or their progenitor cells, into oocytes, thereby producing oocytes. In a preferred embodiment, the agent can be, but is not limited to, a hormone or growth factor (e.g., a TGF, BMP, Wnt family protein, SCF or LIF) or a pharmacologic or pharmaceutical agent (e.g., a modulator of Id protein function or Snail/Slug transcription factor function).

In yet another embodiment, the invention provides a method for identifying an agent that induces differentiation of a female germline stem cell, or its progenitor cell, into an oocyte comprising contacting ovarian tissue with a test agent; and detecting an increase in the number of oocytes in the ovarian tissue, thereby identifying an agent that induces differentiation of a female germline stem cell, or its progenitor cell.

In yet another embodiment, the present invention provides a method for treating infertility in a female subject in need thereof comprising administering a therapeutically effective amount of a composition comprising female germline stem cells, or their progenitor cells, to the subject, wherein the cells engraft into a tissue, preferably ovarian tissue, and differentiate into oocytes, thereby treating infertility.

In yet another embodiment, the present invention provides a method for treating infertility in a female subject in need thereof comprising contacting ovarian tissue of the subject with an agent that increases the amount of female germline stem cells, or their progenitor cells, by promoting proliferation or survival thereof, thereby treating infertility in the subject.

In yet another embodiment, the present invention provides a method for treating infertility in a female subject in need thereof comprising contacting ovarian tissue of the subject with an agent that differentiates female germline stem cells, or their progenitor cells, into oocytes, thereby treating infertility in the subject.

In yet another embodiment, the present invention provides a method for repairing damaged ovarian tissue, comprising providing a therapeutically effective amount of a composition comprising female germline stem cells, or their progenitor cells, to the tissue, wherein the cells engraft into the tissue and differentiate into oocytes, thereby repairing the damaged tissue. Damage can be caused, for example, by exposure to cytotoxic factors, chemotherapeutic drugs, radiation, hormone deprivation, growth factor deprivation, cytokine deprivation, cell receptor antibodies, and the like. Chemotherapeutic drugs include, but are not limited to, busulfan cyclophosphamide, 5-FU, vinblastine, actinomycin D, etoposide, cisplatin, methotrexate, doxorubicin, among others. Damage can also be caused be diseases that affect ovarian function, including, but not limited to cancer, polycystic ovary disease, genetic disorders, immune disorders, metabolic disorders, and the like.

In yet another embodiment, the present invention provides a method for restoring ovarian function in a menopausal female subject, comprising administering a therapeutically effective amount of a composition comprising female germline stem cells, or their progenitor cells, to the subject, wherein the cells engraft into the ovary and differentiate into oocytes, thereby restoring ovarian function. The menopausal female subject can be in a stage of either peri- or post-menopause, with said menopause caused by either normal (e.g., aging) or pathological (e.g., surgery, disease, ovarian damage) processes.

In yet another embodiment, the present invention provides a method for restoring ovarian function in a post-menopausal female subject comprising contacting ovarian tissue of the subject with an agent that increases the amount of female germline stem cells or their progenitor cells, by promoting proliferation or survival thereof, thereby restoring ovarian function in the subject.

In yet another embodiment, the present invention provides a method for restoring ovarian function in a post-menopausal female subject comprising contacting ovarian tissue of the subject with an agent that differentiates female germline stem cells, or their progenitor cells, into oocytes, thereby restoring ovarian function in the subject.

Restoration of ovarian function can relieve adverse symptoms and complications associated with menopausal disorders, including, but not limited to, somatic disorders such as osteoporosis, cardiovascular disease, somatic sexual dysfunction, hot flashes, vaginal drying, sleep disorders, depression, irritability, loss of libido, hormone imbalances, and the like, as well as cognitive disorders, such as loss of memory; emotional disorders, depression, and the like.

In yet another embodiment, the present invention provides a method for contraception in a female subject comprising contacting ovarian tissue of the subject with an agent that decreases the proliferation, function or survival of female germline stem cells, or their progenitor cells, or the ability of said cells to produce new oocytes or other somatic cell types required for fertility, thereby providing contraception to the subject.

In yet another aspect, the present invention provides kits for use in employing various agents of the invention.

In one embodiment, the present invention provides a kit for expanding a female germline stem cell, or its progenitor cell, in vivo, ex vivo or in vitro, comprising an agent that promotes cell proliferation or survival of the female germline stem cell, or its progenitor cell, and instructions for using the agent to promote cell proliferation or survival of the female germline stem cell, or its progenitor, thereby expanding a female germline stem cell, or its progenitor cell in accordance with the methods of the invention.

In another embodiment, the present invention provides a kit for reducing the amount of female germline stem cells, or their progenitor cells, in vivo, ex vivo or in vitro, comprising an agent that inhibits cell survival or promotes cell death and instructions for using the agent to inhibit cell survival or promote cell death of the female germline stem cells, or their progenitor cells, thereby the reducing the amount of female germline stem cells, or their progenitor cells, in accordance with the methods of the invention.

In yet another embodiment, the present invention provides a kit for oocyte production, comprising an agent that differentiates a female germline stem cell, or its progenitor cell, into an oocyte and instructions for using the agent to differentiate a female germline stem cell, or its progenitor cell, into an oocyte in accordance with the methods of the invention.

In yet another embodiment, the present invention provides a kit for oocyte production, comprising an agent that increases the amount of female germline stem cells, or their progenitor cells, by promoting proliferation or survival thereof, and instructions for using the agent to increase the amount of female germline stem cells or their progenitor cells, thereby producing oocytes in accordance with the methods of the invention.

In yet another embodiment, the present invention provides a kit for oocyte production comprising an agent that differentiates female germline stem cells, or their progenitor cells, into oocytes and instructions for using the agent to differentiate the female germline stem cells, or their progenitor cells, into oocytes, thereby producing oocytes in accordance with the methods of the invention.

In yet another embodiment, the present invention provides a kit for treating infertility in a female subject in need thereof comprising an agent that increases the amount of female germline stem cells, or their progenitor cells, by promoting proliferation or survival thereof and instructions for using the agent to increase the amount of female germline stem cells or their progenitor cells, thereby treating infertility in the subject in accordance with the methods of the invention.

In yet another embodiment, the present invention provides a kit for treating infertility in a female subject in need thereof comprising an agent that differentiates female germline stem cells, or their progenitor cells, into oocytes, and instructions for using the agent to differentiate female germline stem cells, or their progenitor cells, into oocytes, thereby treating infertility in the subject in accordance with the methods of the invention.

In yet another embodiment, the present invention provides a kit for restoring ovarian function in a post-menopausal female subject comprising an agent that increases the amount of female germline stem cells, or their progenitor cells, by promoting proliferation or survival thereof and instructions for using the agent to increase the amount of female germline stem cells or their progenitor cells, thereby restoring ovarian function in the subject in accordance with the methods of the invention.

In yet another embodiment, the present invention provides a kit for restoring ovarian function in a post-menopausal female subject comprising an agent that differentiates female germline stem cells, or their progenitor cells, into oocytes, and instructions for using the agent to differentiate female germline stem cells, or their progenitor cells, into oocytes, thereby restoring ovarian function in the subject in accordance with the methods of the invention.

In yet another embodiment, the present invention provides a kit for contraception in a female subject comprising an agent that decreases the proliferation, function or survival of female germline stem cells, or their progenitor cells, or the ability of said cells to produce new oocytes or other somatic cell types required for fertility and instructions for using the agent to decrease the proliferation, function or survival of female germline stem cells, or their progenitor cells, or the ability of said cells to produce new oocytes or other somatic cell types required for fertility, thereby providing contraception to the subject in accordance with the methods of the invention.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of necessary fees.

FIG. 1A shows the numbers of non-atretic follicles, while

(FIG. 9A) Antral follicle in grafted ovarian tissue containing a GFP-positive oocyte enclosed within GFP-negative granulosa cells. (FIG. 9B) Primary follicle in grafted ovarian tissue containing a GFP-positive oocyte enclosed within GFP-negative granulosa cells (broken white line).

FIG. 11A, during early postnatal life (Day 4 postpartum); and FIG. 11B and FIG. 11C, early reproductive adulthood (Day 42 postpartum).

FIG. 12A, during early postnatal life (Day 4 postpartum); and FIG. 12B and FIG. 12C, early reproductive adulthood (Day 42 postpartum).

FIG. 14A and FIG. 14C, ovaries from different mice; FIG. 14D single SSEA1+ cell in an adult ovary, showing cell surface expression of the antigen).

DETAILED DESCRIPTION OF THE INVENTION

Definitions

Figure 1A:
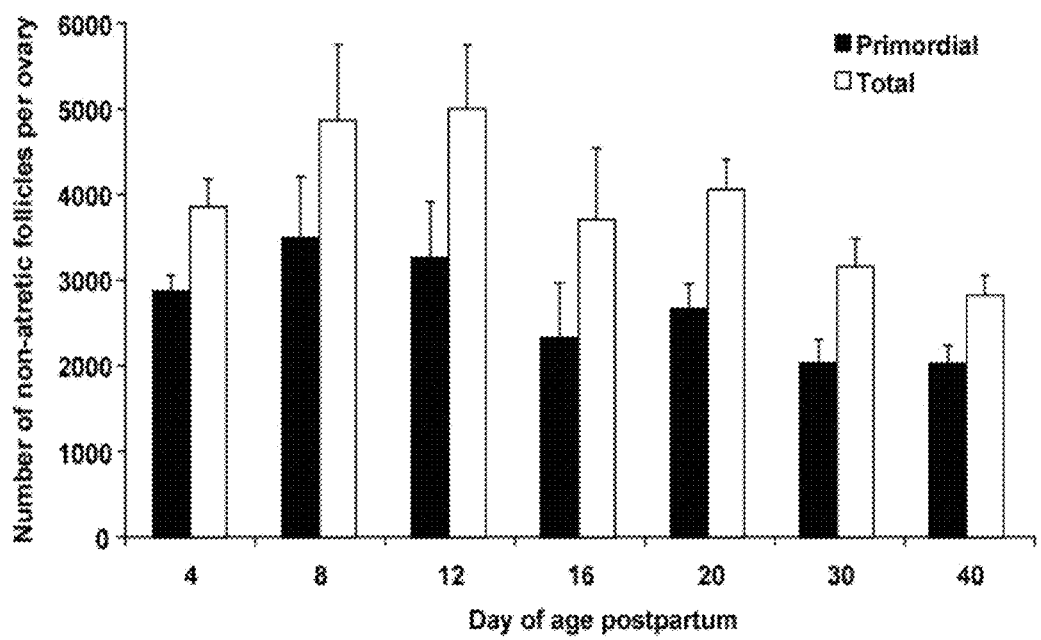

"Expansion" refers to the propagation of a cell or cells without terminal differentiation. "Isolation phenotype" refers to the structural and functional characteristics of the female germline stem cells or their progenitor cells upon isolation. "Expansion phenotype" refers to the structural and functional characteristics of the female germline stem cells or their progenitor cells during expansion. The expansion phenotype can be identical to the isolation phenotype, or alternatively, the expansion phenotype can be more differentiated than the isolation phenotype.

"Differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). Oocytes are an example of a terminally differentiated cell type.

The term "isolated" as used herein refers to a female germline stem cell or its progenitor cell, in a non-naturally occurring state (e.g., isolated from the body or a biological sample from the body). The biological sample can include bone marrow, peripheral blood, ovary or spleen.

"Progenitor cells" as used herein are germ lineage cells that are 1) derived from female germline stem cells as the progeny thereof which contain a set of common marker genes; 2) are in an early stage of differentiation; and 3) retain mitotic capacity.

"Progeny" as used herein are all daughter cells derived from female germline stem cells of the invention, including progenitor cells, differentiated cells, and terminally differentiated cells.

"Derived from" as used herein refers to the process of obtaining a daughter cell.

"Engraft" refers to the process of cellular contact and incorporation into an existing tissue of interest (e.g., ovary) in vivo.

"Agents" refer to cellular (e.g., biologic) and pharmaceutical factors, preferably growth factors, cytokines, hormones or small molecules, or to genetically-encoded products that modulate cell function (e.g., induce lineage commitment, increase expansion, inhibit or promote cell growth and survival). For example, "expansion agents" are agents that increase proliferation and/or survival of female germline stem cells or their progenitor cells. "Differentiation agents" are agents that induce female germline stem cells or their progenitor cells to differentiate into committed cell lineages, such as oocytes.

A "follicle" refers to an ovarian structure consisting of a single oocyte surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase. For reviews on ovarian structure, function and physiology, see Gougeon, A., (1996) Endocr Rev. 17:121-55; Anderson, L. D., and Hirshfield, A. N. (1992) Md Med J. 41: 614-20; and Hirshfield, A. N. (1991) Int Rev Cytol. 124: 43-101.

"Mitotically competent" refers to a cell that is capable of mitosis, the process by which a cell divides and produces two daughter cells from a single parent cell.

A "non-embryonic" cell refers to a cell that is obtained from a post-natal source (e.g., infant, child or adult tissue).

A "subject" is a vertebrate, preferably a mammal, more preferably a primate and most preferably a human. Mammals include, but are not limited to, primates, humans, farm animals, sport animals, and pets.

The term "obtaining" as in "obtaining the agent" is intended to include purchasing, synthesizing or otherwise acquiring the agent (or indicated substance or material).

The terms "comprises", "comprising", and the like are intended to have the broad meaning ascribed to them in U.S. Patent Law and can mean "includes", "including" and the like.

Embodiments of the Invention

The present invention provides compositions comprising female germline stem cells and female germline stem cell progenitors.

Female germline stem cells express markers including Vasa, Oct-4, Dazl, Stella and optionally an SSEA. Female germline stem cells are mitotically competent (i.e., capable of mitosis) and accordingly, do not express growth/differentiation factor-9 ("GDF-9"), zona pellucida proteins (e.g., zona pellucida protein-3, "ZP3"), histone deacetylase-6 ("HDAC6") or synaptonemal complex protein-3 ("SCP3"). For additional details, see, U.S. application Ser. No. 11/131,153, filed on May 17, 2005 and published on Jan. 12, 2006 as US2006/0010509 A1, and Ser. No. 11/131,152, filed on May 17, 2005 and published on Jan. 19, 2006 as US2006/0015961 A1, the contents of which are incorporated herein by reference for their description of female germline stem cells in the bone marrow and peripheral blood.

The present invention also provides progenitor cells derived from female germline stem cells. Female germline stem cell progenitors of the invention can circulate throughout the body and most preferably can be localized in bone marrow, peripheral blood and ovary. Progenitor cells of the invention express an SSEA, Oct-4, Vasa, Dazl and Stella but do not express HDAC6, GDF-9, and zona pellucida proteins (e.g., ZP3) or SCP3. Preferably, the SSEA is SSEA-1.

Female germline stem cells and female germline stem cell progenitors of the invention have functional distinctions. Upon transplantation into a host, female germline stem cells of the invention can produce oocytes after a duration of at least 1 week, more preferably 1 to about 2 weeks, about 2 to about 3 weeks, about 3 to about 4 weeks or more than about 5 weeks post transplantation. Female germline stem cell progenitors have the capacity to generate oocytes more rapidly than female germline stem cells. Upon transplantation into a host, female germline stem cell progenitors of the invention can produce oocytes after a duration of less than 1 week, preferably about 24 to about 48 hours post transplantation. For additional details, see, U.S. application Ser. No. 11/131,151, filed on May 17, 2005 and published on Jan. 12, 2006 as US2006/0010509 A1, the contents of which are incorporated herein by reference for their description of post transplantation oocyte production.

Oct-4 is a gene expressed in female germline stem cells and their progenitor cells. The Oct-4 gene encodes a transcription factor that is involved in the establishment of the mammalian germline and plays a significant role in early germ cell specification (reviewed in Scholer (1991), Trends Genet. 7(10): 323-329). In the developing mammalian embryo, Oct-4 is down-regulated during the differentiation of the epiblast, eventually becoming confined to the germ cell lineage. In the germline, Oct-4 expression is regulated separately from epiblast expression. Expression of Oct-4 is a phenotypic marker of totipotency (Yeom et al. (1996), Development 122: 881-888).

Stella is a gene expressed in female germline stem cells and their progenitor cells. Stella is a novel gene specifically expressed in primordial germ cells and their descendants, including oocytes (Bortvin et al. (2004) BMC Developmental Biology 4(2):1-5). Stella encodes a protein with a SAP-like domain and a splicing factor motif-like structure. Embryos deficient in Stella expression are compromised in preimplantation development and rarely reach the blastocyst stage. Thus, Stella is a maternal factor implicated in early embryogenesis.

Dazl is a gene expressed in female germline stem cells and their progenitor cells. The autosomal gene Dazl is a member of a family of genes that contain a consensus RNA binding domain and are expressed in germ cells. Loss of expression of an intact Dazl protein in mice is associated with failure of germ cells to complete meiotic prophase. Specifically, in female mice null for Dazl, loss of germ cells occurs during fetal life at a time coincident with progression of germ cells through meiotic prophase. In male mice null for Dazl, germ cells were unable to progress beyond the leptotene stage of meiotic prophase I. Thus, in the absence of Dazl, progression through meiotic prophase is interrupted (Saunders et al. (2003), Reproduction, 126:589-597).

Vasa is a gene expressed in female germline stem cells and their progenitor cells. Vasa is a component of the germplasm that encodes a DEAD-family (SEQ ID NO: 1) ATP-dependent RNA helicase (Liang et al. (1994) Development, 120:1201-1211; Lasko et al. (1988) Nature, 335: 611-167). The molecular function of Vasa is directed to binding target mRNAs involved in germ cell establishment (e.g., Oskar and Nanos), oogenesis, (e.g., Gruken), and translation onset (Gavis et al. (1996) Development, 110: 521-528). Vasa is required for pole cell formation and is exclusively restricted to the germ cell lineage throughout the development. Thus, Vasa is a molecular marker for the germ cell lineage in most animal species (Toshiaki et al. (2001) Cell Structure and Function 26:131-136).

Stage-Specific Embryonic Antigens are optionally expressed in female germline stem cells and expressed in female germline stem cell progenitors of the invention. Stage-Specific Embryonic Antigen-1 (SSEA-1) is a cell surface embryonic antigen whose functions are associated with cell adhesion, migration and differentiation. During hypoblast formation, SSEA-1 positive cells can be identified in the blastocoel and hypoblast and later in the germinal crescent. SSEA-1 functions in the early germ cell and neural cell development. (D'Costa et al. (1999) Int J. Dev. Biol. 43(4): 349-356; Henderson et al. (2002) Stem Cells 20: 329-337). In specific embodiments, expression of SSEAs in female germline stem cells may arise as the cells differentiate.

Female germline stem cells and their progenitor cells do not express GDF-9, a gene expressed in cells that have already started to differentiate into oocytes. Growth/differentiation factor-9 (GDF-9) is a member of the transforming growth factor-β superfamily, highly expressed in ovaries. GDF-9 mRNA can be found in neonatal and adult oocytes from the primary one-layer follicle stage until after ovulation (Dong, J. et al (1996) Nature 383: 531-5). Analysis of GDF-9 deficient mice reveals that only primordial and primary one-layer follicles can be formed, but a block beyond the primary one-layer follicle stage in follicular development occurs, resulting in complete infertility.

Female germline stem cells and their progenitor cells do not express ZP1, ZP2, and ZP3, which are gene products that comprise the zona pellucida (ZP) of the oocyte. Their expression is regulated by a basic helix-loop-helix (bHLH) transcription factor, FIGα. Mice null in FIGα do not express the Zp genes and do not form primordial follicles (Soyal, S. M., et al (2000) Development 127: 4645-4654). Individual knockouts of the ZP genes result in abnormal or absent zonae pellucidae and decreased fertility (ZP1; Rankin T, et al (1999) Development. 126: 3847-55) or sterility (ZP2, Rankin T L, et al. (2001) Development 128: 1119-26; ZP3, Rankin T et al (1996) Development 122: 2903-10). The ZP protein products are glycosylated, and subsequently secreted to form an extracellular matrix, which is important for in vivo fertilization and pre-implantation development. Expression of the ZP proteins is precisely regulated and restricted to a two-week growth phase of oogenesis. ZP mRNA transcripts are not expressed in resting oocytes, however once the oocytes begin to grow, all three ZP transcripts begin to accumulate.

Figure 16:
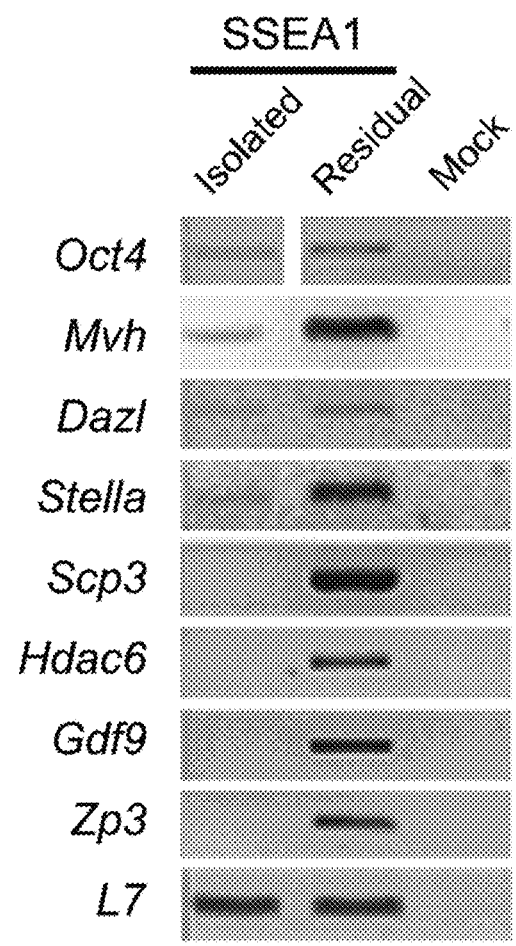
FIG. 16 depicts the SSEA-1 isolated (immunopurified) fraction representing a population of cells expressing genes that denote pluripotency (SSEA-1, Oct-4) and places their lineage within the germline (Dazl, Stella, Mvh/Vasa) but lacking genes expressed in germ cells undergoing meiosis (SCP3) or in oocytes (GDF9, ZP3, HDAC6). The residual ovarian tissue contains growing oocytes and resting primordial oocytes, and thus all marker genes are expressed in this fraction.

Female germline stem cells and their progenitor cells do not express HDAC6. HDACs, or histone deacetylases are involved in ovarian follicle development. HDAC6 in particular can be detected in resting germinal vesicle-stage (primordial) oocytes (Verdel, A., et al. (2003) Zygote 11: 323-8; FIG. 16). HDAC6 is a class II histone deacetylase and has been implicated as a microtubule-associated deactylase (Hubbert, C. et al, (2002) Nature 417: 455-8). HDACs are the target of inhibitors including, but not limited to, trichostatin A and trapoxin, both of which are microbial metabolites that induce cell differentiation, cell cycle arrest, and reversal of the transformed cell morphology.

Female germline stem cells and their progenitor cells do not express SCP3, consistent with observations that they are pre-meiotic stem cells (i.e., diploid). The synaptonemal complex protein SCP3 is part of the lateral element of the synaptonemal complex, a meiosis-specific protein structure essential for synapsis of homologous chromosomes. The synaptonemal complex promotes pairing and segregation of homologous chromosomes, influences the number and relative distribution of crossovers, and converts crossovers into chiasmata. SCP3 is meiosis-specific and can form multi-stranded, cross-striated fibers, forming an ordered, fibrous core in the lateral element (Yuan, L. et al, (1998) J. Cell. Biol. 142: 331-339). The absence of SCP3 in mice can lead to female germ cell aneuploidy and embryo death, possibly due to a defect in structural integrity of meiotic chromosomes (Yuan, L. et al, (2002) Science 296: 1115-8).

Female germline stem cells and their progenitor cells can be isolated from ovarian homogenate using immuno-affinity separation with the Stage-Specific Embryonic Antigen-1 antibody ("anti-SSEA-1") (commercially available, for example, from Chemicon (MAB4301)).

Methods of antibody based separation and isolation generally known in the art can be employed to obtain SSEA-1 positive germ cells from ovarian homogenate. In one embodiment, magnetic beads can be used in the separation procedure. For example, the CELLection biotin binder kit and magnetic device from Dynal Biotech can be used to isolate the SSEA-1 positive cells. Biotinylated anti-SSEA-1 antibodies can be attached to coated magnetic beads and combined with cellular homogenate, the combination of which is subsequently fractionated by magnetic separation. Post-isolation, the affinity beads can be removed. Aliquots of isolated cells can additionally be collected and separated by flow cytometry. Multi-step cell isolation techniques can maximize the preparation of live cells for subsequent culture and manipulation, freezing, and/or transplantation.

Germline stem cell and their progenitors can also be isolated from ovarian homogenate using laser-capture microdissection. Using this technique, female germline stem cells are obtained from sectioned ovarian tissue. Ovarian tissue can be fresh, frozen or fixed prior to sectioning. Laser-capture microdis section is then carried out to isolate the female germline stem cells. The procedure of laser capture microdissection is well known in the art, see, for example, Eltoum I A et al., (2002) Adv. Anat. Pathol. 9: 316-322).

Laser capture microdis section makes use of a laser pulsing apparatus in conjunction with a specially-adapted microscope and real-time visualization computer system. First, target cells or cell types within a heterogeneous tissue section on a histological slide are identified and "marked" by labeling their perimeter via a computer interface. These cells may have been specifically labeled using histological, immunohistochemical, or other compatible techniques to enhance the contrast between desired and undesired cell types. Laser pulses are then applied to the perimeter of the cells to be captured as specified. Laser pulsing most often results in the adherence of desired, "marked" cells to a proprietary capture substrate, while undesired cells are excluded and remain attached to the histological slide. Cells attached to the capture substrate are then processed for downstream analyses, (e.g., analysis of gene expression in specific cell types within a tissue).

Female germline stem cells and their progenitor cells can be isolated by standard means known in the art for the separation of stem cells from the blood and marrow (e.g., cell sorting). Preferably, the isolation protocol includes generation of a kit$^+$/lin$^-$ fraction that is depleted of hematopoietic cells. Additional selection means based on the unique profile of gene expression (e.g., Vasa, Oct-4, Dazl, and Stella) can be employed to further purify populations of cells comprising female germline stem cells and their progenitor cells. Compositions comprising female germline stem cells and their progenitor cells can be isolated and subsequently purified to an extent where they become substantially free of the biological sample from which they were obtained (e.g. bone marrow, peripheral blood, ovary).

Female germline stem cell progenitors can be obtained from female germline stem cells by, for example, expansion in culture. Thus, the progenitor cells can be cells having an "expansion phenotype."

I. Administration

The present invention provides compositions comprising female germline stem cells, or progenitor cells derived from female germline stem cells. The compositions can be pharmaceutical compositions comprising female germline stem cells, or progenitor cells derived from female germline stem cells and a pharmaceutically acceptable carrier.

Compositions of female germline stem cells, or progenitors derived from female germline stem cells, can be provided directly to a tissue, such as ovarian tissue. Following transplantation or implantation, the cells can engraft and differentiate into oocytes. "Engraft" refers to the process of cellular contact and incorporation into an existing tissue of interest (e.g., ovary) in vivo. Expansion and differentiation agents can be provided prior to, during or after administration to increase the amount of oocytes in vivo.

Administration can be autologous or heterologous (i.e., allogenic). For example, female germline stem cells, or progenitors derived from female germline stem cells, can be obtained from one subject, and administered to the same or a different subject.

Preferably, the engrafted cells undergo oogenesis followed by folliculogenesis, wherein the cells differentiate into an oocyte within a follicle. Folliculogenesis is a process in which an ovarian structure consisting of a single oocyte is surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase.

Germline stem cells of the invention or their progeny (e.g., progenitors, differentiated progeny and terminally differentiated progeny) can be administered via localized injection, including catheter administration, systemic injection, localized injection, intravenous injection, intrauterine injection or parenteral administration. When administering a therapeutic composition of the present invention (e.g., a pharmaceutical composition), it will generally be formulated in a unit dosage injectable form (solution, suspension, emulsion).

Compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the germline stem cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

A method to potentially increase cell survival when introducing the cells into a subject in need thereof is to incorporate germline stem cells or their progeny (e.g., in vivo, ex vivo or in vitro derived) of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included expansion or differentiation factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Those skilled in the art will recognize that the components of the compositions should be selected to be chemically inert and will not affect the viability or efficacy of the germline stem cells or their progenitors as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of germline stem cells and their progeny is the quantity of cells necessary to achieve an optimal effect. In current human studies of autologous mononuclear bone marrow cells, empirical doses ranging from 1 to $4 \times 10^7$ cells have been used with encouraging results. However, different scenarios may require optimization of the amount of cells injected into a tissue of interest, such as ovarian tissue. Thus, the quantity of cells to be administered will vary for the subject being treated. Preferably, between $10^2$ to $10^6$, more preferably $10^3$ to $10^5$, and still more preferably, $10^4$ stem cells can be administered to a human subject. However, the precise determination of what would be considered an effective dose may be based on factors individual to each patient, including their size, age, sex, weight, and condition of the particular patient. As few as 100-1000 cells can be administered for certain desired applications among selected patients. Therefore, dosages can be readily ascertained by those skilled in the art from this disclosure and the knowledge in the art.

Another consideration regarding the use of germline stem cells or their progenitors is the purity of the population. Ovarian cells, for example, comprise mixed populations of cells, which can be purified to a degree sufficient to produce a desired effect. Those skilled in the art can readily determine the percentage of germline stem cells or their progenitors in a population using various well-known methods, such as fluorescence activated cell sorting (FACS). Preferable ranges of purity in populations comprising germline stem cells or their progenitors are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Purity of the germline stem cells or their progenitors can be determined according to the genetic marker marker profile within a population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

II. Germline Stem Cell Modulation and Oocyte Production

The present invention provides methods for oocyte production, in vivo, in vitro and ex-vivo. Oocyte production can be increased by increasing the number of female germline stem cells, or progenitors derived from female germline stem cells. The number of female germline stem cells, or progenitors derived from female germline stem cells can be increased by increasing the survival or proliferation of existing female germline stem cells, or progenitors derived from female germline stem cells.

Agents (e.g., expansion agents) which increase proliferation or survival of female germline stem cells, or progenitors derived from female germline stem cells include, but are not limited to, a hormone or growth factor (e.g., a IGF, TGF, BMP, Wnt protein or FGF), a cell-signaling molecule (e.g., S1P or RA), or a pharmacological or pharmaceutical compound (e.g., an inhibitor of GSK-3, an inhibitor of apoptosis such as a Bax inhibitor or caspase inhibitor, an inhibitor of nitric oxide production, or an inhibitor of HDAC activity).

Agents comprising growth factors are known in the art to increase proliferation or survival of stem cells. For example, U.S. Pat. Nos. 5,750,376 and 5,851,832 describe methods for the in vitro culture and proliferation of neural stem cells using TGF. An active role in the expansion and proliferaion of stem cells has also been described for BMPs (Zhu, G. et al, (1999) Dev. Biol. 215: 118-29 and Kawase, E. et al, (2001) Development 131: 1365) and Wnt proteins (Pazianos, G. et al, (2003) Biotechniques 35: 1240 and Constantinescu, S. (2003) J. Cell Mol. Med. 7: 103). U.S. Pat. Nos. 5,453,357 and 5,851,832 describe proliferative stem cell culture systems that utilize FGFs. The contents of each of these references are specifically incorporated herein by reference for their description of expansion agents known in the art.

Agents comprising cell-signaling molecules are also known in the art to increase proliferation or survival of stem cells. For example, Sphingosine-1-phosphate is known to induce proliferation of neural progenitor cells (Harada, J. et al, (2004) J. Neurochem. 88: 1026). U.S. Patent Application No. 20030113913 describes the use of retinoic acid in stem cell self renewal in culture. The contents of each of these references are specifically incorporated herein by reference for their description of expansion agents known in the art.

Agents comprising pharmacological or pharmaceutical compounds are also known in the art to increase proliferation or survival of stem cells. For example, inhibitors of glycogen synthase kinase maintain pluripotency of embryonic stem cells through activation of Wnt signaling (Sato, N. et al, (2004) Nat. Med. 10: 55-63). Inhibitors of apoptosis (Wang, Y. et al, (2004) Mol. Cell. Endocrinol. 218: 165), inhibitors of nitric oxide/nitric oxide synthase (Matarredona, E. R. et al, (2004) Brain Res. 995: 274) and inhibitors of histone deacetylases (Lee, J. H. et al, (2004) Genesis 38: 32-8) are also known to increase proliferation and/or pluripotency. For example, the peptide humanin is an inhibitor of Bax function that suppresses apoptosis (Guo, B. et al, (2003) Nature 423: 456-461). The contents of each of these references are specifically incorporated herein by reference for their description of expansion agents known in the art.

Oocyte production can be further increased by contacting compositions comprising female germline stem cells, or progenitors derived from female germline stem cells, with an agent that differentiates female germline stem cells or their progenitors into oocytes (e.g., differentiation agents). Such differentiation agents include, but are not limited to, a hormone or growth factor (e.g., TGF, BMP, Wnt protein, SCF or LIF), a signaling molecule (e.g., meiosis-activating sterol, "FF-MAS"), or a pharmacologic or pharmaceutical agent (e.g., a modulator of Id protein function or Snail/Slug transcription factor function).

Agents comprising growth factors are known in the art to induce differentiation of stem cells. For example, TGF-β can induce differentiation of hematopoietic stem cells (Ruscetti, F. W. et al, (2001) Int. J. Hematol. 74: 18-25). U.S. Patent Application No. 2002142457 describes methods for differentiation of cardiomyocytes using BMPs. Pera et al describe human embryonic stem cell differentiation using BMP-2 (Pera, M. F. et al, (2004) J. Cell Sci. 117: 1269). U.S. Patent Application No. 20040014210 and U.S. Pat. No. 6,485,972 describe methods of using Wnt proteins to induce differentiation. U.S. Pat. No. 6,586,243 describes differentiation of dendritic cells in the presence of SCF. U.S. Pat. No. 6,395,546 describes methods for generating dopaminergic neurons in vitro from embryonic and adult central nervous system cells using LIF. The contents of each of these references are specifically incorporated herein by reference for their description of differentiation agents known in the art.

Agents comprising signaling molecules are also known to induce differentiation of oocytes. FF-Mas is known to promote oocyte maturation (Marin Bivens, C. L. et al, (2004) BOR papers in press). The contents of each of these references are specifically incorporated herein by reference for their description of differentiation agents known in the art.

Agents comprising pharmacological or pharmaceutical compounds are also known in the art to induce differentiation of stem cells. For example, modulators of Id are involved in hematopoietic differentiation (Nogueria, M. M. et al, (2000) 276: 803) and Modulators of Snail/Slug are known to induce stem cell differentiation (Le Douarin, N. M. et al, (1994) Curr. Opin. Genet. Dev. 4: 685-695; Plescia, C. et al, (2001) Differentiation 68: 254-69). The contents of each of these references are specifically incorporated herein by reference for their description of differentiation agents known in the art.

The present invention also provides methods for reducing female germline stem cells, or progenitors derived from female germline stem cells, in vivo, ex vivo or in vitro, comprising contacting female germline stem cells or their progenitor cells with an agent that reduces cell proliferation, inhibits cell survival or promotes cell death. Unwanted proliferation of the cells of the invention can give rise to cancerous and pre-cancerous phenotypes (e.g., germ cell tumors, ovarian cancer). Such methods can be used to control unwanted proliferation (e.g., cancer) or for contraceptive measures by reducing the numbers of germline stem cells, and optionally their progenitors or oocytes.

Agents that reduce cell proliferation include, but are not limited to, a hormone or growth factor (e.g., TGF-β), a peptide antagonist of mitogenic hormones or growth factors (e.g., the BMP antagonists, PRDC and Gremlin), or a pharmacological or pharmaceutical compound (e.g., a cell cycle inhibitor, or an inhibitor of growth factor signaling).

Agents that inhibit cell survival include, but are not limited to, a hormone, growth factor or cytokine (e.g., a pro-apoptotic TNF super family member such as TNF-α, FasL and TRAIL), an antagonist of pro-survival Bcl-2 family member function, a signaling molecule (e.g., a ceramide), or a pharmacological or pharmaceutical compound (e.g., an inhibitor of growth factor signaling). Pro-survival Bcl-2 family members include Bcl-2, Bcl-xl (Cory, S, and Adams, J. M. (2000) Nat Rev Cancer 2(9):647-656; Lutz, R. J. (2000) Cell Survival Apoptosis 28:51-56), Bcl-W (Gibson, L., et al. (1996) *Oncogene* 13, 665-675; Cory, S, and Adams, J. M. (2000) Nat Rev Cancer 2(9):647-656), Mcl-1 (Kozopas, K. M., et al. (1993) Proc. Natl. Acad. Sci. U.S.A. 90:3516-3520; Reynolds, J. E., et al. (1994) Cancer Res. 54:6348-6352; Cory, S, and Adams, J. M. (2000) Nat Rev Cancer 2(9):647-656) and A1 (Cory, S, and Adams, J. M. (2000) Nat Rev Cancer 2(9):647-656; Gonzales, J., et al. (2003) Blood 101(7):2679-2685; Reed, J. C. (1997) Nature 387:773-776).

Agents that promote cell death include, but are not limited to, a pro-apoptotic tumor necrosis factor superfamily member (e.g., TNF-α, FasL and TRAIL), agonist of pro-apoptotic Bcl-2 family member function and ceramide. Pro-apoptotic Bcl-2 family members include Bax (Oltvai, Z N, et al. (1993): Cell 74: 609-619), Bak (Chittenden, T, et al. (1995) Nature 374:733-736), Bid (Luo, X., et al. (1998) Cell 94:481-490), Hrk (Inohara, N. et al. (1997) EMBO J. 16(7):1686-1694), Bod (Hsu, et al. (1998) Mol. Endocrinol. 12(9):1432-1440), Bim (O'Connor, L., et al. (1998) EMBO J. 17(2):385-395), Noxa (Oda, E., et al. (2000) Science 288, 1053-1058; Yakovlev, A. G., et al. (2004) J Biol Chem 279(27):28367-28374), puma (Nakano, K. and Vousden, K. H. (2001) Mol Cell 7(3):683-694), Bok (Yakovlev, A. G., et al. (2004) J Biol Chem 279(27):28367-28374; Hsu, S Y, et al. (1997) Proc Natl Acad Sci USA. 94(23):12401-6) and Bcl-xs (Boise, L. H., et al. (1993) Cell 74:597-608).

Several agents are known in the art to inhibit cell proliferation or survival or promote cell death, including PRDC (Sudo et al, (2004) J. Biol. Chem., advanced publication), TNF (Wong, G. et al, (2004) Exp. Neurol. 187: 171), FasL (Sakata, S. et al, (2003) Cell Death Differ. 10: 676) and TRAIL (Pitti, R M, et al. (1996) J Biol Chem 271: 12687-12690; Wiley, S R, et al. (1995) Immunity 3: 673-682). Ceramide mediates the action of tumor necrosis factor on primitive human hematopoietic cells (Maguer-Satta, V. et al, (2000) Blood 96: 4118-23).

Agonist/antagonist of Bcl-2 family members, such as Bcl-2, Bcl-XL, Bcl-W, Mcl-1, A1, Bax, Bak, Bid, Hrk, Bod, Bim, Noxa, Puma, Bok and Bcl-xs, are known to inhibit stem cell survival (Lindsten, T. et al, (2003) J. Neurosci. 23: 11112-9). Agents comprising pharmacological or pharmaceutical compounds are also known in the art to inhibit cell survival. For example, inhibitors of growth factor signaling, such as QSulf1, a heparan sulfate 6-O-endosulfatase that inhibits fibroblast growth factor signaling, can inhibit stem cell survival (Wang, S. et al, (2004) Proc. Natl. Acad. Sci. USA 101: 4833). The contents of each of these references are specifically incorporated herein by reference for their description of agents known in the art to inhibit cell survival.

Agents can be administered to subjects in need thereof by a variety of administration routes. Methods of administration, generally speaking, may be practiced using any mode of administration that is medically acceptable, meaning any mode that produces effective levels of the active compounds without causing clinically unacceptable adverse effects. Such modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes. The term "parenteral" includes subcutaneous, intravenous, intramuscular, intraperitoneal, or infusion. Intravenous or intramuscular routes are not particularly suitable for long-term therapy and prophylaxis. A particular method of administration involves coating, embedding or derivatizing fibers, such as collagen fibers, protein polymers, etc. with therapeutic proteins. Other useful approaches are described in Otto, D. et al., J. Neurosci. Res. 22: 83-91 and in Otto, D. and Unsicker, K. J. Neurosci. 10: 1912-1921.

In vitro and ex vivo applications can involve culture of the germline stem cells or their progenitors with the selected agent to achieve the desired result.

Agents of the invention may be supplied along with additional reagents in a kit. The kits can include instructions for the treatment regime or assay, reagents, equipment (test tubes, reaction vessels, needles, syringes, etc.) and standards for calibrating or conducting the treatment or assay. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

III. Culture

Germline stem cells of the invention, and progenitors derived from germline stem cells, can be used for many diverse clinical and pre-clinical applications, which can include, but are not limited to, experimental use in toxicological or genomic screening methods, as well as treatment of the diseases disclosed herein.

The present invention provides methods for expanding female germline stem cells, or progenitors derived from female germline stem cells, in vitro, comprising contacting a female germline stem cell, or its progenitor, with an agent that promotes cell proliferation or survival. Expansion agents can be the same as are used in vivo and ex vivo, and include, but are not limited to, a hormone or growth factor (e.g., a IGF, TGF, BMP, Wnt protein or FGF), a cell-signaling molecule (e.g., S1P or RA), or a pharmacological or pharmaceutical compound (e.g., an inhibitor of GSK-3, an inhibitor of apoptosis such as a Bax inhibitor or caspase inhibitor, an inhibitor of nitric oxide production, or an inhibitor of HDAC activity).

Female germline stem cells and their progenitors can provide differentiated and undifferentiated cultured cell types for high-throughput toxicological or genomic screening as well as therapeutic use. The cells can be cultured in, for example, 96-well or other multi-well culture plates to provide a system for scale-up and high-throughput screening of, for example, target cytokines, chemokines, growth factors, or pharmaceutical compositions in pharmacogenomics or pharmacogenetics. Cytokines, hormones, pharmaceutical compositions and growth factors, for example, can therefore be screened in a timely and cost-effective manner to more clearly elucidate their effects.

Germline stem cells of the invention, or progenitors derived from germline stem cells, further provide a unique system in which cells can be differentiated to form specific cell lineages (e.g., oocytes). Cultures of cells (from the same individual and from different individuals) can be treated with differentiation agents of interest to stimulate the production of oocytes, which can then be used for a variety of therapeutic applications (e.g., in vitro fertilization, somatic cell nuclear transfer).

Modulation of the properties of female germline stem cell or their progenitors, such as their proliferation rate, their rate of death, their differentiation into oocytes or other cell types, their longevity, their suitability for handling, transplantation, culture, preservation, or other properties, can be assessed in culture. Isolated cells can be cultured in a range of media suitable for cell culture. Additives include but are not be limited to serum, antibiotics (if needed), and bioactive molecules like LIF, Kit ligand, and βFGF, Flt-3 ligand, etc.

Differentiation of female germline stem cells or their progenitors, as represented by meiotic entrance and oocyte development, or development into other cell lineages, including somatic cells, can be achieved using standard methods known in the art. As with other undifferentiated or partially differentiated precursor cells, germline stem cells or their progenitors can be induced to follow a particular developmental pathway by culture in medium containing agents known in the art. Such agents can be provided through "co-culture" schemes, wherein cells that secrete such factors are cultured together with germline stem cells or their progenitors to direct the development of germline stem cells or their progenitors. These agents include, but are not limited to the following (with regards to biological signaling pathways, pharmacological or biological antagonists, agonists, or other modulators of function are to be included in each case): Wnt pathway molecules, TGFβ and/or BMP pathway molecules, modulators of epigenetic mechanisms including histone modification pathways (including but not limited to acetylation, methylation, etc.), gonadotropins, steroid hormones (including but not limited to estrogen, progesterone, androgens, etc.), IGF and/or insulin signaling molecules, leptin and related signaling molecules, members of the sphingolipid family (including but not limited to Sphingosine-1-Phosphate, ceramide, etc.), regulators of apoptosis (including but not limited to Caspase inhibitors, the Bax inhibitor humanin, etc.), Notch pathway molecules, cell-cycle regulators including so-called cellular senescence pathways (including but not limited to Bmi-1, the Ink4a locus, etc.), regulators of receptor-kinases, and intracellular kinase cascades, and strategies that modulate gene expression via gene expression interference (including but not limited to variants of RNA interference, morpholino technologies, or antisense RNA molecules, etc.). Some specific examples of such factors, the progenitor/precursor cells on which they act, and the resulting cell types formed are shown in Table 1.

netic cellular responses to biologic or pharmacologic agents, or combinatorial libraries of such agents, germline stem cells or their progenitors are preferably isolated from a statistically significant population of subjects, culture expanded, and contacted with one or more biologic or pharmacologic agents. Germline stem cells of the invention or their progenitors optionally can be induced to differentiate, wherein differentiated cells are the desired target for a certain biologic or pharmacologic agent, either prior to or after culture expansion. By comparing the one or more cellular responses of the cultures from subjects in the statistically significant population, the effects of the biologic or pharmacologic agent can be determined. Effects of the biologic or pharmacologic agent can be induction of apoptosis, changes in gene expression, chromosomal damage, and decreases or increases in hormones involved in ovarian function.

Alternatively, genetically identical germline stem cells, their progenitors, or their progeny, can be used to screen separate compounds, such as compounds of a combinatorial

TABLE 1

Selected Examples of Differentiation Agents

| Agent | Progenitor/precursor | Differentiated Cell |
|---|---|---|
| Vascular Endothelial Growth Factor | Embryonic Stem Cell | Hematopoietic Cell[1] |
| Sonic Hedgehog | Floor Plate | Motor Neuron[2] |
| Insulin-like Growth Factor II | Embryonic Stem Cell | Myoblast[3] |
| Osteogenin | Osteoprogenitor | Osteoblast[4] |
| Cytotoxic T Cell Differentiation Factor | Spleen Cell | Cytotoxic T Lymphocyte[5] |
| □-catenin | Skin Stem Cell | Follicular Keratinocyte[6] |
| Bone Morphogenic Protein 2 | Mesenchymal Stem Cell | Adipocytes, Osteoblasts[7] |
| Interleukin 2 | Bone Marrow Precursor | Natural Killer Cells[8] |
| Transforming Growth Factor □ | Cardiac Fibroblast | Cardiac Myocyte[9] |
| Nerve Growth Factor | Chromaffin Cell | Sympathetic Neuron[10] |
| Steel Factor | Neural Crest | Melanocyte[11] |
| Interleukin 1 | Mesencephalic Progenitor | Dopaminergic Neuron[12] |
| Fibroblast Growth Factor 2 | GHFT | Lactotrope[13] |
| Retinoic Acid | Promyelocytic Leukemia | Granulocyte[14] |
| Wnt3 | Embryonic Stem Cell | Hematopoietic Cell[15] |

[1]Keller, et al. (1999) Exp. Hematol. 27: 777-787.
[2]Marti, et al. (1995) Nature. 375: 322-325.
[3]Prelle, et al. (2000) Biochem. Biophy. Res. Commun. 277: 631-638.
[4]Amedee, et al. (1994) Differentiation. 58: 157-164.
[5]Hardt, et al. (1985) Eur. J. Immunol. 15: 472-478.
[6]Huelsken, et al. (2001) Cell. 105: 533-545.
[7]Ji, et al. (2000) J. Bone Miner. Metab. 18: 132-139.
[8]Migliorati, et al. (1987) J. Immunol. 138: 3618-3625.
[9]Eghbali, et al. (1991) Proc. Natl. Acad. Sci. USA. 88: 795-799.
[10]Niijima, et al. (1995) J. Neurosci. 15: 1180-1194.
[11]Guo, et al. (1997) Dev. Biol. 184: 61-69.
[12]Ling, et al. (1998) Exp. Neurol. 149: 411-423.
[13]Lopez-Fernandez, et al. (2000) J. Biol. Chem. 275: 21653-60.
[14]Wang, et al. (1989) Leuk. Res. 13: 1091-1097.
[15]Lako, et al. (2001) Mech. Dev. 103: 49-59.

The cells of the present invention can provide a variety of cell types, including terminally differentiated and undifferentiated cell types, for high-throughput screening techniques used to identify a multitude of target biologic or pharmacologic agents. Importantly, the female germline stem cells or their progenitor cells provide a source of cultured cells from a variety of genetically diverse subjects, who may respond differently to biologic and pharmacologic agents.

The present invention provides methods for using the germline stem cells, or their progenitors, described herein to characterize pharmacogenetic cellular responses to biologic or pharmacologic agents. In the method of using germline stem cells or their progenitors to characterize pharmacogelibrary. Gene expression systems for use in combination with cell-based high-throughput screening have been described (Jayawickreme, C. and Kost, T., (1997) Curr. Opin. Biotechnol. 8: 629-634).

The invention also envisions a tissue-engineered organ (e.g., ovary), or portion, or specific section thereof, or a tissue engineered device comprising a tissue of interest and optionally, cytokines, hormones, growth factors, or differentiation factors that induce differentiation into a desired cell type, wherein the germline stem cells of the invention or their progenitors are used to generate tissues including, but not limited to ovarian tissue. Tissue-engineered organs can be used with a biocompatible scaffold to support cell growth in a three-dimensional configuration, which can be biodegradable. Tissue-engineered organs generated from the germline stem cells of the present invention or their progenitors can be implanted into a subject in need of a replacement organ, portion, or specific section thereof.

Homogenous organs, portions, or individual cells derived from the germline stem cell or progenitor cultures of the invention can be implanted into a host. Likewise, heterogeneous organs, portions, or sections derived from germline stem cells or their progenitors induced to differentiate into multiple tissue types can be implanted into a subject in need thereof. The transplantation can be autologous, such that the donor of the stem cells from which organ or organ units are derived is the recipient of the engineered tissue. The transplantation can be heterologous, such that the donor of the stem cells from which organ or organ units are derived is not that of the recipient of the engineered-tissue.

Once transferred into a host, the tissue-engineered organs can recapitulate the function and architecture of the native host tissue. The tissue-engineered organs will benefit subjects in a wide variety of applications, including the treatment of cancer and other disease disclosed herein, congenital defects, or damage due to surgical resection.

Polymer scaffolds that can be used in the development of tissue-engineered organs derived from the germline stem cells of the invention function in place of a connective tissue scaffold or matrix, and are designed to optimize gas, nutrient, and waste exchange by diffusion. Polymer scaffolds can comprise, for example, a porous, non-woven array of fibers. The polymer scaffold can be shaped to maximize surface area, to allow adequate diffusion of nutrients and growth factors to the cells. Taking these parameters into consideration, one of skill in the art could configure a polymer scaffold having sufficient surface area for the cells to be nourished by diffusion until new blood vessels interdigitate the implanted engineered-tissue using methods known in the art. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo($\varepsilon$-caprolactone)diol as switching segment/oligo(p-dioxyanone)diol as physical crosslink. Other suitable polymers can be obtained by reference to The Polymer Handbook, 3rd edition (Wiley, N.Y., 1989).

Factors, including but not limited to nutrients, growth factors, inducers of differentiation or de-differentiation, products of secretion, immunomodulators, inhibitors of inflammation, regression factors, hormones, or other biologically active compounds can be incorporated into or can be provided in conjunction with the polymer scaffold.

IV. Screening Assays

The invention provides methods for identifying modulators, i.e., candidate or test compounds or agents (e.g., proteins, peptides, peptidomimetics, peptoids, small molecules or other drugs) which modulate female germline stem cells or female germline stem cell progenitor cells. Agents thus identified can be used to modulate, for example, proliferation, survival and differentiation of a female germline stem cell or its progenitor e.g., in a therapeutic protocol.

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In one aspect the compounds are organic small molecules, that is, compounds having molecular weight less than 1,000 amu, alternatively between 350-750 amu. In other aspects, the compounds are: (i) those that are non-peptidic; (ii) those having between 1 and 5, inclusive, heterocyclyl, or heteroaryl ring groups, which may bear further substituents; (iii) those in their respective pharmaceutically acceptable salt forms; or (iv) those that are peptidic.

The term "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring can be substituted by a substituent.

The term "substituents" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, $SO_3H$, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention.

The compounds described herein can also be represented in multiple tautomeric forms, all of which are included herein. The compounds can also occur in cis- or trans- or E- or Z-double bond isomeric forms. All such isomeric forms of such compounds are expressly included in the present invention.

Test agents of the invention can also be peptides (e.g., growth factors, cytokines, receptor ligants).

Screening methods of the invention can involve the identification of an agent that increases the proliferation or survival of female germline stem cells or female germline stem cell progenitor cells. Such methods will typically involve contacting a population of the female germline stem or progenitor cells with a test agent in culture and quantitating the number of new stem or progenitor cells produced as a result. Comparison to an untreated control can be concurrently assessed. Where an increase in the number of stem or progenitor cells is detected relative to the control, the test agent is determined to have the desired activity.

In practicing the methods of the invention, it may be desirable to employ a purified population of female germline stem cells or their progenitor cells. A purified population of female germline stem cells or female germline stem cell progenitor cells have about 50-55%, 55-60%, 60-65% and 65-70% purity. More preferably the purity is about 70-75%, 75-80%, 80-85%; and still more preferably the purity is about 85-90%, 90-95%, and 95-100%.

In other methods, the test agent is assayed using a biological sample rather than a purified population of stem or progenitor cells. The term "biological sample" includes tissues, cells and biological fluids isolated from a subject, as well as tissues, cells and fluids present within a subject. Preferred biological samples include bone marrow, peripheral blood and ovarian tissue.

Increased amounts of female germline stem cells or female germline stem cell progenitor cells can also be detected by an increase in gene expression of genetic markers including an SSEA (e.g., SSEA-1), Oct-4, Dazl, Stella and Vasa. The level of expression can be measured in a number of ways, including, but not limited to: measuring the mRNA encoded by the genetic markers; measuring the amount of protein encoded by the genetic markers; or measuring the activity of the protein encoded by the genetic markers.

The level of mRNA corresponding to a genetic marker can be determined both by in situ and by in vitro formats. The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe is sufficient to specifically hybridize under stringent conditions to mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the genetic markers described herein.

The level of mRNA in a sample can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the genetic marker being analyzed.

Screening methods of the invention can involve the identification of an agent that increases the differentiation of female germline stem cells or female germline stem cell progenitor cells into oocytes. Such methods will typically involve contacting a population of the stem or progenitor cells with a test agent in culture and quantitating the number of new oocytes produced as a result. Comparison to an untreated control can be concurrently assessed. Where an increase in the number of oocytes is detected relative to the control, the test agent is determined to have the desired activity. The test agent can also be assayed using a biological sample (e.g., ovarian tissue); subsequent testing using a population of stem or progenitor cells may be conducted to distinguish the functional activity of the agent (e.g., differentiation rather then increase in proliferation or survival) where the result is ambiguous.

Increased amounts of oocytes can be detected by a decrease in gene expression of stem or progenitor genetic markers including an SSEA (e.g., SSEA-1), Oct-4, Dazl, Stella and Vasa or an increase in oocyte markers, such as HDAC6, GDF9 and ZP3.

Screening methods of the invention can involve the identification of an agent that decreases the proliferation or survival of female germline stem cells or female germline stem cell progenitor cells. Such methods will typically involve contacting a population of the stem or progenitor cells, or a biological sample containing said cells with a test agent in culture and quantitating the number of stem or progenitor cells lost as a result. Comparison to an untreated control can be concurrently assessed. Where a decrease in the number of stem or progenitor cells is detected relative to the control, the test agent is determined to have the desired activity.

IV. Methods of Treatment

Female germline stem cells of the invention or their progenitors can be used in a variety of therapeutic applications (e.g., oocyte generation for in vivo restoration or ex vivo procedures including in vitro fertilization and somatic cell nuclear transfer). Accordingly, methods of the invention relate to the use of female germline stem cells, or progenitors derived from female germline stem cells, to, among other things, expand the follicle reserve as a means of enhancing or restoring fertility in females, and for ameliorating symptoms and consequences of menopause.

Thus, the present invention provides methods for treating infertility comprising providing a female germline stem cell, its progenitor, or the progeny thereof, to a female subject in need thereof, wherein the cell engrafts into a tissue and differentiates into an oocyte, which can later be provided for fertilization (e.g., following ovulation or in vitro fertilization). Preferably, the tissue is ovarian tissue, however, other tissues in the body may host the engrafted cell that in turn generates an oocyte. Oocytes harbored in extra-ovarian tissues can be harvested and used for procedures including in vitro fertilization.

The present invention also provides methods for treating infertility comprising contacting ovarian tissue of a female subject in need thereof with an agent that increases the production or survival of female germline stem cells or their progenitors. As previously described, oocyte production can be increased by increasing the number (i.e., proliferation) or life span (i.e., survival) of female germline stem cells or their progenitors, as well as by differentiating female germline stem cells or their progenitors into oocytes. Such oocytes can later be provided for fertilization following ovulation in the subject.

The present invention also provides methods for repairing damaged ovarian tissue, comprising providing a female germline stem cell, or its progenitor, to the tissue, wherein the cell engrafts into the tissue and differentiates into an oocyte. Damage can be caused, for example, by exposure to cytotoxic factors, chemotherapeutic drugs, radiation, hormone deprivation, growth factor deprivation, cytokine deprivation, cell receptor antibodies, and the like. Chemotherapeutic drugs include, but are not limited to, 5-FU, vinblastine, actinomycin D, etoposide, cisplatin, methotrexate, doxorubicin, among others. Damage can also be caused be diseases that affect ovarian function, including, but not limited to cancer, polycystic ovary disease, genetic disorders, immune disorders, metabolic disorders, and the like.

The present invention also provides methods for restoring ovarian function in a menopausal female subject, comprising providing a female germline stem cell, or its progenitor, to the subject, wherein the cell engrafts into the ovary and differentiates into an oocyte. The menopausal female subject can be in a stage of either peri- or post-menopause, with said menopause caused by either normal (e.g., aging) or pathological (e.g., surgery, disease, ovarian damage) processes.

Ovarian function in a post-menopausal female can also be restored by contacting ovarian tissue of the subject with an agent that increases the amount of female germline stem cells or their progenitors (e.g., by increasing the number or life span of female germline stem cells, as well as by increasing the differentiation of female germline stem cells into oocytes).

Restoration of ovarian function can relieve adverse symptoms and complications associated with menopausal disorders, including, but not limited to, somatic disorders such as osteoporosis, cardiovascular disease, somatic sexual dysfunction, hot flashes, vaginal drying, sleep disorders, depression, irritability, loss of libido, hormone imbalances, and the like, as well as cognitive disorders, such as loss of memory; emotional disorders, depression, and the like.

The present invention further provides a method for contraception in a female subject comprising contacting ovarian tissue of the subject with an agent that decreases the proliferation, function or survival of female germline stem cells or their progenitors.

Germline stem cells of the invention, their progenitors or their in vitro-derived progeny, can be administered as previously described. Prior to administration, germline stem cells, their progenitors or their in vitro-derived progeny, described herein can optionally be genetically modified, in vitro, in vivo or ex vivo, by introducing heterologous DNA or RNA or protein into the cell by a variety of recombinant methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer.

The germline stem cells of the invention, their progenitors or their in vitro-derived progeny, can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. The altered genome may contain the genetic sequence of a selectable or screenable marker gene that is expressed so that the cell with altered genome, or its progeny, can be differentiated from cells having an unaltered genome. For example, the marker may be a green, red, yellow fluorescent protein, β-galactosidase, the neomycin resistance gene, dihydrofolate reductase (DHFR), or hygromycin, but are not limited to these examples.

In some cases, the underlying defect of a pathological state is a mutation in DNA encoding a protein such as a metabolic protein. Preferably, the polypeptide encoded by the heterologous DNA lacks a mutation associated with a pathological state. In other cases, a pathological state is associated with a decrease in expression of a protein. A genetically altered germline stem cell, or its progeny, may contain DNA encoding such a protein under the control of a promoter that directs strong expression of the recombinant protein. Alternatively, the cell may express a gene that can be regulated by an inducible promoter or other control mechanism where conditions necessitate highly controlled regulation or timing of the expression of a protein, enzyme, or other cell product. Such stem cells, when transplanted into a subject suffering from abnormally low expression of the protein, produce high levels of the protein to confer a therapeutic benefit. For example, the germline stem cell of the invention, its progenitors or its in vitro-derived progeny, can contain heterologous DNA encoding genes to be expressed, for example, in gene therapy. Germline stem cells of the invention, their progenitors or their progeny, can contain heterologous DNA encoding Atm, the gene responsible for the human disease Ataxia-telangiectasia in which fertility is disrupted. Providing Atm via germline stem cells, its progenitors or its in vitro-derived progeny, can further relieve defects in ovarian function. DNA encoding a gene product that alters the functional properties of germline stem cells in the absence of any disease state is also envisioned. For example, delivery of a gene that inhibits apoptosis, or that prevents differentiation would be beneficial.

Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Calcium phosphate transfection can be used to introduce plasmid DNA containing a target gene or polynucleotide into isolated or cultured germline stem cells or their progenitors and is a standard method of DNA transfer to those of skill in the art. DEAE-dextran transfection, which is also known to those of skill in the art, may be preferred over calcium phosphate transfection where transient transfection is desired, as it is often more efficient. Since the cells of the present invention are isolated cells, microinjection can be particularly effective for transferring genetic material into the cells. This method is advantageous because it provides delivery of the desired genetic material directly to the nucleus, avoiding both cytoplasmic and lysosomal degradation of the injected polynucleotide. This technique has been used effectively to accomplish germline modification in transgenic animals. Cells of the present invention can also be genetically modified using electroporation.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPA) can be added. Commercially available reagents for liposomal transfer include Lipofectin (Life Technologies). Lipofectin, for example, is a mixture of the cationic lipid N-[1-(2,3-dioleyloxy)propyl]-N—N—N-trimethyl ammonia chloride and DOPE. Liposomes can carry larger pieces of DNA, can generally protect the polynucleotide from degradation, and can be targeted to specific cells or tissues. Cationic lipid-mediated gene transfer efficiency can be enhanced by incorporating purified viral or cellular envelope components, such as the purified G glycoprotein of the vesicular stomatitis virus envelope (VSV-G). Gene transfer techniques which have been shown effective for delivery of DNA into primary and established mammalian cell lines using lipopolyamine-coated DNA can be used to introduce target DNA into the germline stem cells described herein.

Naked plasmid DNA can be injected directly into a tissue mass formed of differentiated cells from the isolated germline stem cells or their progenitors. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA. Microprojectile gene transfer can also be used to transfer genes into stem cells either in vitro or in vivo. The basic procedure for microprojectile gene transfer was described by J. Wolff in Gene Therapeutics (1994), page 195. Similarly, microparticle injection techniques have been described previously, and methods are known to those of skill in the art. Signal peptides can be also attached to plasmid DNA to direct the DNA to the nucleus for more efficient expression.

Viral vectors are used to genetically alter germline stem cells of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors that can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Peptide or protein transfection is another method that can be used to genetically alter germline stem cells of the invention and their progeny. Peptides including, but not limited to, Pep-1 (commercially available as Chariot™) and MPG, can quickly and efficiently transport biologically active proteins, peptides, antibodies, and nucleic acids directly into cells, with an efficiency of about 60% to about 95% (Morris, M. C. et al, (2001) Nat. Biotech. 19: 1173-1176). Without wishing to be bound by theory, the peptide forms a non-covalent bond with the macromolecule of interest (i.e., protein, nucleic acid). The binding reaction stabilizes the protein and protects it from degradation. Upon delivery into the cell of interest, such as stem cells of the invention, the peptide-macromolecule complex dissociates, leaving the macromolecule biologically active and free to proceed to its target organelle. Delivery can occur in the presence of absence of serum. Uptake and delivery can occur at 4° C., which eliminates endosomal processing of incoming macromolecules. Movement of macromolecules through the endosomal pathway can modify the macromolecule upon uptake. Peptides such as Pep-1, by directly delivering a protein, antibody, or peptide of interest, bypass the transcription-translation process.

Methods of the invention can provide oocyte reserves for use in ex vivo procedures, such as somatic cell nuclear transfer. Employing recombinant techniques prior to nuclear transfer will allow for the design of customized oocytes and ultimately produce embryos from which embryonic stem cells can be derived. In addition, genetic manipulation of donor DNA prior to nuclear transfer will result in embryos that possess the desired modification or genetic trait.

Methods of somatic cell nuclear transfer are well known in the art. See U.S. application Ser. No. 10/494,074, filed on Mar. 24, 2004 and published as 20050064586; Wilmut et al. (1997) Nature, 385, 810-813; Wakayama, et al. (1998) Nature 394: 369-374; and Teruhiko et al., (1999) PNAS 96:14984-14989. Nuclear transplantation involves the transplantation of donor cells or cell nuclei into enucleated oocytes. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal.

Methods for the generation of embryonic stem cells from embryos are also well known in the art. See Evans, et al. (1981) Nature, 29:154-156; Martin, et al. (1981) PNAS, 78:7634-7638; Smith, et al. (1987) Development Biology, 121:1-9; Notarianni, et al. (1991) J. Reprod. Fert., Suppl. 43:255-260; Chen R L, et al. (1997) Biology of Reproduction, 57 (4):756-764; Wianny, et al. (1999) Theriogenology, 52 (2):195-212; Stekelenburg-Hamers, et al. (1995) Mol. Reprod. 40:444-454; Thomson, et al. (1995) PNAS, 92 (17):7844-8 and Thomson (1998) Science, 282 (6):1145-1147. Accordingly, embryos produced from oocytes of the invention can be genetically modified, either through manipulation of the oocyte in vitro prior to fertilization or manipulation of donor DNA prior to nuclear transfer into the enucleated oocyte, to produce embryos having a desired genetic trait.

VI. In Vitro Fertilization

Oocytes produced from germline stem cells of the invention, or progenitors derived from germline stem cells of the invention, as described herein may also be used for methods of in vitro fertilization. Accordingly, the invention provides methods for in vitro fertilization of a female subject. The method comprises the steps of: either producing an oocyte by culturing a female germline stem cell, or its progenitor, in the presence of an oocyte differentiation agent or in vivo differentiating the female germline stem cell, or its progenitor into an oocyte and obtaining the oocyte; fertilizing the oocyte in vitro to form a zygote; and implanting the zygote into the uterus of a female subject.

Methods of in vitro fertilization are well known in the art, and are now rapidly becoming commonplace. Couples are generally first evaluated to diagnose their particular infertility problem(s). These may range from unexplained infertility of both partners to severe problems of the female (e.g., endometriosis resulting in nonpatent oviducts with irregular menstrual cycles or polycystic ovarian disease) or the male (e.g., low sperm count with morphological abnormalities, or an inability to ejaculate normally as with spinal cord lesions, retrograde ejaculation, or reversed vasectomy). The results of these evaluations also determine the specific procedure to be performed for each couple.

Procedures often begin with the administration of a drug to down-regulate the hypothalamic/pituitary system (LHRH agonist). This process decreases serum concentrations of the gonadotropins, and developing ovarian follicles degenerate, thereby providing a set of new follicles at earlier stages of development. This permits more precise control of the maturation of these new follicles by administration of exogenous gonadotropins in the absence of influences by the hypothalamic pituitary axis. The progress of maturation and the number of growing follicles (usually four to ten stimulated per ovary) are monitored by daily observations using ultrasound and serum estradiol determinations. When the follicles attain preovulatory size (18-21 mm) and estradiol concentrations continue to rise linearly, the ovulatory response is initiated by exogenous administration of human chorionic gonadotropins (hCG).

Oocytes can be obtained from germline stem cells, or progenitors derived from germline stem cells, as previously described herein. Germline stem cells, or progenitors derived from germline stem cells, can be cultured in the presence of an oocyte differentiation agent which induces differentiation into oocytes. The differentiation agent can be supplied exogenously (e.g., added to the culture medium) or from endogenous sources during co-culture with allogenic or heterogenic ovarian tissue. Female germline stem cells or their progenitors can also be cultured in a tissue-engineered structure wherein the differentiation agent is either exogenously or endogenously supplied and oocytes are obtained.

Individual oocytes can be evaluated morphologically and transferred to a petri dish containing culture media and heat-inactivated serum. A semen sample is provided by the male partner and processed using a "swim up" procedure, whereby the most active, motile sperm will be obtained for insemination. If the female's oviducts are present, a procedure called GIFT (gamete intrafallopian transfer) can be performed at this time. By this approach, oocyte-cumulus complexes surrounded by sperm are placed directly into the oviducts by laproscopy. This procedure best simulates the normal sequences of events and permits fertilization to occur within the oviducts. Not surprisingly, GIFT has the highest success rate with 22% of the 3,750 patients undergoing ova retrieval in 1990 having a live delivery. An alternative procedure ZIFT (zygote intrafallopian transfer) permits the selection of in vitro fertilized zygotes to be transferred to oviducts the day following ova retrieval. Extra zygotes can be cryopreserved at this time for future transfer or for donation to couples without female gametes. Most patients having more serious infertility problems, however, will require an additional one to two days incubation in culture so that preembryos in the early cleavage states can be selected for transfer to the uterus. This IVF-UT (in vitro fertilization uterine transfer) procedure entails the transcervical transfer of several 2-6 cell (day 2) or 8-16 (day 3) preembryos to the fundus of the uterus (4-5 preembryos provides optimal success).

Procedures for in vitro fertilization are also described in U.S. Pat. Nos. 6,610,543 6,585,982, 6,544,166, 6,352,997, 6,281,013, 6,196,965, 6,130,086, 6,110,741, 6,040,340, 6,011,015, 6,010,448, 5,961,444, 5,882,928, 5,827,174, 5,760,024, 5,744,366, 5,635,366, 5,691,194, 5,627,066, 5,563,059, 5,541,081, 5,538,948, 5,532,155, 5,512,476, 5,360,389, 5,296,375, 5,160,312, 5,147,315, 5,084,004, 4,902,286, 4,865,589, 4,846,785, 4,845,077, 4,832,681, 4,790,814, 4,725,579, 4,701,161, 4,654,025, 4,642,094, 4,589,402, 4,339,434, 4,326,505, 4,193,392, 4,062,942, and 3,854,470, the contents of which are specifically incorporated by reference for their description of these procedures.

The following examples are put forth for illustrative purposes only and are not intended to limit the scope of what the inventors regard as their invention.

EXAMPLES

Example 1: Post-Natal Ovarian Germ-Cell Dynamics

Counts of healthy (non-atretic) and degenerating (atretic) follicles in ovaries of female mice were made to assess germ-cell dynamics in female mammals. In particular, degeneration rates were calculated, to determine the predictive age at which exhaustion of the oocyte (i.e., follicle) reserve would occur in the absence of new oocyte production.

Age-specified or timed-pregnant wild-type C57BL/6 and CD1 female mice were obtained from Charles River Laboratories, whereas AKR/J mice were obtained from Jackson Laboratories. Ovaries were fixed in 0.34N glacial acetic acid, 10% formalin, and 28% ethanol, paraffin embedded, and serially sectioned (8 µm). The sections were aligned in order on glass microscope slides, and stained with hematoxylin and picric methyl blue. The number of non-atretic or atretic primordial, primary, and preantral follicles was then determined. Primordial follicles were identified as having a compact oocyte surrounded by a single layer of flattened granulosa cells, while primary follicles were identified as having an enlarged oocyte surrounded by a single layer of cuboidal granulosa cells. Intermediate-stage follicles (compact or enlarged oocyte with a single layer of mixed flattened and cuboidal granulosa cells) were scored as primary. Preantral follicles were identified as having an enlarged oocyte surrounded by at least a partial or complete second layer of cuboidal granulosa cells, but no more than four complete layers of cuboidal granulosa cells. Only those follicles containing an oocyte with a clearly visible nucleus were scored. Follicles at the primordial, primary and preantral (immature) stages of development were scored as atretic if the oocyte was degenerating (convoluted, condensed) or fragmented. Grossly atretic follicles lacking oocyte remnants were not included in the analyses. Given that this procedure sampled one-fifth of the entire ovarian volume, the total number of follicles per ovary (healthy or atretic) was then estimated by multiplying the cumulative counts for each ovary by a correction factor of five (Zuckerman, S. (1951) Recent Prog. Horm. Res. 6: 63-108; Tilly, J. L. (2003) Reprod. Biol. Endocrinol. 1:1-11). A single trained ovarian histologist in a blinded fashion conducted all counts, and two other members of the group periodically evaluated random samples to verify accuracy and reproducibility of the data.

Figure 1B:
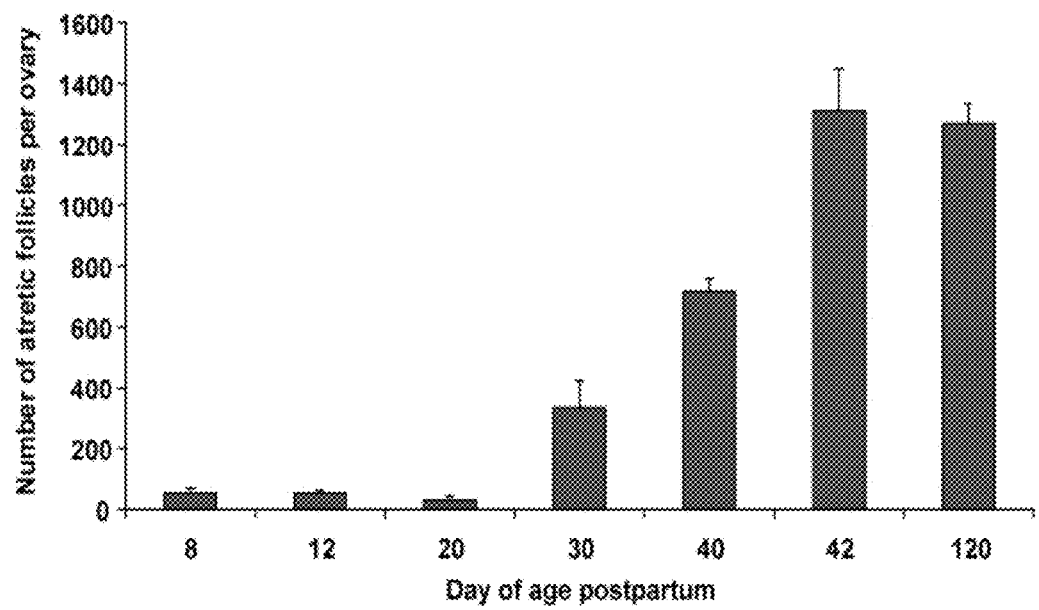
FIG. 1B shows the numbers of atretic, resting (primordial) and total immature (primordial, primary, small preantral) follicles in mouse ovaries during postnatal development.

Analysis of non-atretic quiescent (primordial) and early growing (primary, preantral) follicle numbers revealed that approximately one-third of the peak endowment of immature follicles was lost during development to young adulthood (see FIG. 1a), consistent with previous studies of follicle development in mice. Through the first 20 days of age, atresia occurred at a low but constant rate (FIG. 1b), consistent with a proportional decline in non-atretic follicle numbers during this time period (FIG. 1a). However, the incidence of atresia increased markedly by day 30 and further by day 40, reaching a peak level of more than 1,200 dying follicles per ovary on day 42 that was maintained well into reproductive life (FIG. 1b).

Clearance of apoptotic cells in vivo occurs within 3-18 hours (Wyllie, A. H. et al, (1980) Int. Rev. Cytol. 68: 251-306; Iijiri, K. and Potten, C. S. (1983) Br. J. Cancer 47: 175-185; Bursch, W. et al, (1990) Carcinogenesis 11: 847-853). Nonetheless, experiments were conducted to rule out the possibility that the large atretic follicle population observed in adult animals simply represented accumulation of oocyte corpses in follicles that had degenerated weeks earlier. The first experiment, based on past studies demonstrating that extensive levels of oocyte apoptosis occur in the newborn mouse ovary coincident with follicle formation, evaluated changes in the number of non-atretic oocytes between days 1 and 4 postpartum compared with the number of degenerative oocytes on day 4. More than 8,000 non-atretic oocytes were present per ovary on day 1, and this pool was reduced by almost 50% by day 4. However, only 218 degenerative oocytes per ovary were found on day 4, indicating that over 3,000 oocytes had died and had been cleared from the ovary between days 1 and 4 postpartum. Table 2 contains the data measuring developmental degeneration and clearance of oocytes in the neonatal mouse ovary.

TABLE 2

Developmental degeneration and clearance of oocytes in neonatal mouse ovaries

| Endpoint Analyzed | Age(s) postpartum | Number(s) per ovary |
|---|---|---|
| Non-atretic oocytes | Day 1 | 8,338 ± 1,150 |
| Non-atretic oocytes | Day 4 | 4,733 ± 68 |
| Oocytes lost | Day 1 to Day 4 | 3605 |
| Atretic oocytes | Day 4 | 218 ± 26 |
| Atretic oocytes cleared | Day 1 to Day 4 | 3,387 |

Figure 1C:
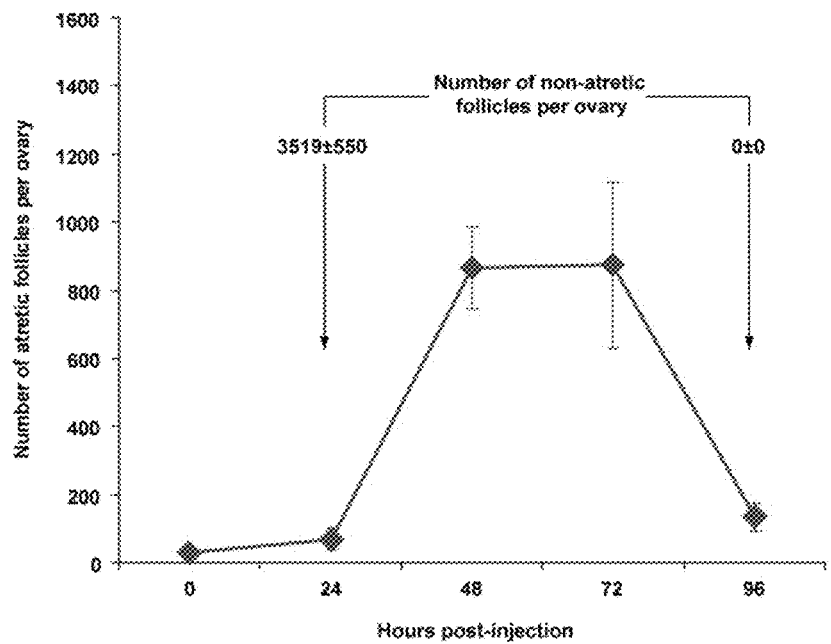
FIG. 1C depicts the incidence of primordial and primary follicle atresia in ovaries exposed to 9,10-dimethylbenz[a]anthracene ("DMBA") on day 25 postpartum.

A second approach to assessing clearance rates of degenerative oocytes was employed, using the chemical 9,10-dimethylbenz[a]anthracene (DMBA) to synchronize primordial and primary follicle atresia. Past studies have shown that DMBA induces degeneration of immature oocytes in a manner that morphologically resembles developmental oocyte death. For these experiments, C57BL/6 mice were given a single intraperitoneal injection of vehicle (corn oil) or DMBA (80 mg per kg body weight; resuspended in corn oil) on day 25 postpartum, and ovaries were collected just before injection and at 24-hour intervals after injection for up to 96 hours. In female mice given a single injection of DMBA, the incidence of follicle atresia increased markedly between 24 and 48 hours after injection, and remained at a plateau of approximately 850 atretic follicles per ovary from 48 to 72 hours after injection (FIG. 1c). By 96 hours after injection, there were no healthy primordial or primary follicles remaining in the ovaries, and the incidence of atresia returned to near-basal levels (FIG. 1c). Therefore, similar to the clearance rate of degenerative oocytes between postnatal days 1 and 4, DMBA-induced synchronization of atresia revealed that over 3,500 oocytes contained within primordial and primary follicles initiated apoptosis and were cleared from the ovary within a 3-day period.

Given this finding, which is that from 1% (days 8, 12, and 20) to as much as 16% (day 40) or more (33%, day 42; see FIG. 1d) of the immature follicle pool is degenerating at any given time under normal conditions, complete exhaustion of the follicle reserve by young adulthood would be predicted. However, the non-atretic pool of follicles declined from peak levels on day 12 by only 36% on day 40 (FIG. 1a). This indicated that the rate of follicle depletion during post-natal life, as determined by assessing changes in non-atretic follicle numbers, was highly incongruous with the numbers of follicles actually being eliminated from the ovaries through atresia in the same time frame.

Figure 1D:
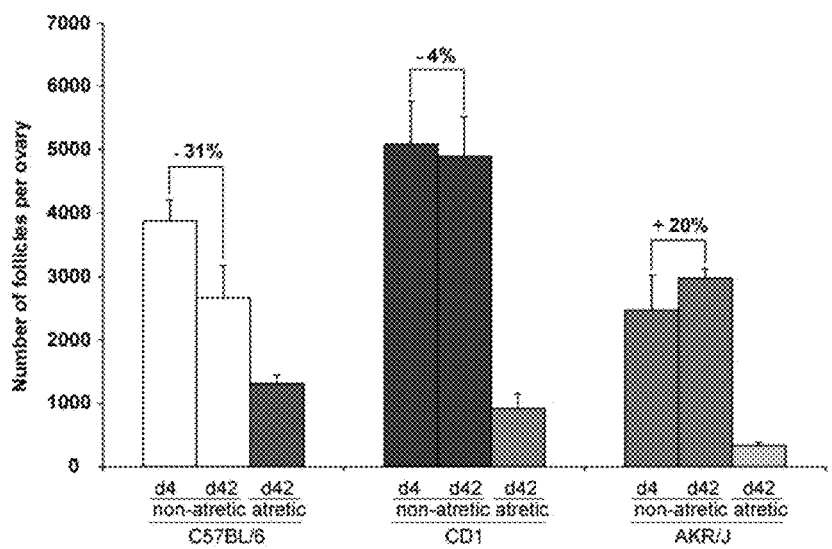
FIG. 1D shows the comparison of non-atretic and atretic immature follicle numbers in C57Bl/6, CD1 and AKR/J strains of mice.

To confirm that these findings were not a phenomenon related to C57BL/6 mice, changes in follicle numbers from birth to adulthood were analyzed in other strains of mice and compared with corresponding data from C57BL/6 females. In CD1 mice, the non-atretic follicle pool declined by only 4% between days 4 and 42 postpartum, despite a relatively high incidence of atresia, comparable to that observed in C57BL/6 females (FIG. 1d). The non-atretic follicle population in AKR/J mice was 20% larger on day 42 than on day 4, again despite a marked incidence of atresia (FIG. 1d). These data highlight a clear discordance between changes in non-atretic follicle numbers and the corresponding incidence of atresia in the postnatal mammalian ovary.

Similar studies were conducted in rhesus monkeys. Previous analyses of postnatal oocyte loss had been explained by simple exponential decay (Olesen, C. et al, (2004) Mol. Reprod. Dev. 67(1): 116-26). Oocyte loss after a number of periods of time had been projected by utilizing the following equation: $t_n = a(1-r)^n$; where $t_n$=the calculated number of remaining oocytes after n periods of time and a constant percentage of dying follicles, represented by r. Results from applying this equation using the numbers of healthy and dying follicles in the ovaries of rhesus monkeys were inconsistent with the idea that no new follicles are formed after birth in the primate. Rather, these data argue that female primates, like female mice, must produce new oocytes during adolescence and adult life.

Figure 2:
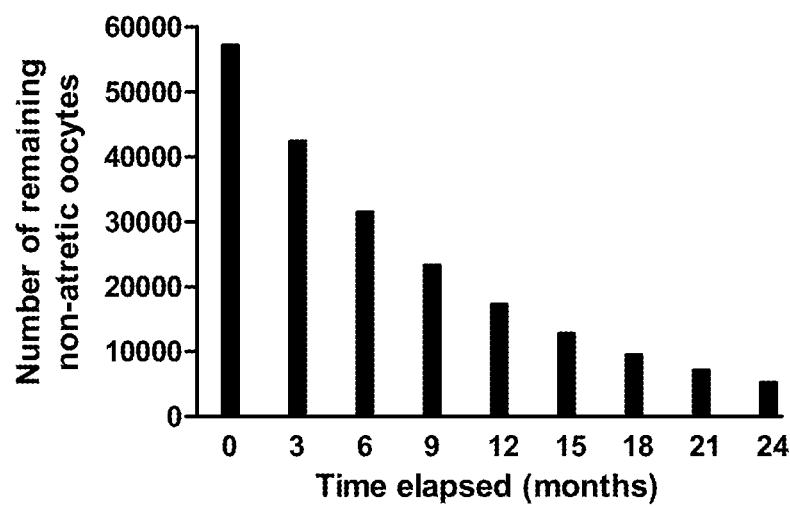
FIG. 2 shows the numbers of remaining non-atretic oocytes in rhesus monkeys.

Using ovaries from adolescent and mature female rhesus monkeys, Vernande-Van Eck measured both the percentage of dying oocytes at any given time (4.5%) as well as the rate of clearance of dying oocytes from the ovaries (14 days maximum). Using these values, exponential decay of oocytes would result in an approximate 95% reduction of the oocyte pool in only two years of time (see FIG. 2). The incidence of dying follicles was stable in both juvenile and in adult life. Thus, regardless of the age at which such decay is initiated, the rhesus monkey ovary would be in danger of entering a menopausal state in only two years. However, the rhesus monkey ovary is known to function from the onset of puberty (at approximately 4 years of age) for about 20 years prior to the onset of menopause (Schramm, R. D. et al, (2002) Hum. Reprod. 17: 1597-1603). However, projecting the exponential decay curve given Vermande Van-Eck's parameters to 7.7 years results in only 6 remaining oocytes.

As with the experiments conduced in mice, the findings in rhesus monkeys are incompatible with the concept of a fixed pool of oocytes at birth in female primates. The model described herein depicts a mechanism for continuing postnatal ovarian follicle renewal.

Example 2: Expression of Meiotic Entry Genes and Genes Implicated in Stem-Cell Function in Post-Natal Ovaries Replication of germ cells to produce oocytes for follicle formation in postnatal life would require expression of genes involved in the initiation of meiosis. Thus, expression of synaptonemal complex protein 3 (SCP3), a meiosis-specific protein necessary for formation of axial lateral elements of the synaptonemal complex, was examined in juvenile and young adult mouse ovaries. After fixation in 4% neutral-buffered paraformaldehyde and embedding in paraffin, 6-µm tissue sections were cut from the ovaries and mounted on slides. The sections were de-waxed in xylenes, re-hydrated, and boiled for 5 minutes in 10 mM sodium citrate using a microwave.

Figures 3A, 3B, 3C, 3D:
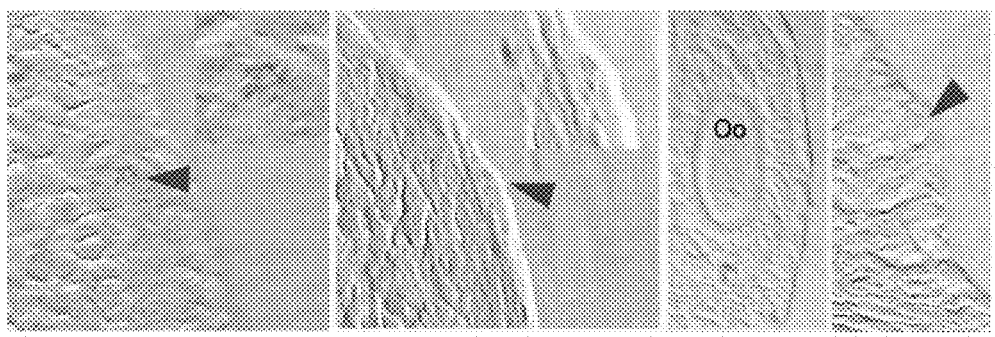
FIG. 3A through FIG. 3D depict SPC3 immunostaining in single cells.

Primary antibodies specific for SCP3 were then used for immunohistochemical analyses per the supplier's recommendations. Normal donkey serum was used in the TNK solution for blocking, and a 1:300 dilution of a goat anti-SCP3 antibody (Walpita, D. et al, (1999) Proc. Natl. Acad. Sci. 96: 5622-5627; Russell, L. B. et al, (2000) Mutat. Res. 464: 201-212) was applied to the sections followed by a biotinylated donkey anti-goat IgG (Santa Cruz Biotechnology) for detection using the streptavidin-peroxidase conjugate system with diaminobenzidine as the colorimetric substrate. To prevent masking of the immunoreactive signal with vital dyes, photomicrographs of the sections were taken under Hoffman optics without prior counterstaining. Immunohistochemical localization of SCP3 revealed individual immunoreactive cells in or proximal to the surface of the ovary (FIGS. 3a and 3b). The possibility that SCP3 was simply carried over as a stable protein product in oocytes formed during the perinatal period was ruled out by the finding that oocytes contained within immature follicles were not immunoreactive (FIGS. 3c and 3d).

Postnatal ovarian expression of SCP3 was confirmed at the messenger RNA level, as was expression of the endonuclease SPO11 and the recombinase DMC1 (FIG. 3e), both of which are also required for the initiation of meiosis in mammals. Additionally, expression levels of genes relating to stem cell function were also examined, such as pum1, pum2, nucleostemin, and mili. Orthologous genes have been identified in *Drosophila* as being central to the maintenance of germline stem cell function in the ovary, such as the RNA binding proteins encoded by piwi and pumilio (Lin, H. (1997) Annu. Rev. Genet. 31: 455-491; Spradling, A. H. et al, (2001) Nature 414: 98-104; Lin, H. (2002) Nature Rev. Genet. 3: 931-940). In *C. elegans*, loss of function of either piwi orthologs (prg-1 and prg-2) or pumilio orthologs (fbf-1 and fbf-2) depletes germline stem cell, and mammalian orthologs of piwi (miwi/hiwi and mili) and pumilio (pumilio-1 and pumilio-2) are known to exist (Cox, D. N. et al. (1998) Genes Dev. 12: 3715-3727; Crittenden, S. L. et al. (2002) Nature 417: 660-663; Kuramochi-Miyagawa, S. et al.

(2001) Mech. Dev. 108: 121-133; Spassov, D. S. & Jurecic, R. (2002) Gene 299: 195-204).

For ovaries collected at each time point and for control tissues, total RNA was extracted and 1 μg of total RNA was reverse-transcribed (Superscript II RT; Invitrogen) using oligo-dT primers. Amplification via 28 cycles of PCR was performed using Taq polymerase and buffer D (Epicentre) with primer sets specific for each gene (see Table 3). The ribosomal gene L7 was co-amplified and used as a loading control for each sample, and 28 cycles were found to be within the linear range of amplification for each experimental primer set.

TABLE 3

Details relating to RT-PCR analyses of gene expression

| Gene | Accession # | Product Size | Primer Sequence (5'-3') | Region Amplified |
|---|---|---|---|---|
| Dmc1 Dmc1-d3 | D64107 | 973 858 (-d) | F: gaaggaggatcaagttgtgc [SEQ ID NO: 1] R: gcttcattttcaggcatctc [SEQ ID NO: 2] | 3-976 |
| L7 | NM_011291 | 199 | F: ggagctcatctatgagaaggc [SEQ ID NO: 3] R: aagacgaaggagctgcagaac [SEQ ID NO: 4] | 209-408 |
| Scp3 | NM_011517 | 436 | F: gagccgctgagcaaacatcta [SEQ ID NO: 5] R: atatccagttcccactgctgc [SEQ ID NO: 6] | 36-472 |
| Spo11a,b | XM_123992; AF163054 | 431(a) 321(b) | F: ccgaggcctcgttcttcgac [SEQ ID NO: 7] R: tgtccaccgcagcctggttc [SEQ ID NO: 8] | 22-453 |
| Mili | AB032605 | 441 | F: tggtactcgagggtggtg [SEQ ID NO: 9] R: cagggctcagatttgcag [SEQ ID NO: 10] | 2304-2745 |
| Nucleostemin | AY181025 | 600 | F: cacaagaagcctaggaaggac [SEQ ID NO: 11] R: ctccaagaagcttccaaaggg [SEQ ID NO: 12] | 120-720 |
| Pum1 | NM_030722 | 497 | F: gcagtgctttggcaggactct [SEQ ID NO: 13] R: ggcactgtctcgccattgatc [SEQ ID NO: 14] | 30-527 |
| Pum2 | NM_030723 | 400 | F: ggagagagactgcatggggaa [SEQ ID NO: 15] R: gcgacttccaggagtgcgatt [SEQ ID NO: 16] | 133-533 |

All PCR products were isolated, subcloned and sequenced for confirmation. In those samples showing more than one amplified product per primer set, each band was isolated, subcloned, and sequenced. These additional bands were determined to be known splice variants of the targeted genes (i.e., Dmc-1/Dmc-1d; Spo11a/Spo11b).

Figures 3E, 3F, 3G:
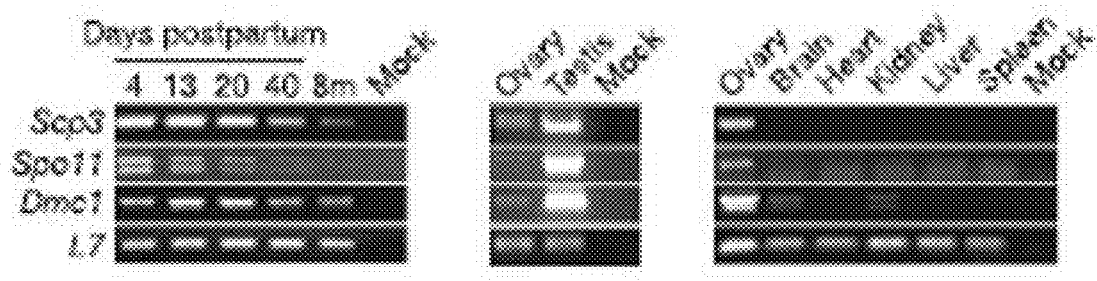
FIG. 3E through FIG. 3G show Scp3, Spo11, and Dmc1 expression in ovaries versus testes, or in various tissues, collected from young adult mice.

Past work has demonstrated that expression of SCP3 and DMC1 in germ cells is restricted to the zygotene or pachytene stages of meiosis. These stages are earlier than the late diplotene stage, where the first meiotic arrest in oocytes is observed. Accordingly, the presence of pre-diplotene mRNA transcripts, like SCP3 protein, reflects expression within cells other than the oocytes presently arrested in meiosis. Expression levels of SCP3, SPO11 and DMC1 ranged from 6% (SPO11 and DMC1) to 25% (SCP3) of those observed in adult testes (FIG. 3f), which is significant considering that daily postnatal germ cell output in the testis far exceeds that estimated for ovaries. Ovarian expression of all three meiosis-related genes declined with age (FIG. 3e), and minimal to no expression of these genes was observed in non-gonadal tissues (FIG. 3g).

Figures 4A, 4B:
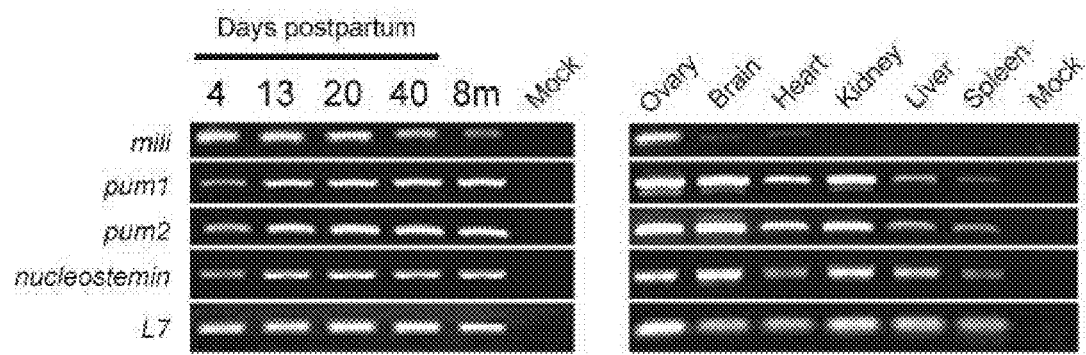
FIG. 4A depicts RT-PCR analysis of mili, pumilio-1 (pum1), pumilio-2 (pum2) and nucleostemin expression in mouse ovaries collected at the indicated days of age or at 8 months (8 m) postpartum.
FIG. 4B shows tissue distribution analysis of the genes in RNA samples prepared from ovaries, brains, hearts, kidneys, lungs and spleens of female mice at 40-42 days of age postpartum.

Analysis of ovaries collected from mice at various times during neonatal, juvenile and adult life revealed expression of mili, pumilio-1 and pumilio-2, with mili showing an age-related decline in its levels of expression (FIG. 4). In addition, expression of nucleostemin, a gene recently implicated in stem cell renewal in mammals (Tsai, R. Y. L. and McKay, R. D. G. (2002) Genes Dev. 16: 2991-3003), was also identified in the mouse ovary during neonatal, juvenile and adult life (FIG. 4).

Example 3: Post-Natal Ovarian Follicle Renewal

The importance of proliferative germ cells to replenishment of the postnatal follicle pool was further verified by the use of busulfan, a germ-cell toxicant widely used in spermatogonial stem cell characterization in male mice. In the testis, busulfan specifically targets germline stem cells and spermatogonia, but not post-meiotic germ cells, leading to spermatogenic failure. Female rodents exposed in utero show a similar gametogenic failure in response to busulfan only if the chemical is given during the window of fetal ovarian germ cell proliferation, as females exposed to busulfan in utero after germ cell proliferation has ceased are born with ovaries that are histologically and functionally similar to ovaries of vehicle-exposed mice.

Figure 5A:
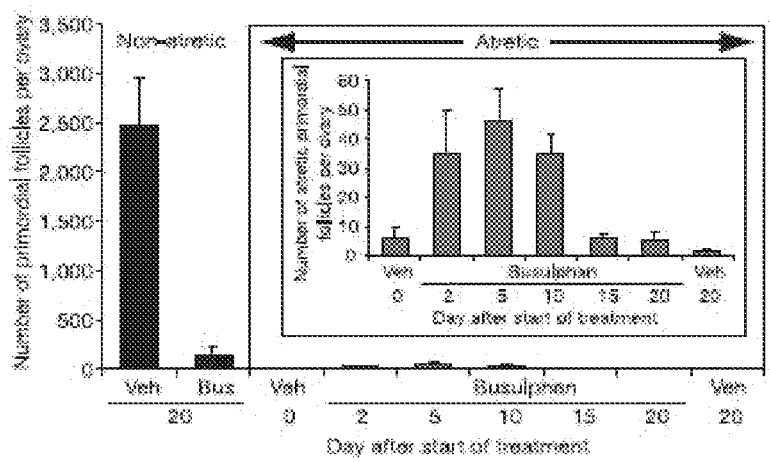
FIG. 5A shows the numbers of non-atretic and atretic primordial follicles present in the ovaries of vehicle, or busulfan-treated mice. The inset shows results for primordial follicle atresia.
Figure 5B:
FIG. 5B through FIG. 5E depict the histological appearance of ovaries of vehicle-treated or busulfan-treated mice.
Figure 5C:
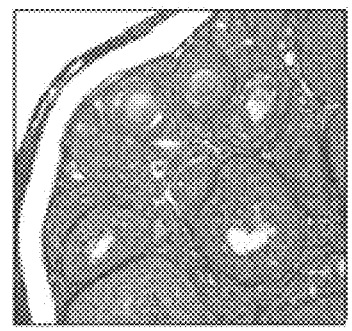
Figure 5D:
Figure 5E:
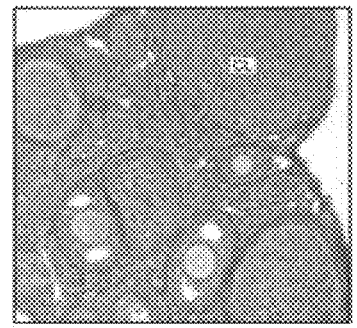

Female mice were injected with vehicle (DMSO) or busulfan (20 mg/kg body weight; resuspended in DMSO) on day 25 and again on day 35 postpartum, and ovaries were collected 10 days after the second injection to analyze changes in non-atretic primordial follicle numbers. Ovaries of females treated with busulfan possessed less than 5% of the primordial follicle pool present in vehicle-treated controls 20 days after the start of the experiment (FIG. 5a). However, busulfan-exposed ovaries retained an otherwise normal histological appearance, including the presence of healthy maturing follicles with non-degenerative oocytes, as well as corpora lutea, indicative of ovulation (FIGS. 5b-5e).

To clarify whether loss of primordial follicles observed in busulfan-treated females (FIG. 5a) results from toxicity to existing oocytes, ovaries were collected from female mice at multiple points during and after the busulfan dosing regimen described above, and they were analyzed for the incidence of primordial follicle atresia. Busulfan caused a slight, transient increase in the number of atretic primordial follicles, with a plateau of only 46 per ovary 5 days after the first injection that quickly declined to basal levels thereafter (FIG. 5a, inset). This relatively minor and acute atretic response to busulfan was negligible considering that over 2,000 primordial follicles were absent in busulfan-exposed ovaries compared with vehicle-treated controls (FIG. 5a). These data reinforce the idea that proliferative germ cells not only persist in the postnatal ovary, but are also required to routinely renew the follicle pool.

To determine the rate of primordial follicle renewal in the postnatal mouse ovary, these results were evaluated in the context of a past investigation of the kinetics of follicle maturation in female mice. Previous analyses demonstrated that the primordial follicle pool is decreased on average by 89 follicles per day, owing to either degeneration or growth activation to the primary stage of development, between days 14 and 42 postpartum (Faddy, M. J. et al, Cell Tissue Kinet. (1987) 20: 551-560). In this a comparable window of time described herein (day 16-40 postpartum; see FIG. 1a), this rate of exit would be expected to reduce the primordial follicle population by 2,136 follicles over this 24-day period. However, the number of primordial follicles declined by only 294 between days 16 and 40 postpartum (FIG. 1a). The difference between these two values, or 1,842 primordial follicles, represents the rate of primordial follicle renewal over this 24-day period, yielding an average of 77 new primordial follicles per ovary per day. Given this calculation, the rate of primordial follicle depletion per day should be the difference between the rate of exit per day provided by previous analyses (89 follicles) and the rate of renewal per day (77 follicles), for a net loss of 12 primordial follicles per ovary per day. Using this value, the primordial follicle pool would be expected to decline between days 16 and 40 postpartum by a total of 288 follicles, a number very close to that derived from comparing the actual counts of non-atretic primordial follicles on day 16 versus day 40 (2,334 versus 2,040, or a net loss of 294 primordial follicles; FIG. 1a).

Thus, taken together, busulfan treatment causes a 95% reduction in the resting (primordial) oocyte pool in female mice within three weeks, and this effect is not due to either enhanced atresia of the primordial oocyte pool.

Figure 6:
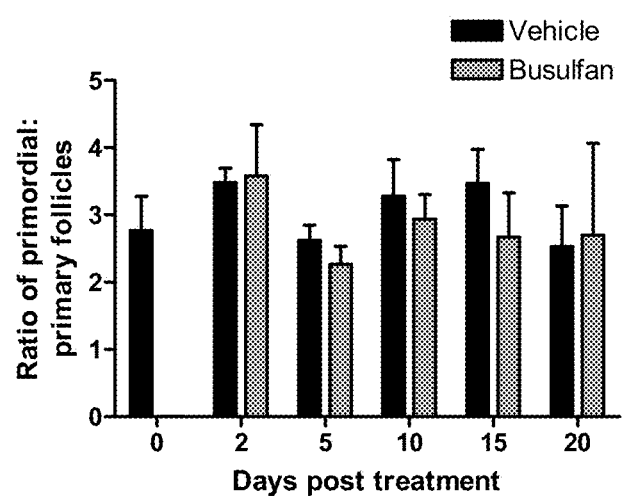
FIG. 6 is a graph showing the ratio of primordial to primary follicles in evaluation of the long-term outcome of anti-cancer treatment (busulfan) on ovarian function in mice. The calculation of this ratio allows for the estimation of the rate of loss of primordial follicles via growth activation.
Figure 7A:
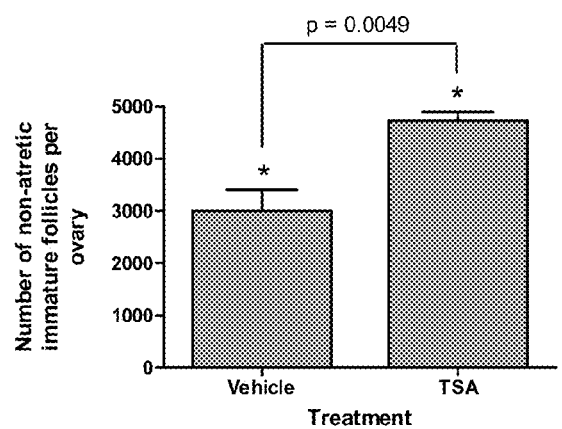
FIG. 7A shows the numbers of non-atretic immature follicles in response to vehicle or TSA, while FIG. 7B quantifies the numbers of resting (primordial) and early growing (primary and small preantral) follicles
Figure 7B:
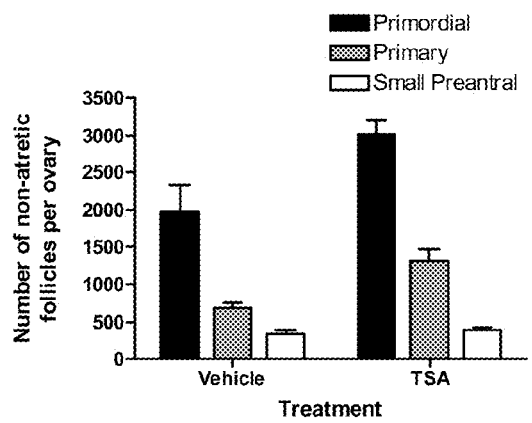
Figure 8A:
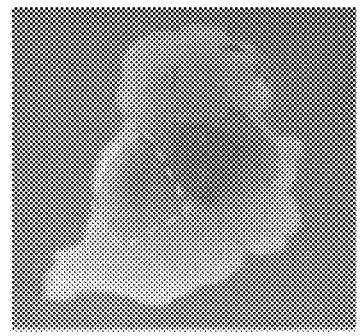
FIGS. 8A and 8B show that wild-type ovarian tissue adheres to green fluorescent protein (GFP)-transgenic host ovarian tissue and becomes vascularized. Gross morphology of a representative ovarian graft at 3-4 weeks post-surgery, prior to (FIG. 8A) and after (FIG. 8B) removal from the bursal cavity.
Figure 8B:
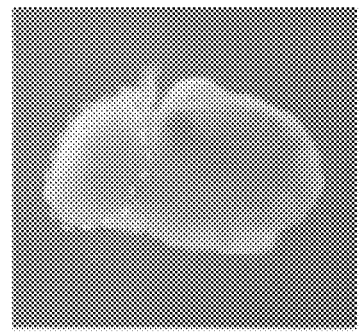
Figure 8C:
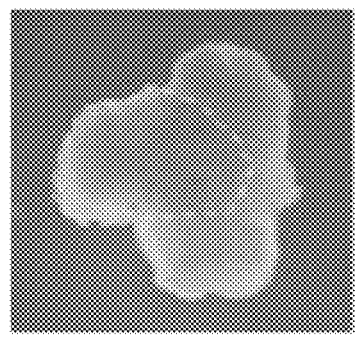
FIG. 8C through FIG. 8F show the gross histological appearance of representative ovarian grafts (broken white line) as viewed under light (FIG. 8C, FIG. 8E) and fluorescence (GFP; F) microscopy at 3-4 weeks post-surgery.
Figure 8D:
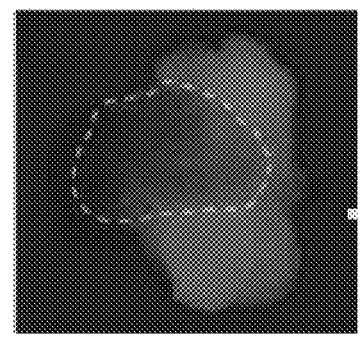
Figure 8E:
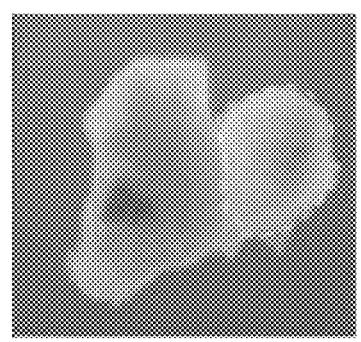
Figure 8F:
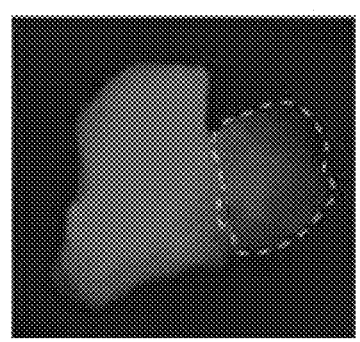

Although there was no precedence in the literature for busulfan inducing the growth activation of primordial follicles, and no morphological evidence for such an outcome was observed, the number of (growth-activated) primary follicles during the time course has been determined and the average ratio of primordial follicles to primary follicles over the time course has been calculated. No significant change in the ratio of primordial to primary follicles was seen between busulfan and vehicle treatment (FIG. 6), indicating that busulfan treatment did not decrease the primordial pool by increasing follicle growth activation. These data further support the conclusion that busulfan specifically depletes germline stem cell support of oocyte production in the ovaries resulting in a gradual loss of the primordial follicle pool through an absence of oocyte and follicle renewal.

The long-term outcome of anti-cancer treatment on ovarian function in human females was also studied. Chemotherapy regimens containing busulfan result in a near-total incidence of premature ovarian failure (POF), regardless of other drugs used in combination therapy. For example, clinical data combined from three studies showed that 20 of 21 adolescent girls (mean age=11.5) treated with chemotherapeutic regimens containing busulfan experienced hypogonadism indicative of POF, while comparable treatments that lacked busulfan caused POF in only 22 of 37 girls (mean age=8.7) (Thibaud, E. et al, (1998) Bone Marrow Transplant. 21: 287-290; Teinturier, C. et al, (1998) Bone Marrow Transplant. 22: 989-994; Afify, Z. et al, (2000) Bone Marrow Transplant 25: 1087-1092). Similarly, 4 of 4 pubertal girls (mean age=13) treated with busulfan in combination therapy showed ovarian damage requiring hormonal replacement (Legault, L. and Bonny, Y. (1999) Pediatric Transplant 3: 60-66). In yet another study, busulfan treatment in women between the ages of 16 and 40 (median age=30) caused POF in 19 of 19 cases (Sanders J. E. et al, (1996) Blood 87 3045-3052). Moreover, in a study where combined busulfan and cyclophosphamide therapy was compared to cyclophosphamide alone, 72 or 73 patients treated with both agents exhibited POF (ages 14-57, median=38) while cyclophosphamide alone resulted in POF in 47 of 103 patients (ages 13-58, median=28) (Grigg, A. P. et al, (2000) Bone Marrow Transplant 26: 1089-1095).

Exposure to busulfan resulted in POF in 115 of 117 patients, while comparable chemotherapy treatments lacking busulfan were associated with POF in only 69 of 140 cases. While busulfan treatment may cause POF in humans by accelerating oocyte loss (death), based on the findings with busulfan in female mice, the results from these clinical trials with busulfan may also indicate an irreversible destruction of human female germline stem cells leading to POF.

The existence of mammalian female germline stem cells implies an inherent capacity of the ovaries to generate, or regenerate following an insult, new stockpiles of resting (primordial) oocyte-containing follicles in a regulated fashion. To address this issue directly, adult female mice were injected with doxorubicin to synchronize oocyte death (Perez, G. I. et al, (1997) Nature Med. 3, 1228-32), and ovaries were collected at multiple intervals after drug exposure to assess germ cell dynamics. As expected, a rapid and extensive loss of primordial and early growing follicles (oocytes) occurred within the first 24 h after doxorubicin treatment (data not shown). However, a spontaneous regeneration of both the primordial and total immature follicle pools was observed between 24 and 36 h post-treatment, and the number of oocyte-containing immature follicles stabilized thereafter (data not shown).

To further show that the adult mammalian ovary is fully capable of de-novo oocyte production, a recent report showing that inhibition of histone deacetylation rapidly expands haematopoietic stem cells (Milhem, M. et al. (2004) Blood 103, 4102-4110) was used as a basis to test whether acute in-vivo suppression of histone deacetylase (HDAC) activity could similarly enhance germline stem cell function. Prepubertal female mice were given a single intraperitoneal injection of the broad-spectrum histone deacetylase inhibitor, Trichostatin A (TSA; 10 mg/kg body weight, resuspended in DMSO), or vehicle (DMSO). Animals were sacrificed 24 hours post-injection, histological preparations of ovaries were prepared, and oocyte-containing follicles were counted per standard laboratory procedures (see Example 1). Treatment with TSA caused a 53% increase in the number of total healthy immature oocyte-containing follicles per ovary when compared with ovaries of control mice given the vehicle treatment. Not only was the resting (primordial) pool of follicles increased by 42%, but also the number of early growing (primary) follicles was increased (data).

Treatment with TSA either reduced the incidence of mature follicle loss (death or atresia) or increased new oocyte and follicle production by germline stem cells. Since the average baseline level of immature follicle atresia in untreated 13-day old mice is 16±4 (n=4), a decrease in the rate of atresia cannot explain the large increase (more than 1,600) in healthy immature follicles. Without new oocyte production, an increase in the number of primordial oocyte-containing follicles is impossible. Notably, should the production of new oocytes not occur, the increase in primary follicles must be subtracted from their source, i.e. the number of primordial follicles. As the number of primordial follicles does not decrease but instead increases, the only explanation for the dramatic increase in oocyte and follicle numbers following TSA exposure is a significant new production of immature oocytes from germline stem cells.

More striking results were obtained in adults, in that TSA increased primordial follicle numbers in female mice at 240 days of age by 89% within 24 h (data not shown). Since the observed increases could not be attributed to either a reduced rate of primordial follicle growth activation to the primary stage of development (data not shown) or a reduced incidence of atresia (data not shown), these data provide additional evidence that oogenesis and folliculogenesis persist during adult life in mammalian females.

Example 4: Evidence of Post-Natal Ovarian Folliculogenesis

Figure 9A:
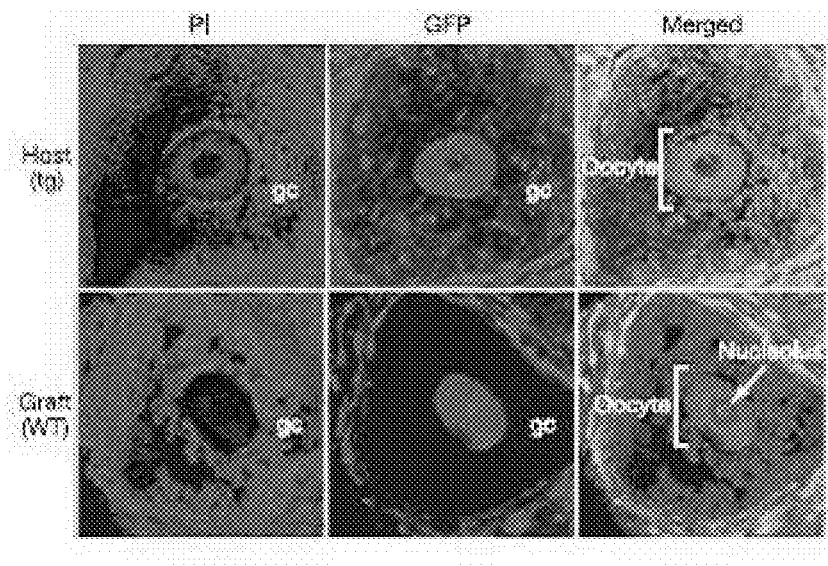
FIG. 9A and FIG. 9B show GFP expression in sections of host (GFP-transgenic) and grafted (wild-type) ovarian tissues counterstained with propidium iodide.
Figure 9B:
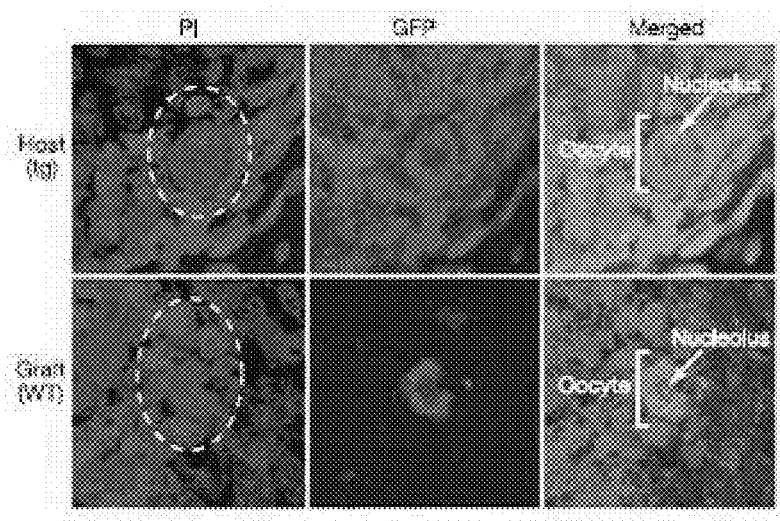
Figure 10:
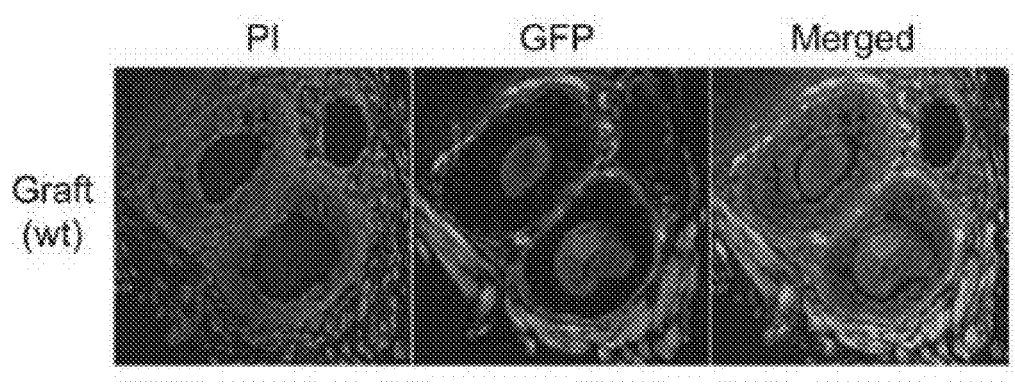
FIG. 10 is an additional example of folliculogenesis in grafted ovarian tissue. Two adjacent immature follicles composed of GFP-transgenic oocytes and wild-type granulosa cells present within wild-type (wt) ovarian tissue 4 weeks after grafting into the ovarian bursal cavity of a GFP-transgenic recipient female (PI, propidium iodide counterstaining).

Transgenic mice with ubiquitous expression of GFP (obtained from Jackson laboratories, strain STOCK TgN (GFPU)5Nagy) were used to provide additional evidence for ongoing folliculogenesis in postnatal life. Heterozygous transgenic male and female mice with ubiquitous expression of GFP were mated to generate wild-type and transgenic female offspring for intrabursal ovarian grafting. Briefly, young adult (58-69 days postpartum) transgenic female mice were anesthetized (avertin, 200 mg per kg, intraperitoneal) to expose one of the two ovaries in each mouse through dorso-lateral incisions. For each animal, a small hole was cut in the ovarian bursa laterally near the hilus, and approximately one-half of the host ovary was removed in preparation for grafting. Ovaries collected from donor (wild-type littermate) female mice were bisected, and one-half of a wild-type ovary was placed within the transgenic recipient's bursal cavity in contact with the remaining host ovarian tissue. The reproductive tract was then allowed to settle back into the peritoneal cavity and the incision was closed. A total of six transgenic hosts were used for this experiment, four of which received unilateral wild-type ovarian grafts while the remaining two received bilateral wild-type ovarian grafts. Between 3-4 weeks after surgery, the ovarian tissues were removed and processed for GFP visualization, after propidium iodide counterstaining, by confocal laser scanning microscopy. The grafted ovarian fragments, upon gross visual inspection, showed evidence of neovascularization and adhesion to the host ovarian tissue (FIG. 8). Confocal microscopic analysis revealed follicle-enclosed, GFP-positive oocytes in the wild-type ovarian fragments that were indistinguishable from follicle-enclosed oocytes in the host ovarian tissue (FIGS. 9 and 10). Moreover, the granulosa cells enveloping the GFP-positive oocytes in the grafts were negative for GFP, indicating that transgenic germ cells had infiltrated the grafted tissue and initiated folliculogenesis with the resident wild-type somatic cells.

To sustain the addition of new primordial follicles during juvenile and adult life, the mouse ovary must possess either a small pool of asymmetrically dividing germline stem cells or a large pool of non-renewing, pre-meiotic germ cells that produce oocytes after symmetric divisions. Histomorphometric studies at day 30 postpartum revealed the presence of 63±8 such cells per ovary (mean±standard error, n=4 mice), a number close to that expected for a small pool of asymmetrically dividing germ cells.

Example 5: Oocyte Dynamics in Transgenic Mouse Models

Figure 11A:
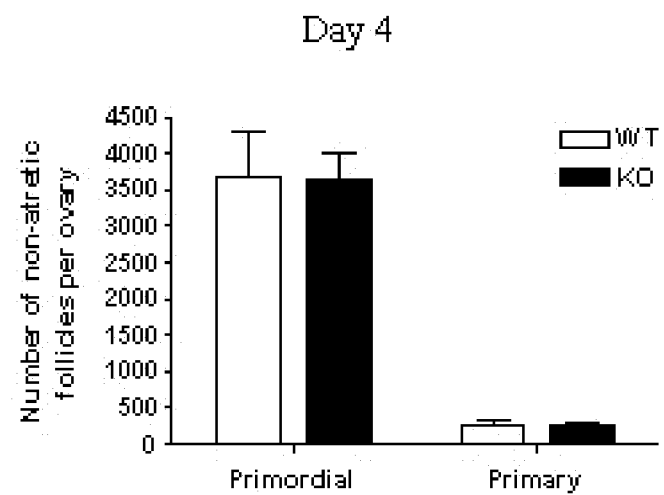
FIGS. 11A-11C show graphs depicting oocyte dynamics in Bax deficient (gene knockout, KO) female mice.
Figure 11B:
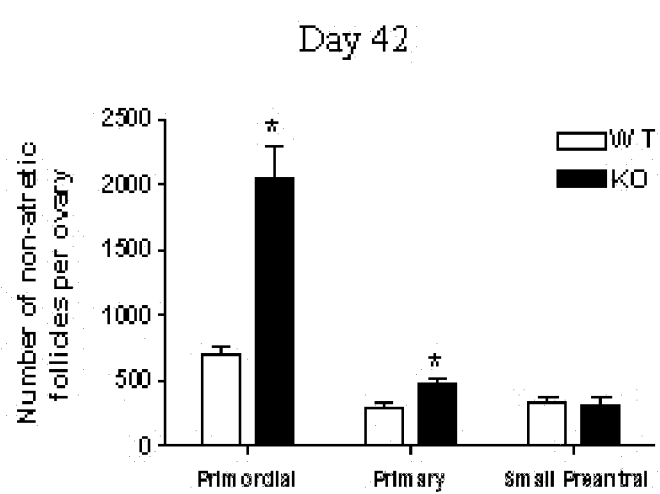
Figure 11C:
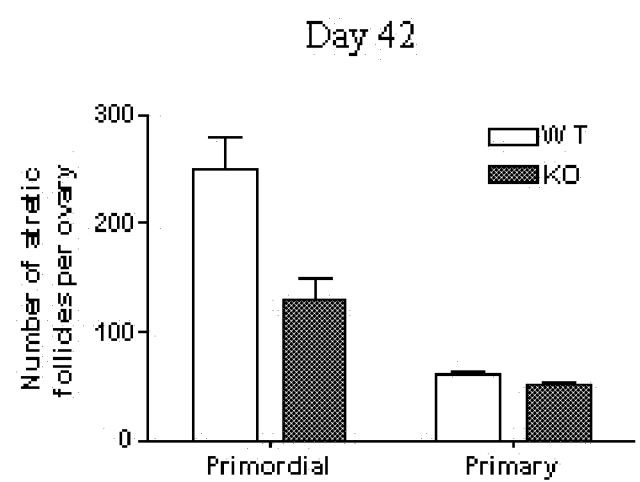

Published data from the analysis of oocyte dynamics in the Bax knockout mouse (Perez et al., (1999) Nature Genetics 21: 200-203), and unpublished contemporary data from the Caspase-6 knockout mouse was re-evaluated and compared in view of the results demonstrating post-natal oocyte folliculogenesis presented herein. Data shown here provide additional evidence of germline stem cell function and, for the first time, reveal the effects of these apoptosis regulatory gene knockout mice upon germline stem cell production of new oocytes. Histological preparations of ovaries were prepared, and oocyte-containing follicles were counted per standard laboratory procedures (Tilly, J. L. (2003) Reprod Biol Endocrinol 1: 11; see also Example 1). The Bax protein has been shown to be a crucial pro-apoptotic molecule within somatic cells in the ovary and in oocytes (Tilly, J. L. (1996) Rev Reprod 1: 162-172; Perez, G. I. et al., (1997) Nature Med. 3: 1228-1232). Bax knockout mice were shown to have greatly extended ovarian function, with 200 to 300 non-atretic follicles present in the ovaries of 20-22 month-old females compared to essentially zero in age-matched wild-type controls. Data comparing immature follicles numbers during early postnatal life (Day 4) and early reproductive adulthood are shown above. While oocyte endowment in early life is comparable between Bax-null and wild-type mice, Bax-null mice have nearly 2.5 times greater primordial follicles at Day 42 than wild-type, and a significantly greater number of primary follicles as well (FIG. 11). Concurrent measurement of atresia, or death, in these mice at Day 42 revealed a major decrease in primordial follicle atresia. Thus, the Bax-null mice fail to eliminate the normal number of primordial follicles in comparison to wild-type mice.

Figure 12A:
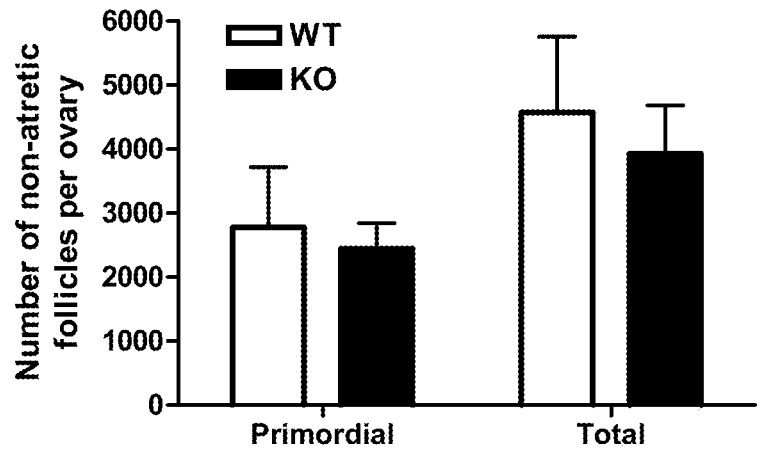
FIGS. 12A-12C shows graphs depicting oocyte dynamics in Caspase-6 deficient (gene knockout, KO) female mice.
Figure 12B:
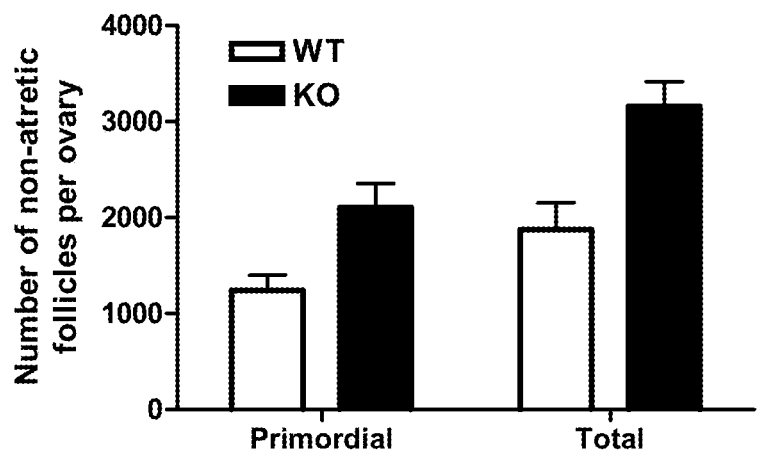
Figure 12C:
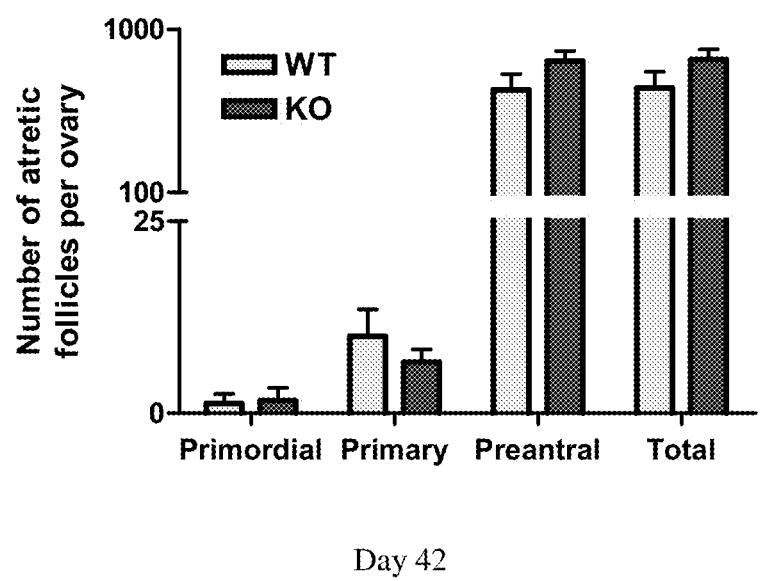
Figure 13A:
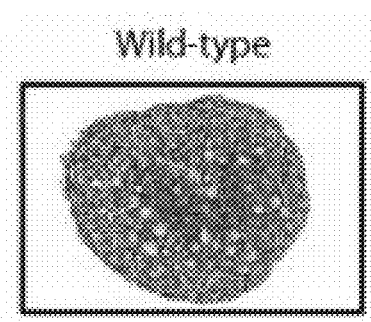
FIGS. 13A-13E depict the representative histology of postpartum day 4 wild-type (FIG. 13A, magnified in FIG. 13C) and Atm (ataxia telangiectasia gene mutated)-deficient (FIG. 13B, FIG. 13D) ovaries. RT-PCR analysis shows the presence of germline markers in both wild-type and Atm-null ovaries (FIG. 13E).
Figure 13B:
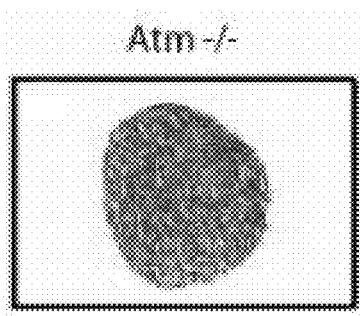
Figure 13C:
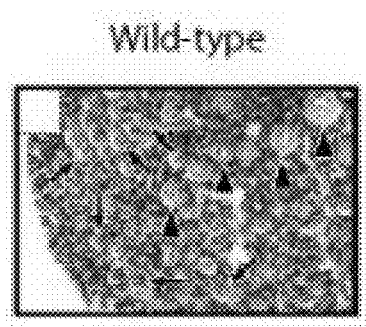
Figure 13D:
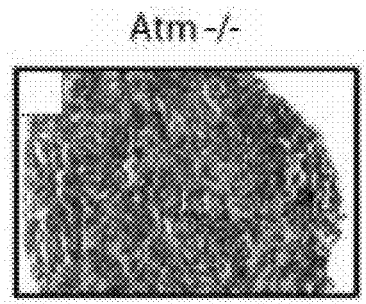
Figure 13E:
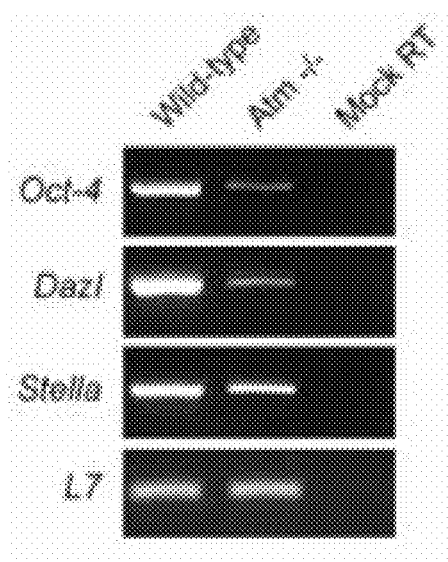
Figure 14A:
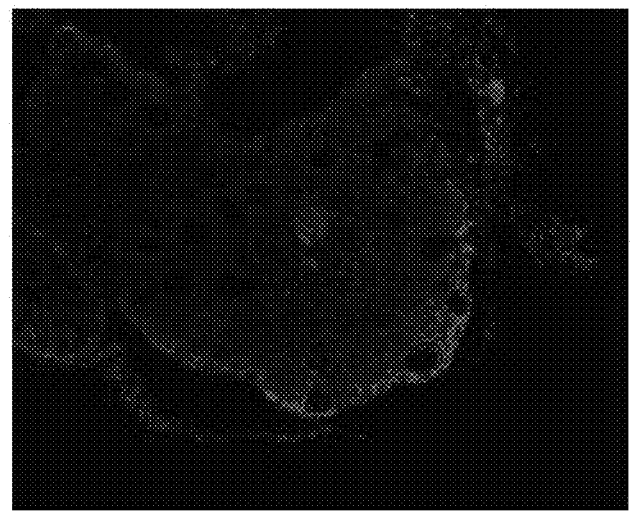
FIGS. 14A-14D depict immunohistochemical analysis of SSEA1 expression (red, with nuclei highlighted by propidium iodide in blue) in adult mouse ovaries (FIG. 14B, higher magnification of SSEA1+ cells shown in FIG. 14A.
Figure 14B:
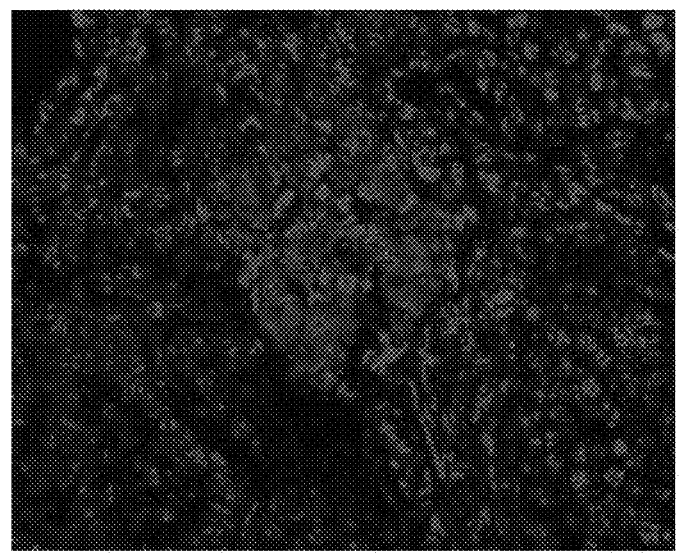
Figure 14C:
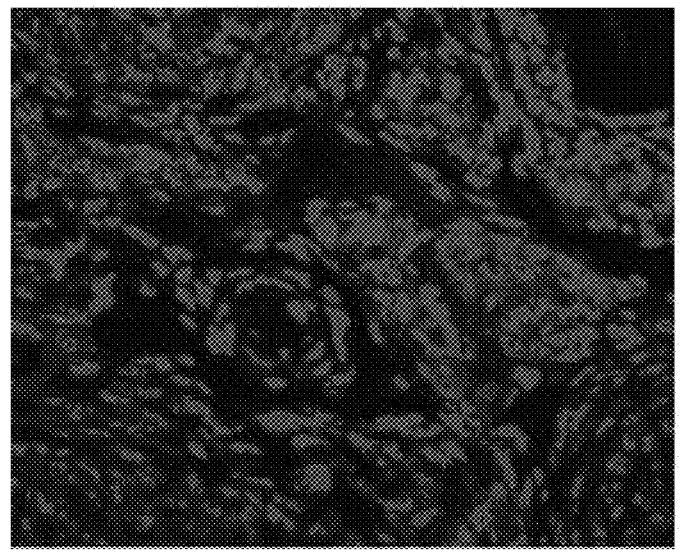
Figure 14D:
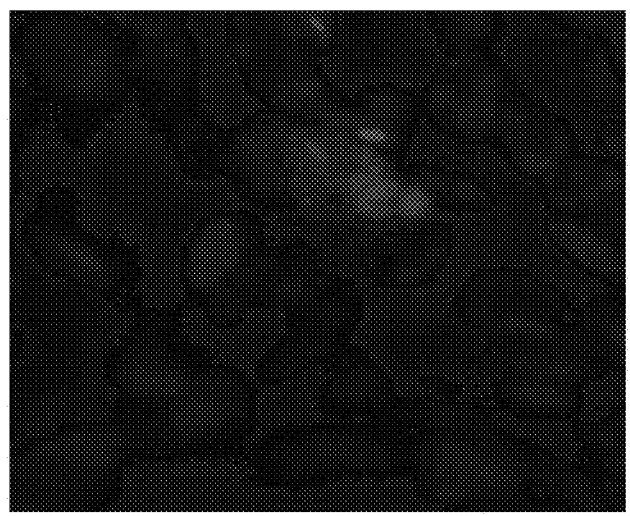

Caspase-6 is also a pro-apoptotic molecule, functioning as a protease that cleaves structural intracellular targets during the onset of apoptosis (Ruchaud, S. et al. (2002) EMBO J. 21: 1967-1977). The mouse knockout of Caspase-6 does not result in an overt phenotype. Recently, however, Caspase-6-null mice were shown to demonstrate an ovarian phenotype similar to Bax-null mice, in that Day 4 similar numbers of immature follicles are present in both Caspase-6-null ovaries and those of wild-type mice (FIG. 12). Caspase-6-null mice also have a significant increase in the number of primordial and a large increase in the number of total immature follicles at Day 42 of life. However, when immature follicle atresia was measured in these mice at Day 42, unlike the Bax-null mouse, Caspase-6-null mice show no change in the amount of atresia. Since a decrease in the amount of atresia is not seen, the only other explanation for the increase in follicle numbers in Caspase-6-null mice is an increase in the production of new oocytes due to the deletion of Caspase-6. Caspase-6 is therefore a regulator of germline stem cell apoptosis.

As shown herein, Bax is a regulator of oocyte death. Given that primordial follicle atresia is only halved in Bax-null mice, and that Bax-null ovaries contain oocytes for as many as 10 to 14 months longer than wild-type ovaries, Bax also regulates germline stem cell apoptosis. In contrast, Caspase-6 can be directly seen to regulate germline stem cell function/death but does not regulate oocyte death. Thus, Caspase-6 and Bax are regulator(s) of oocyte production at the level of oocyte-progenitor germline stem cells. Modulating germline stem cell function by modulating the function of key apoptotic regulators in vivo is thus an important strategy for the extension of ovarian function in mammals.

To further demonstrate the existence of postnatal female germline stem cells, the ovaries of wild-type mice were compared with ovaries from Ataxia-telangiectasia mutation (Atm) gene-deficient mice. Atm-deficient male and female mice have been shown to be infertile due to the complete loss of the production of mature gametes, e.g. sperm and oocytes (Barlow, C. et al. (1996) Cell 86: 159-171). Atm-deficiency was shown to result in aberrant early stages of meiosis, detected as early as the leptotene stage, that results in increased apoptosis of developing gametes (Barlow, C. et al. (1998) Development 125: 4007-17) and therefore total gamete loss. Ovaries from Atm-deficient females were shown to be completely barren of oocytes and follicles by 11 days of age (Barlow, C. et al. (1998) Development 125: 4007-17). Representative histology of postpartum Day 4 wild-type (FIG. 13A, magnified in C) and Atm-null (FIG. 13B, D) ovaries is depicted in FIG. 13. Thus, if all oocyte production has occurred prenatally and has resulted in a fixed pool of diplotene oocytes within primordial follicles at birth, and Atm-deficiency results in a complete lack of oocytes, no germline or oocyte marker gene expression should occur in these "barren" ovaries. However, due to detection of germline stem cells in the postnatal female ovary, pre-meiotic germline stem cells can be present and capable of self-renewal, but ongoing oocyte production is impossible due to meiotic entry in the absence of Atm. The expression of germline markers in the Atm-deficient ovary versus wild-type controls was performed by reverse-transcription followed by PCR and representative data (n=3) is shown in FIG. 13, right panel. As predicted, the pluripotency marker Oct-4 (Brehm, A. et al. (1998) APMIS 106: 114-126) and the germline markers Dazl (McNeilly, J. R. et al. (2000) Endocrinology 141: 4284-4294; Nishi, S. et al. (1999) Mol Hum Reprod 5: 495-497) and Stella (Bortvin, A. et al. (2004) BMC Dev Biol 23: 2) are all expressed in the Atm-deficient ovary at postnatal Day 71. Semi-quantitative comparison of the relative levels of these genes by examination of the loading control L7 shows that, as expected, these genes are expressed at much lower levels than in wild-type ovaries containing oocytes. The contralateral ovary in each animal used for RT-PCR analysis was prepared for histology, and the sampling and examination of histological sections from Atm-null mice did not reveal any oocytes or structures resembling follicles as expected. Thus, Atm-deficiency results in a pool of germline stem cells that may renew until at least several weeks of adult life (Day 71) but may not, as reported, produce viable oocytes due to the meiotic defect that results in gamete death.

Example 6: Isolation and Characterization of Cells from Adult Mouse Ovaries

Stage-Specific Embryonic Antigen-1 (SSEA-1) has been shown to decorate the surface of specialized mammalian cells, notably embryonic stem cells (Henderson, J. K. et al., (2002) Stem Cells 20: 329-37; Furusawa, T. et al., (2004) Biol Reprod. 70: 1452-7) and primordial germ cells ("PGC") (Matsui, Y. et al., (1992) Cell 70: 841-7; Gomperts, M. et al., (1994) Development. 120: 135-41). Thus, SSEA-1 was a potential marker for female germline stem cells and their progenitors. Furthermore, fetal PGC expression of SSEA-1 correlates with the well-established developmental period in which germ cells (female and male) are pre-meiotic and able to divide. By extension, postnatal female germline stem cells, also pre-meiotic and able to divide, could also express SSEA-1.

Immunohistochemical detection of SSEA-1 in the mouse ovary (adult and prepubertal) revealed a small central population of SSEA-1 positive cells in the core or medullary region of the ovary (FIG. 14). However, outside of a low level of immunoreactivity occasionally observed in some scattered granulosa cells, SSEA1 was not expressed in any other area of the ovary or in any cell type of known origin, including oocytes. These cells are otherwise unremarkable when compared morphologically to neighboring cells, which share their stromal appearance; SSEA-1 immunoreactivity now reveals their stem cell properties. SSEA-1 was therefore selected as a marker to be used in the isolation of this population of cells expected to be postnatal female germline stem cells or the progenitors thereof.

Figure 15:
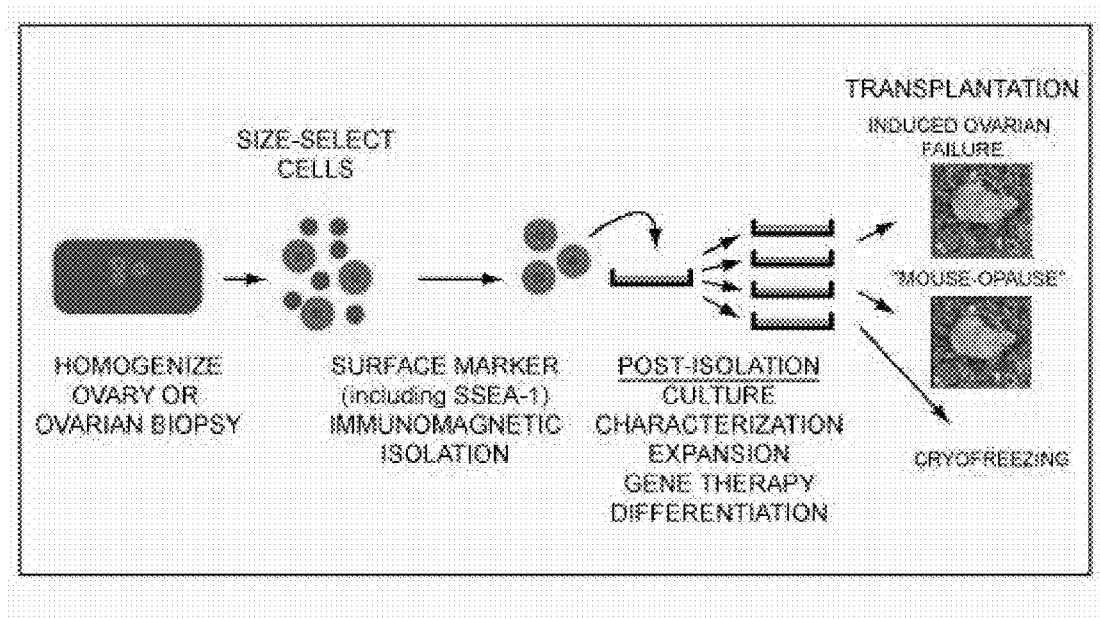
FIG. 15 depicts a schematic presentation of one strategy for the isolation of female germline stem cell and/or their progenitors.

A strategy for the isolation is schematically shown in FIG. 15. Adult ovaries (postnatal day 51) were removed and homogenized as follows. Each ovary was placed in 250 µl DMEM media (Gibco #11995-06), pre-warmed to 37° C., and was torn apart with a syringe needle and forceps. Care was taken to leave macroscopic growing follicles intact, and maximal disruption of medullary/stromal structures was attempted. Two-hundred-and-fifty µl of pre-warmed 2×-concentrated homogenization medium (DMEM+1 mg/ml collagenase [Gibco #17100-017]) was added to the dish containing the disrupted ovary, and tissue/media were transferred to a 15 ml conical tube. Tissues in homogenization media were incubated with shaking for 45 minutes at 37° C. The digested tissue and cells were spun through a 40-micron cell strainer for 10 minutes at 1000×g. Medium was removed, and the pelleted cells from each homogenized ovary were re-suspended in 500 µl phosphate buffered saline ("PBS")-0.1% bovine serum albumin ("BSA") and cooled to 4° C. prior to subsequent immunomagnetic separation.

The cells were isolated from the ovarian homogenate using anti-mouse IgM beads (Dynabeads M-450 Rat anti-mouse IgM; Dynal Biotech), pre-coated by adding 3 µg of anti-SSEA-1 antibody per 50 µl aliquot of beads and incubating for 15 minutes at 4° C. with rocking. Coated beads were washed 3 times with PBS-0.1% BSA and pelleted using the Dynal MPC, and then resuspended in PBS-0.1% BSA. Afterwards, 12.5 µl of coated beads were then added to each 500 µl aliquot of ovarian cells. Cells and beads were incubated with gentle rocking at 4° C. for 30 minutes. Cells bound to the beads were isolated by washing 3 times in PBS-0.1% BSA after pelleting with the Dynal MPC. After the last separation, the supernatant was removed and the beads, including bound cells, were resuspended in 250 µl Tri Reagent (Sigma, T9424), vortexed, and stored at −80° C. prior to RNA isolation.

The SSEA-1 positive, isolated cellular fraction was used for reverse-transcription of messenger RNA/polymerase chain reaction amplification (RT-PCR) to determine their gene expression profile. Total RNA was extracted from each sample and 1 µg was reverse transcribed (Superscript II RT; Invitrogen) using oligo-dT primers. Amplification via 28-35 cycles of PCR was then performed using Taq polymerase and Buffer-D (Epicentre) with primer sets specific for each gene (Table 4a, b). For each sample, RNA encoded by the ribosomal gene L7 was amplified and used as a loading control ('house-keeping' gene). All PCR products were isolated, subcloned and sequenced for confirmation.

TABLE 4a

RT-PCR analysis of gene expression in mouse tissues

| Gene | Accession # | Product Size | Primer Sequence (5'-3')[1] | Region Amplified[2] |
|---|---|---|---|---|
| Dazl | NM_010021 | 317 | F: gtgtgtcgaagggctatggat [SEQ ID NO: 17]<br>R: acaggcagctgatatccagtg [SEQ ID NO: 18] | 230-547 |
| Fragilis | NM_025378 | 150 | F: gttatcaccattgttagtgtcatc [SEQ ID NO: 19]<br>F: aatgagtgttacacctgcgtg [SEQ ID NO: 20] | 355-505 |
| Gdf9 | L06444 | 708 | F: tgcctccttccctcatcttg [SEQ ID NO: 21]<br>R: cacttcccccgctcacacag [SEQ ID NO: 22] | 747-1454 |
| Hdac6 | NM_010413 | 383 | F: acgctgactacattgctgct [SEQ ID NO: 23]<br>R: tctcaactgatctctccagg [SEQ ID NO: 24] | 944-1327 |
| L7 | NM_011291 | 199 | F: ggagctcatctatgagaaggc [SEQ ID NO: 3]<br>R: aagacgaaggagctgcagaac [SEQ ID NO: 4] | 209-408 |
| Mvh | NM_010029 | 212 | F: ggaaaccagcagcaagtgat [SEQ ID NO: 25]<br>R: tggagtcctcatcctctgg [SEQ ID NO: 26] | 479-691 |
| Oct4 | X52437 | 589 | F: cccaagttggcgtggagactt [SEQ ID NO: 27]<br>R: cttctggcgccggttacagaa [SEQ ID NO: 28] | 158-747 |
| Scp3 | NM_011517 | 436 | F: gagccgctgagcaaacatcta [SEQ ID NO: 5]<br>R: atatccagttcccactgctgc [SEQ ID NO: 6] | 36-472 |
| Stella | AY082485 | 353 | F: cccaatgaaggaccctgaaac [SEQ ID NO: 29]<br>R: aatggctcactgtcccgttca [SEQ ID NO: 30] | 27-380 |

TABLE 4a-continued

RT-PCR analysis of gene expression in mouse tissues

| Gene | Accession # | Product Size | Primer Sequence (5'-3')[1] | Region Amplified[2] |
|------|-------------|--------------|----------------------------|---------------------|
| Zp3 | M20026 | 182 | F: ccgagctgtgcaattcccaga [SEQ ID NO: 31] R: aaccctctgagccaagggtga [SEQ ID NO: 32] | 50-232 |

The SSEA-1 isolated fraction shown in FIG. 16 is a fraction of cells that express genes denoting pluripotency (Oct-4: Brehm, A. et al., (1998) APMIS 106: 114-126), and placing their lineage within the germline (Dazl: McNeilly, J. R. et al., (2000) Endocrinology 141: 4284-4294, Nishi, S. et al., (1999) Mol Hum Reprod 5: 495-497; Stella: Bortvin, A. et al., (2004) BMC Dev Biol 23: 2; and the mouse Vasa homologue, Mvh: Fujiwara, Y. et al. (1994) *Proc. Natl. Acad. Sci. USA* 91, 12258-12262). This fraction does not express genes found in either growing oocytes (e.g., GDF-9: Dong, J. et al., (1996) Nature 383: 531-535; and ZP3: Dean, J. (2002) J. Reprod. Immunol. 51(1-2) 171-80) or in resting primordial oocytes (e.g., HDAC6) (FIG. 16). All of these genes are, as expected, expressed in the SSEA-1 depleted fraction of cells as this fraction contains oocytes. Moreover, since the SSEA-1 isolated fraction of cells does not express genes found in either resting primordial oocytes or growing oocytes, this fraction is not contaminated with oocytes. In addition, these cells also do not express the synaptonemal complex protein SCP3, a marker of meiotic entrance (Yuan, L. et al., 2000 Mol Cell 5: 73-83; Johnson, J. et al., 2004 Nature 428: 145-150) supporting their identification as female germline stem cells and/or their progenitors.

Separately, live female germline stem cells and/or their progenitors were isolated from previously described ovarian homogenates (see above) using the above methodology with slight modifications. In this case, the anti-SSEA-1 antibody was biotinylated through the long-chain N-hydroxysuccinimide ester of biotin with primary amine reactivity (NHS-LC-biotin). For a full overview of biotinylation procedures, see the Pierce Catalogue and Handbook (Pierce, Rockford, USA).

The CELLection biotin binder kit from Dynal Biotech was then used to isolate the SSEA-1 positive cells. The CELLection beads are preferable where post-isolation removal of affinity beads from the cells is desired. The methods are briefly described as follows. CELLection beads were re-suspended thoroughly and 50 µl aliquots were transferred to a tube suitable for the Dynal MPC. The tube was placed in the Dynal MPC for 1 minute, removed and 1-2 ml buffer (e.g., PBS with 0.1% Tween-20) was added for re-suspension.

To coat the beads with biotinylated anti-SSEA-1 antibody, 2-3 µg of biotinylated antibody and 50 µl of beads were combined in a tube and rotated for 30 minutes at room temperature. The tube was then placed in the Dynal MPC for 1 minute to pellet the beads coated with anti-SSEA-1 antibody. The beads were washed with 1 ml PBS with 0.1% Tween-20, and pelleted using the Dynal MPC, three times. Coated beads were re-suspended in the original volume of PBS with 0.1% BSA, giving a final concentration of $4 \times 10^8$ beads/ml (note that 0.02% sodium azide can be optionally added as a preservative).

As detailed above, cells from one ovary were re-suspended in 500 µl PBS-0.1% BSA and cooled to 4° C., after which 12.5 µl of anti-SSEA-1 coated beads was combined with each 0.5 ml ovary homogenate sample. Cells and beads were incubated with gentle rocking at 4° C. for 30 minutes. Cells bound to the beads were isolated by washing 3 times in PBS-0.1% BSA after pelleting with the Dynal MPC. The tube was removed from the Dynal MPC and rosetted cells were combined with RPMI 1640 (containing 1% FCS). Rosetted cells were re-suspended by pipetting, transferred to a new vial and placed in the Dynal MPC for 1 minute. The tube was removed from the Dynal MPC and cells were resuspended by pipetting the rosetted cells in a minimum of 500 µl RPMI (containing 1% FCS). This step was repeated twice. After the final wash, the fluid was removed and the rosetted cells were re-suspended in RPMI (1% FCS) pre-warmed to 37° C. Releasing buffer was added at 2 µl, and the mixture was incubated for 15 minutes at room temperature with gentle tilting and rotation. Rosettes were flushed vigorously through a pipette 8 times, and then placed in the Dynal MPC for 1 minute. Supernatant containing the released cells was pipetted to a new test tube containing 200 µl RPMI (with 10% FCS). Aliquots of cells (e.g., 50-100 µl) were collected and stored for future use for in vitro culture and transplantation to recipient animals.

Figure 17:
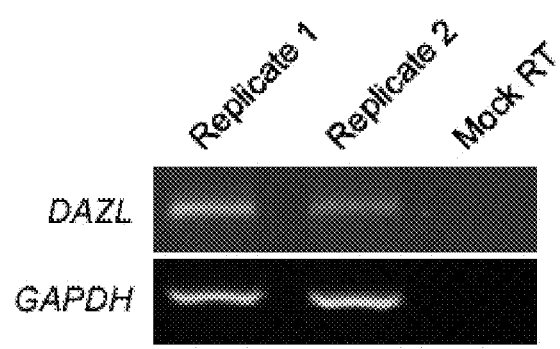
FIG. 17 depicts expression of Dazl in human umbilical cord blood, as detected by RT-PCR analysis.

Example 7: Female Germline Stem Cells in Peripheral Blood Derived from the Umbilical Cord Human cord blood was evaluated to determine whether cells that express the germ cell marker Dazl were present. Dazl has previously been detected in germ cells of both human fetal females (Brekhman et al., 2000 Mol Hum Reprod 6: 465-468; Tsai et al., 2000 Feral Steril 73: 627-630) and human males (Brekhman et al., 2000 Mol Hum Reprod 6:465-468). A single human cord blood sample was split into two replicate samples and RNA was extracted from each. The replicates were then reverse-transcribed, with mock-reverse transcribed negative control samples prepared in parallel. Samples were then used in polymerase chain reaction amplification reactions (RT-PCR) using primers specific for Dazl and the housekeeping gene GAPDH. As shown, the cord blood sample used is positive for Dazl in both replicates (FIG. 17). Human cord blood is therefore a novel source of germline stem cells, or their progenitors, for oocyte and sperm production in humans.

REFERENCES

Allen, E. (1923). Ovogenesis during sexual maturity. Am. J. Anat. 31, 439-470.

Attar, E. C., and Scadden, D. T. (2004). Regulation of hematopoietic stem cell growth. Leukemia 18, 1760-1768.

Barlow, C., Hirotsune, S., Paylor, R., Liyanage, M., Eckhaus, M., Collins, F., Shiloh, Y., Crawley, J. N., Ried, T., Tagle, D., and Wynshaw-Boris, A. (1996). Atm-deficient mice: a paradigm of ataxia telangiectasia. Cell 86, 159-171.

Barlow, C., Liyanage, M., Moens, P. B., Tarsounas, M., Nagashima, K., Brown, K., Rottinghaus, S., Jackson, S. P., Tagle, D., Ried, T., and Wynshaw-Boris, A. (1998). Atm deficiency results in severe meiotic disruption as early as leptonema of prophase I. Development 125, 4007-4017.

Benson, D. A., Karsch-Mizrachi, I., Lipman, D. J., Ostell, J., and Wheeler, D. L. (2004). GenBank: update. Nucleic Acids Res. 32 Database issue, D23-D26.

Bonadonna, G., and Valagussa, P. (1985). Adjuvant systemic therapy for resectable breast cancer. J. Clin. Oncol. 3, 259-275.

Borum, K. Oogenesis in the mouse. (1961). A study of meiotic prophase. Exp. Cell Res. 24, 495-507.

Braat, A. K., Zandbergen, T., van de Water, S., Goos, H. J., and Zivkovic, D. (1999). Charatcerization of zebrafish primordial germ cells: morphology and early distribution of vasa RNA. Dev. Dyn. 216, 153-167.

Brinster, C. J., Ryu, B. Y., Avarbock, M. R., Karagenc, L., Brinster, R. L., and Orwig, K. E. (2003). Restoration of fertility by germ cell transplantation requires effective recipient preparation. Biol. Reprod. 69, 412-420.

Brinster, R. L. (2002). Germline stem cell transplanation and transgenesis. Science 296, 2174-2176.

Bucci, L. R., and Meistrich, M. L. (1987). Effects of busulfan on murine spermatogenesis: cytotoxicity, sterility, sperm abnormalities, and dominant lethal mutations. Mutat. Res. 176, 259-268.

Calvi, L. M., Adams, G. B., Weibrecht, K. W., Weber, J. M., Olson, D. P., Knicht, M. C., Martin, R. P., Schipani, E., Divietti, P., Bringhurst, F. R., Milner, L. A., Kronenberg, H. M., and Scadden, D. T. (2003). Osteoblastic cells regulate the haematopoietic stem cell niche. Nature 425, 841-846.

Canning, J., Takai, Y., and Tilly, J. L. (2003). Evidence for genetic modifiers of ovarian follicular endowment and development from studies of five inbred mouse strains. Endocrinology 144, 9-12.

Capela, A., and Temple, S. (2002). LeX/ssea-1 is expressed by adult mouse CNS stem cells, identifying them as nonependymal. Neuron 35, 865-875.

Castrillon, D. H., Quade, B. J., Wang, T. Y., Quigley, C., and Crum, C. P. (2000). The human VASA gene is specifically expressed in the germ cell lineage. Proc. Natl. Acad. Sci. USA 97, 9585-9590.

Cohen, P., and Pollard, J. W. (2001). Regulation of meiotic recombination and prophase I progression in mammals. BioEssays 23, 996-1009.

Cooke, H. J., Lee, M., Kerr, S., and Ruggiu, M. (1996). A murine homologue of the human DAZ gene is autosomal and expressed only in male and female gonads. Hum. Mol. Genet. 5, 513-516.

Cooper R. L., Goldman, J., and Vandenbergh, J. G. (1993). Monitoring of estrous cyclicity in the laboratory rodent by vaginal lavage. In Methods in Reproductive Toxicology, R. E. Chapin and J. J. Heindel, eds. (Orlando, Fla.: Academic Press), pp. 45-56.

Dearden, P., Grbic, M., and Donly, C. (2003). Vasa expression and germ-cell specification in the spider mite *Tetranychus urticae*. Dev. Genes Evol. 212, 599-603.

Deng, W., and Lin, H. (2001). Asymmetric germ cell division and oocyte determination during *Drosophila* oogenesis. Int. Rev. Cytol. 203, 93-138.

Dialynas, D. P., Quan, Z. S., Wall, K. A., Pierres, A., Quintans, J., Loken, M. R., Pierres, M., and Fitch, F. W. (1984). Characterization of the murine T cell surface molecule designated L3T4, identified by monoclonal antibody GK1.5: similarity of L3T4 to the human Leu 3/T4 molecule. J. Immunol. 131, 2445-2451.

Dias Neto, E., Correa, R. G., Verjovski-Almeida, S., Briones, M. R., Nagai, M. A., da Silva, W. Jr., Zago, M. A., Bordin, S., Costa, F. F., Goldman, G. H., Carvalho, A. F., Matsukuma, A., Baia, G. S., Simpson, D. H., Brunstein, A., de Oliveira, P. S., Bucher, P., Jongeneel, C. V., O'Hare, M. J., Soares, F., Brentani, R. R., Reis, L. F., de Souza, S. J., and Simpson, A. J. (2000). Shotgun sequencing of the human transcriptome with ORF expressed sequence tags. Proc. Natl. Acad. Sci. USA 97, 3491-3496.

Di Giacomo, M., Barchi, M., Baudet, F., Edelman, W., Keeney, S., and Jasin, M. (2005). Distinct DNA-damage-dependent and -independent responses drive the loss of oocytes in recombination-defective mouse mutants. Proc. Natl. Acad. Sci. USA 102, 737-742.

Dong, J., Albertini, D. F., Nishimori, K., Kumar, T. R., Lu, N., and Matzuk, M. M. (1996). Growth differentiation factor-9 is required during early ovarian folliculogenesis. Nature 383, 531-535.

Erickson, G. F., and Shimasaki, S. (2000). The role of the oocyte in folliculogenesis. Trends Endocrinol. Metab. 11, 193-198.

Fabioux, C., Huvet, A., Lelong, C., Robert, R., Pouvereau, S., Daniel, J. Y., Minguant, C., Le Pennec, M. (2004). Oyster vasa-like gene as a marker of the germline cell development in Crassostrea gigas. Biochem. Biophys. Res. Commun. 320, 592-598.

Faddy, M. J., Gosden, R. G., Gougeon, A., Richardson, S. J., and Nelson, J. F. (1992). Accelerated disappearance of ovarian follicles in mid-life: implications for forecasting menopause. Hum. Reprod. 7, 1342-1346.

Fox, M., Damjanov, I., Martinez-Hernandez, A., Knowles, B. B., and Solter, D. (1981). Immunohistochemical localization of the early embryonic antigen (SSEA-1) in post-implantation mouse embryos and fetal and adult tissues. Dev. Biol. 83, 391-398.

Franchi, L. L., Mandl, A. M., and Zuckerman, S. (1962). The development of the ovary and the process of oogenesis. In The Ovary, S. Zuckerman, ed. (New York, N.Y.: Academic Press), pp. 1-88.

Fujiwara, Y., Komiya, T., Kawabata, H., Sato, M., Fujimoto, H., Furusawa, M., and Noce, T. (1994). Isolation of a DEAD-family (SEQ ID NO: 1) protein gene that encodes a murine homolog of *Drosophila* vasa and its specific expression in germ cell lineage. Proc. Natl. Acad. Sci. USA 91, 12258-12262.

Geijsen, N., Horoschak, M., Kim, K., Gribnau, J., Eggan, K., and Daley, G. Q. (2004). Derivation of embryonic germ cells and male gametes from embryonic stem cells. Nature 427, 148-154.

Generoso, W. M., Stout, S. K. & Huff, S. W. (1971). Effects of alkylating agents on reproductive capacity of adult female mice. Mutat. Res. 13, 171-184.

Gilboa, L., and Lehmann, R. (2004). Repression of primordial germ cell differentiation parallels germ line stem cell maintenance. Curr. Biol. 14, 981-986.

Gosden, R. G. (1996). The vocabulary of the egg. Nature 383, 485-486.

Gosden, R. G. (2004). Germline stem cells in the postnatal ovary: is the ovary more like a testis? Hum. Reprod. Update 10, 193-195.

Gosden, R. G., Laing, S. C., Felicio, L. S., Nelson, J. F., and Finch, C. E. (1983). Imminent oocyte exhaustion and reduced follicular recruitment mark the transition to acyclicity in aging C57BL/6J mice. Biol. Reprod. 28, 255-260.

Green, E. L., and Bernstein, S. E. (1970). Do cells outside the testes participate in repopulating the germinal epithelium after irradiation? Negative results. Int. J. Radiat. Biol. Relat. Stud. Phys. Chem. Med. 17, 87-92.

Grove, J. E., Bruscia, E., and Krause, D. S. (2004). Plasticity of bone marrow-derived stem cells. Stem Cells 22, 487-500.

Hadjantonakis, A. K., Gertsenstein, M., Ikawa, M., Okabe, M., and Nagy, A. (1998). Generating green fluorescent mice by germline transmission of green fluorescent ES cells. Mech. Dev. 76, 79-90.

Heike, T., and Nakahata, T. (2004). Stem cell plasticity in the hematopoietic system. Int. J. Hematol. 79, 7-14.

Hershlag, A., and Schuster, M. W. (2004). Return of fertility after autologous stem cell transplantation. Feral. Steril. 77, 419-421.

Herzog, E. L., Chai, L., and Krause, D. S. (2003). Plasticity of marrow-derived stem cells. Blood 102, 3483-3493.

Hirshfield, A. N. (1991). Development of follicles in the mammalian ovary. Int. Rev. Cytol. 124, 43-101.

Ikenishi, K. (1998). Germ plasm in *Caenorhabditis elegans*, *Drosophila* and *Xenopus*. Dev. Growth Differ. 40, 1-10.

Johnson, J., Canning, J., Kaneko, T., Pru, J. K., and Tilly, J. L. (2004). Germline stem cells and follicular renewal in the postnatal mammalian ovary. Nature 428, 145-150.

Kanatsu-Shinohara, M., Inoue, K., Lee, J., Yoshimoto, M., Ogonuki, N., Miki, H., Baba, S., Kato, T., Kazuki, Y., Toyokuni, S., Toyoshima, M., Niwa, O., Oshimura, M., Heike, T., Nakahata, T., Ishino, F., Ogura, A., and Shinohara, T. (2004). Generation of pluripotent stem cells from neonatal mouse testis. Cell 119, 1001-1012.

Komiya, T., Itoh, K., Ikenishi, K., and Furusawa, M. (1994). Isolation and characterization of a novel gene of the DEAD (SEQ ID NO: 1) box protein family which is specifically expressed in germ cells of *Xenopus laevis*. Dev. Biol. 162, 354-363.

Lawson, K. A., and Hage, W. J. (1994). Clonal analysis of the origin of primordial germ cells in the mouse. Ciba Found. Symp. 182, 68-84, 84-91.

Lin, H. (2002). The stem-cell niche theory: lessons from flies. Nat. Rev. Genet. 3, 931-940.

Marani, E., van Oers, J. W., Tetteroo, P. A., Poelmann, R. E., van der Veeken, J., and Deenen, M. G. (1986). Stage specific embryonic carbohydrate surface antigens of primordial germ cells in mouse embryos: FAL (S.S.E.A.-1) and globoside (S.S.E.A.-3). Acta Morphol. Neerl. Scand. 24, 103-110.

Matzuk, M. M., Burns, K. H., Viveiros, M. M., and Eppig, J. J. (2002). Intercellular communication in the mammalian ovary: oocytes carry the conversation. Science 296, 2178-2180.

McGrath, S. A., Esquela, A. F., and Lee, S. J. (1995). Oocyte-specific expression of growth/differentiation factor-9. Mol. Endocrinol. 9, 131-136.

McLaren, A. (1984). Meiosis and differentiation of mouse germ cells. Symp. Soc. Exp. Biol. 38, 7-23.

McLaren, A. (2003). Primordial germ cells in the mouse. Dev. Biol. 262, 1-15.

Medvinsky, A., and Dzierzak, E. (1996). Definitive hematopoiesis is autonomously initiated by the AGM region. Cell 86, 897-906.

Meirelles, L. da S., and Nardi, N. B. (2003). Murine marrow-derived mesenchymal stem cell: isolation, in vitro expansion, and characterization. Br. J. Haematol. 123, 702-711.

Milhem, M., Mahmud, N., Lavelle, D., Araki, H., DeSimone, J., Saunthararajah, Y., and Hoffman, R. (2004). Modification of hematopoietic stem cell fate by 5aza 2' deoxycytidine and trichostatin A. Blood 103, 4102-4110.

Mintz, B., and Russell, E. S. (1957). Gene-induced embryological modification of primordial germ cells in the mouse. J. Exp. Zool. 134, 207-230.

Molyneaux, K., and Wylie, C. (2004). Primordial germ cell migration. Int. J. Dev. Biol. 48, 537-544.

Morita, Y., Perez, G. I., Paris, F., Miranda, S., Ehleiter, D., Haimovitz-Friedman, A., Fuks, Z., Xie, Z., Reed, J. C., Schuchman, E. H., Kolesnick, R. N., and Tilly, J. L. (2000). Oocyte apoptosis is suppressed by disruption of the acid sphingomyelinase gene or by sphingosine-1-phosphate therapy. Nat. Med. 6, 1109-1114.

Morrison, S. J., Uchida, N., Weissman, I. L. (1995). The biology of hematopoietic stem cells. Annu. Rev. Cell Dev. Biol. 11, 35-71.

Noce, T., Okamoto-Ito, S., and Tsunekawa, N. (2001). Vasa homolog genes in mammalian germ cell development. Cell Struct. Funct. 26, 131-136.

Okada, S., Nakauchi, H., Nagayoshi, K., Nishikawa, S., Nishikawa, S., Miura, Y., and Suda, T. (1991). Enrichment and characterization of murine hematopoietic stem cells that express c-kit molecule. Blood 78, 1706-1712.

Okada, S., Nakauchi, H., Nagayoshi, K., Nishikawa, S., Miura, Y., and Suda, T. (1992). In vivo and in vitro stem cell function of c-kit- and Sca-1-positive murine hematopoietic cells. Blood 80, 3044-3050.

Perez, G. I., Knudson, C. M., Leykin, L., Korsmeyer, S. J. & Tilly, J. L. (1997). Apoptosis-associated signaling pathways are required for chemotherapy-mediated female germ cell destruction. Nat. Med. 3, 1228-1232.

Perez, G. I., Robles, R., Knudson, C. M., Flaws, J. A., Korsmeyer, S. J., and Tilly, J. L. (1999). Prolongation of ovarian lifespan into advanced chronological age by Bax-deficiency. Nat. Genet. 21, 200-203

Peters, H. (1969). The development of the mouse ovary from birth to maturity. Acta Endocrinol. 62, 98-116.

Peters, H. (1970). Migration of gonocytes into the mammalian gonad and their differentiation. Phil. Trans. Roy. Soc. Lond. B. 259, 91-101.

Philpott, C. C., Ringuette, M. J., and Dean, J. (1987). Oocyte-specific expression and developmental regulation of ZP3, the sperm receptor of the mouse zona pellucida. Dev. Biol. 121, 568-575.

Pfaffl, M. W. (2001). A new mathematical model for relative quantification in real-time RT-PCR. Nucleic Acids Res. 29, e45.

Rajkovic, A., Pangas, S. A., Ballow, D., Suzumori, N., and Matzuk, M. M. (2004). NOBOX deficiency disrupts early folliculogenesis and oocyte-specific gene expression. Science 305, 1157-1159.

Rich, I. N. (1995). Primordial germ cells are capable of producing cells of the hematopoietic system in vitro. Blood 86, 463-472.

Richardson, S. J., Senikas, V., and Nelson, J. F. (1987). Follicular depletion during the menopausal transition: evidence for accelerated loss and ultimate exhaustion. J. Clin. Endocrinol. Metab. 65, 1231-1237.

Rongo, C., Broihier, H. T., Moore, L., Van Doren, M., Forbes, A., and Lehmann, R. (1997). Germ plasm assembly and germ cell migration in *Drosophila*. Cold Spring Harb. Symp. Quant. Biol. 62, 1-11.

Rous sell, D. L., and Bennett, K. L. (1993). glh-1, a germ-line putative RNA helicase from *Caenorhabditis*, has four zinc fingers. Proc. Natl. Acad. Sci. USA 90, 9300-9304.

Ryu, B. Y., Orwig, K. E., Avarbock, M. R., and Brinster, R. L. (2003). Stem cell and niche development in the postnatal rat testis. Dev. Biol. 263, 253-263.

Saitou, M., Barton, S. C., and Surani, M. A. (2002). A molecular programme for the specification of germ cell fate in mice. Nature 418, 293-300.

Salooja, N., Chatterjee, R., McMillan, A. K., Kelsey, S. M., Newland, A. C., Milligan, D. W., Franklin, I. M., Hutchinson, R. M., Linch, D. C., and Goldstone, A. H. (1994). Successful pregnancies in women following single autotransplant for acute myeloid leukemia with a chemotherapy ablation protocol. Bone Marrow Transplant. 13, 431-435.

Salooja, N., Szydlo, R. M., Socie, G., Rio, B., Chatterjee, R., Ljungman, P., Van Lint, M. T., Powles, R., Jackson, G., Hinterberger-Fischer, M., Kolb, H. J., and Apperley, J. F; Late Effects Working Party of the European Group for Blood and Marrow Transplantation. (2001). Pregnancy outcomes after peripheral blood or bone marrow transplantation: a retrospective study. Lancet 358, 271-276.

Salustri, A., Fulop, C., Camaioni, A., and Hascall, V. C. (2004). Oocyte-granulosa cell interactions. In The Ovary, 2nd Edition, P. C. K. Leung and E. Y. Adashi, eds. (San Diego: Elsevier Academic Press), pp. 131-143.

Samuelsson, A., Fuchs, T., Simonsson, B., and Bjorkholm, M. (1993). Successful pregnancy in a 28-year-old patient autografted for acute lymphoblastic leukemia following myeloablative treatment including total body irradiation. Bone Marrow Transplant. 12, 659-660.

Sanders, J. E., Hawley, J., Levy, W., Gooley, T., Buckner, C. D., Deeg, H. J., Doney, K., Storb, R., Sullivan, K., Witherspoon, R., and Appelbaum, F. R. (1996). Pregnancies following high-dose cyclophosphamide with or without high-dose busulfan or total-body irradiation and bone marrow transplantation. Blood 87, 3045-3052.

Sarmiento, M., Glasebrook, A. L., and Fitch, F. W. (1980). IgG or IgM monoclonal antibodies reactive with different determinants on the molecular complex bearing Lyt2 antigen block T cell-mediated cytolysis in the absence of complement. J. Immunol. 125, 2665-2672.

Schöler, H. R., Hatzopoulos, A. K., Balling, R., Suzuki, N., and Gruss, P. (1989). A family of octamer-specific proteins present during mouse embryogenesis: evidence for germline-specific expression of an Oct factor. EMBO J. 8, 2543-2550.

Sette, C., Dolci, S., Geremia, R., and Rossi, P. (2000). The role of stem cell factor and of alternative c-kit gene products in the establishment, maintenance and function of germ cells. Int. J. Dev. Biol. 44, 599-608.

Shen, H., Cheng, T., Olszak, I., Garcia-Zepeda, E., Lu, Z., Herrmann, S., Falon, R., Luster, A. D., and Scadden, D. T. (2001). CXCR-4 desensitization is associated with tissue localization of hematopoietic progenitor cells. J. Immunol. 166, 5027-5033.

Shiromizu, K., Thorgeirsson, S. S., and Mattison, D. R. (1984). Effect of cyclophosphamide on oocyte and follicle number in Sprague-Dawley rats, C57BL/6N and DBA/2N mice. Pediatr. Pharmacol. 4, 213-221.

Soyal, S. M., Amleh, A., and Dean. J. (2000). FIG. □, a germ cell-specific transcription factor required for ovarian follicle formation. Development 127, 4645-4654.

Spangrude, G. J., and Scollay, R. (1990). A simplified method for enrichment of mouse hematopoietic stem cells. Exp. Hematol. 18, 920-926.

Spangrude, G. J., Heimfeld, S., and Weissman, I. L. (1988). Purification and characterization of mouse hematopoietic stem cells. Science 241, 58-62.

Spradling, A. C. (1993). Developmental genetics of oogenesis. In The Development of *Drosophila melanogaster*, Volume I, M. Bate and A. Martinez Arias, eds. (Cold Spring Harbor, N.Y.: Cold Spring Harbor Press), pp. 1-70.

Spradling, A. H., Drummond-Barbosa, D., and Kai, T. (2001). Stem cells find their niche. Nature 414, 98-104.

Su, A. I., Cooke, M. P., Ching, K. A., Hakak, Y., Walker, J. R., Wiltshire, T., Orth, A. P., Vega, R. G., Sapinoso, L. M., Moqrich, A., Patapoutian, A., Hampton, G. M., Schultz, P. G., and Hogenesch, J. B. (2004). A gene atlas of the mouse and human protein-encoding transcriptomes. Proc. Natl. Acad. Sci. USA 101, 6062-6067.

Suzumori, N., Yan, C., Matzuk, M. M., and Rajkovic, A. (2002). Nobox is a homeobox-encoding gene preferentially expressed in primordial and growing oocytes. Mech. Dev. 111, 137-141.

Szabo, P. E., Hubner, K., Schöler, H., and Mann, J. R. (2002). Allele-specific expression of imprinted genes in mouse migratory primordial germ cells. Mech. Dev. 115, 157-160.

te Velde, E. R., and Pearson, P. L. (2002). The variability of female reproductive ageing. Hum. Reprod. Update 8, 141-154.

Telfer, E. E. (2004). Germline stem cells in the postnatal mammalian ovary: a phenomenon of prosimian primates and mice? Reprod. Biol. Endocrinol. 2, 24.

Tilly, J. L. (2001). Commuting the death sentence: how oocytes strive to survive. Nat. Rev. Mol. Cell. Biol. 2, 838-848.

Tilly, J. L. (2003). Ovarian follicle counts—not as simple as 1, 2, 3. Reprod. Biol. Endocrinol. 1, 11.

Tropel, P., Noel, D., Platet, N., Legrand, P., Benabid, A.-L., and Berger, F. (2004). Isolation and characterisation of mesenchymal stem cells from adult mouse bone marrow. Exp. Cell Res. 295, 395-406.

Tsuda, M., Sasaoka, Y., Kiso, M., Abe, K., Haraguchi, S., Kobayashi, S., and Saga, Y. (2003). Conserved roles of nanos proteins in germ cell development. Science 301, 1239-1241.

Van de Rijn, M., Heimfeld, S., Spangrude, G. J., and Weissman, I. L. (1989). Mouse hematopoietic stem-cell antigen Sca-1 is a member of the Ly-6 antigen family. Proc. Natl. Acad. Sci. USA 86, 4634-4638.

van den Hurk, R., and Zhao, J. (2005). Formation of mammalian oocytes and their growth, differentiation and maturation within ovarian follicles. Theriogenology 63, 1717-1751.

Williams, D. E., de Vries, P., Namen, A. E., Widmer, M. B., and Lyman, S. D. (1992). The Steel factor. Dev. Biol. 151, 368-376.

Wognum, A. W., Eaves, A. C., and Thomas, T. E. (2003). Identification and isolation of hematopoietic stem cells. Arch. Med. Res. 34, 461-475.

Xu, Y., Ashley, T., Brainerd, E. E., Bronson, R. T., Meyn, M. S., and Baltimore, D. (1996). Targeted disruption of ATM leads to growth retardation, chromosomal fragmentation during meiosis, immune defects, and thymic lymphoma. Genes Dev. 10, 2411-2422.

Yeom, Y. I., Fuhrmann, G., Ovitt, C. E., Brehm, A., Ohbo, K., Gross, M., Hübner, K., and Schöler, H. R. (1996). Germline regulatory element of Oct-4 specific for the totipotent cycle of embryonal cells. Development 122, 881-894.

Yoshimizu, T., Sugiyama, N., De Felice, M., Yeom, Y. I., Ohbo, K., Masuko, K., Obinata, M., Abe, K., Schöler, H. R., and Matsui, Y. (1999). Germline-specific expression of the Oct-4/green fluorescent protein (GFP) transgene in mice. Dev. Growth Differ. 41, 675-684.

Yuan, L., Liu, J. G., Hoja, M. R., Wilbertz, J., Nordqvist, K., and Hoog, C. (2002). Female germ cell aneuploidy and embryo death in mice lacking the meiosis-specific protein SCP3. Science 296, 1115-1118.

Zhu, C. H., and Xie, T. (2003). Clonal expansion of ovarian germline stem cells during niche formation in *Drosophila*. Development 130, 2579-258.

Zuckerman, S. (1951). The number of oocytes in the mature ovary. Recent Prog. Horm. Res. 6, 63-108.

Zuckerman, S., and Baker, T. G. (1977). The development of the ovary and the process of oogenesis. In The Ovary, S. Zuckerman and B. J. Weir, eds. (New York, N.Y.: Academic Press), pp. 41-67.

We claim:

1. A method of producing an oocyte in a female mammalian subject in need thereof, comprising:
   obtaining non-embryonic stem cells from the ovarian tissue;
   purifying the stem cells by isolating from the stem cells a population of cells that are mitotically competent and express Vasa, Oct-4, Dazl, and Stella and, optionally, a stage-specific embryonic antigen, thereby obtaining a purified population of female germline stem cells:
   preparing a composition comprising a therapeutically effective amount of the purified population of female germline stem cells, wherein said purified population of female germline stem cells are autologous or allogenic, and a pharmaceutically acceptable carrier: and
   administering said composition to an ovary of the subject, wherein the cells engraft into the ovary, thereby producing an oocyte in the subject.

2. A method of inducing folliculogenesis in a female subject in need thereof, comprising:
   obtaining non-embryonic stem cells from ovarian tissue;
   purifying the stem cells by isolating from the stem cells a population of cells that are mitotically competent and express Vasa, Oct-4, Dazl, and Stella and, optionally, a stage-specific embryonic antigen, thereby obtaining a purified population of female germline stem cells;
   preparing a composition comprising a therapeutically effective amount of the purified population of female germline stem cells, wherein said purified population of female germline stem cells are autologous or allogenic, and a pharmaceutically acceptable carrier: and
   administering said composition to an ovary of the subject, thereby inducing folliculogenesis in the subject.

3. A method of treating infertility in a female subject in need thereof comprising:
   obtaining non-embryonic stem cells from ovarian tissue;
   purifying the stem cells by isolating from the stem cells a population of cells that are mitotically competent and express Vasa, Oct-4, Dazl, and Stella and, optionally, a stage-specific embryonic antigen, thereby obtaining a purified population of female germline stem cells:
   preparing a composition comprising a therapeutically effective amount of the purified population of female germline stem cells, wherein said purified population of female germline stem cells are autologous or allogenic, and a pharmaceutically acceptable carrier: and
   administering said composition into an ovary of the subject, thereby treating infertility.

4. The method of any of claims 1, 2, and 3, wherein the cells are human cells.

5. The method of claim 4, wherein the purified population of cells is about 50 to about 55%, about 55 to about 60%, about 65 to about 70%, about 70 to about 75%, about 75 to about 80%, about 80 to about 85%, about 90 to about 95% or about 95 to about 100% of the cells in the population.

6. The method of any one of claims 1, 2 and 3, wherein the stage-specific embryonic antigen is stage-specific embryonic antigen-1.

7. The method of any one of claims 1, 2 and 3, wherein the human cells are cells from a human female having exhausted ovarian or follicular reserves.

8. The method of any one of claims 1, 2 and 3, wherein the step of isolating comprises isolating a first population of mitotically active cells from a sample of ovarian tissue by selecting cells in the sample that express a first genetic marker selected from a stage-specific embryonic antigen, Vasa, Oct-4, Dazl or Stella.

9. The method of claim 8, wherein the isolating step further comprises isolating one or more mitotically active cells from said first population by selecting the expression of a second genetic marker by the mitotically active cells, wherein the second genetic marker is selected from a stage-specific embryonic antigen, Vasa, Oct-4, Dazl or Stella, and said second genetic marker is different from said first genetic marker.

10. The method of claim 3, wherein an oocyte results from the engrafted cells, and wherein the method further comprises:
    removing the oocyte from the female subject; fertilizing the oocyte in vitro to form a zygote; and
    inserting the zygote or a multi-celled embryo derived from the zygote into the female subject.

11. The method of claim 8, wherein the isolating step comprises selecting protein corresponding to the first genetic marker.

12. The method of claim 8, wherein the first genetic marker is Vasa.

13. The method of claim 12, wherein the selection of cells in the sample comprises contacting the sample with a multiplicity of antibodies comprising an antibody that specifically binds to human Vasa.

14. The method of claim 8, wherein the isolating step comprises fluorescence activated cell sorting.

* * * * *